(12) United States Patent
Askew et al.

(10) Patent No.: US 12,268,754 B2
(45) Date of Patent: Apr. 8, 2025

(54) COMPOSITION AND METHODS FOR TREATMENT OF ORNITHINE TRANSCARBAMYLASE DEFICIENCY

(71) Applicant: Translate Bio, Inc., Lexington, MA (US)

(72) Inventors: Kim Askew, Lexington, MA (US); Jou-Ku Chung, Lexington, MA (US); Frank DeRosa, Lexington, MA (US); Michael Heartlein, Lexington, MA (US); Shrirang Karve, Lexington, MA (US); Thomas McCauley, Lexington, MA (US); Lianne Smith, Lexington, MA (US); Ann J. Barbier, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 641 days.

(21) Appl. No.: 17/448,996

(22) Filed: Sep. 27, 2021

(65) Prior Publication Data
US 2022/0072152 A1    Mar. 10, 2022

Related U.S. Application Data

(62) Division of application No. 16/228,596, filed on Dec. 20, 2018, now Pat. No. 11,167,043.

(60) Provisional application No. 62/608,547, filed on Dec. 20, 2017.

(51) Int. Cl.
| | |
|---|---|
| *A61K 48/00* | (2006.01) |
| *A61K 9/00* | (2006.01) |
| *A61K 9/127* | (2006.01) |
| *A61K 9/1272* | (2025.01) |
| *A61K 38/45* | (2006.01) |
| *A61K 47/69* | (2017.01) |
| *A61P 3/00* | (2006.01) |
| *C12N 15/52* | (2006.01) |
| *C12N 15/85* | (2006.01) |

(52) U.S. Cl.
CPC .......... *A61K 48/005* (2013.01); *A61K 9/0019* (2013.01); *A61K 9/1272* (2013.01); *A61K 38/45* (2013.01); *A61K 47/6929* (2017.08); *A61K 48/0025* (2013.01); *A61K 48/0075* (2013.01); *A61K 48/0083* (2013.01); *A61P 3/00* (2018.01); *C12N 15/52* (2013.01); *C12N 15/85* (2013.01); *C12Y 201/03003* (2013.01)

(58) Field of Classification Search
CPC .............. A61K 48/005; A61K 47/6929; A61K 48/0083; C12N 15/52; C12N 15/85; C12Y 201/03003
USPC ............. 424/9.1; 435/91.1, 91.31, 455, 458; 514/44 R; 536/23.1
See application file for complete search history.

(56) References Cited

U.S. PATENT DOCUMENTS

| | | |
|---|---|---|
| 5,705,385 A | 1/1998 | Bally et al. |
| 5,976,567 A | 11/1999 | Wheeler |
| 5,981,501 A | 11/1999 | Wheeler et al. |
| 6,534,484 B1 | 3/2003 | Wheeler et al. |
| 6,815,432 B2 | 11/2004 | Wheeler et al. |
| 7,422,902 B1 | 9/2008 | Wheeler et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,901,708 B2 | 3/2011 | MacLachlan et al. |
| 8,101,741 B2 | 1/2012 | MacLachlan et al. |
| 8,188,263 B2 | 5/2012 | MacLachlan et al. |
| 8,236,943 B2 | 8/2012 | Lee et al. |
| 8,329,070 B2 | 12/2012 | MacLachlan et al. |
| 8,513,403 B2 | 8/2013 | MacLachlan et al. |
| 8,569,256 B2 | 10/2013 | Heyes et al. |
| 8,710,200 B2 | 4/2014 | Schrum et al. |
| 8,822,663 B2 | 9/2014 | Schrum et al. |
| 8,883,202 B2 | 11/2014 | Manoharan et al. |
| 8,980,864 B2 | 3/2015 | Hoge et al. |
| 9,051,567 B2 | 6/2015 | Fitzgerald et al. |
| 9,061,059 B2 | 6/2015 | Chakraborty et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,181,319 B2 | 11/2015 | Schrum et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |

(Continued)

FOREIGN PATENT DOCUMENTS

| | | | |
|---|---|---|---|
| AU | 2014250713 A1 * | 11/2014 | ......... A61K 31/7105 |
| CA | 2807 552 | 9/2012 | |

(Continued)

OTHER PUBLICATIONS

Brandt et al (Abstract 41, Molecular Genetics and Metabolism, vol. 120, S17-S145 (2016)) (Year: 2016).*
Wang et al (Molecular Genetics and Metabolism, vol. 105, pp. 203-211 (2012)) (Year: 2012).*
Wang et al (Gene Therapy, vol. 19, pp. 404-410 (2012)) (Year: 2012).*
Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, vol. 3, Issue 5, (2016).

(Continued)

*Primary Examiner* — Jane J Zara
(74) *Attorney, Agent, or Firm* — LATHROP GPM LLP; James H. Velema, Esq.

(57) ABSTRACT

The present invention provides, among other things, methods of treating ornithine transcarbamylase deficiency, including administering to a subject in need of treatment a composition comprising an mRNA encoding an ornithine transcarbamylase protein at a low dose and at an administration interval such that at least one symptom or feature of the OTC deficiency is reduced.

18 Claims, 6 Drawing Sheets

Specification includes a Sequence Listing.

(56) References Cited

U.S. PATENT DOCUMENTS

| | | |
|---|---|---|
| 9,192,651 B2 | 11/2015 | Chakraborty et al. |
| 9,220,755 B2 | 12/2015 | Chakraborty et al. |
| 9,220,792 B2 | 12/2015 | Chakraborty et al. |
| 9,233,141 B2 | 1/2016 | Chakraborty et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,394,234 B2 | 7/2016 | Chen et al. |
| 9,404,127 B2 | 8/2016 | Yaworski et al. |
| 9,428,535 B2 | 8/2016 | De Fougerolles et al. |
| 9,428,751 B2 | 8/2016 | MacDonald et al. |
| 9,447,164 B2 | 9/2016 | Schrum et al. |
| 9,464,124 B2 | 10/2016 | Bancel et al. |
| 9,492,386 B2 | 11/2016 | MacLachlan et al. |
| 9,504,651 B2 | 11/2016 | MacLachlan et al. |
| 9,504,734 B2 | 11/2016 | Bancel et al. |
| 9,518,272 B2 | 12/2016 | Yaworksi et al. |
| 9,572,874 B2 | 2/2017 | Fotin-Mleczek et al. |
| 9,572,896 B2 | 2/2017 | Bancel et al. |
| 9,572,897 B2 | 2/2017 | Bancel et al. |
| 9,587,003 B2 | 3/2017 | Bancel et al. |
| 9,616,084 B2 | 4/2017 | Mutzke |
| 9,623,095 B2 | 4/2017 | Kallen et al. |
| D787,703 S | 5/2017 | Mayer |
| 9,636,301 B2 | 5/2017 | Weber |
| 9,655,955 B2 | 5/2017 | Hoerr et al. |
| 9,657,295 B2 | 5/2017 | Schrum et al. |
| 9,669,089 B2 | 6/2017 | Thess et al. |
| 9,670,152 B2 | 6/2017 | Payne et al. |
| 9,675,668 B2 | 6/2017 | Bancel et al. |
| 9,682,139 B2 | 6/2017 | Monoharan et al. |
| 9,683,233 B2 | 6/2017 | Thess |
| 9,687,550 B2 | 6/2017 | Manoharan et al. |
| 9,688,729 B2 | 6/2017 | Kramps et al. |
| 11,167,043 B2 * | 11/2021 | Askew ............... A61K 48/0025 |
| 2002/0192651 A1 | 12/2002 | Wheeler et al. |
| 2003/0181410 A1 | 9/2003 | Wheeler et al. |
| 2004/0142025 A1 | 7/2004 | MacLachlan et al. |
| 2006/0008910 A1 | 1/2006 | MacLachlan et al. |
| 2006/0083780 A1 | 4/2006 | Heyes et al. |
| 2007/0135372 A1 | 6/2007 | MacLachlan et al. |
| 2009/0270481 A1 | 10/2009 | MacLachlan et al. |
| 2010/0041152 A1 | 2/2010 | Wheeler et al. |
| 2011/0244026 A1 | 10/2011 | Guild et al. |
| 2011/0311583 A1 | 12/2011 | Manoharan et al. |
| 2012/0065252 A1 | 3/2012 | Schrum et al. |
| 2012/0128760 A1 | 5/2012 | Manoharan et al. |
| 2012/0142756 A1 | 6/2012 | Guild et al. |
| 2012/0202871 A1 | 8/2012 | Heyes et al. |
| 2012/0237975 A1 | 9/2012 | Schrum et al. |
| 2012/0251618 A1 | 10/2012 | Schrum et al. |
| 2012/0328668 A1 | 12/2012 | MacLachlan et al. |
| 2013/0195967 A1 | 8/2013 | Guild et al. |
| 2013/0237594 A1 | 9/2013 | De Fougerolles et al. |
| 2013/0259923 A1 | 10/2013 | Bancel et al. |
| 2013/0259924 A1 | 10/2013 | Bancel et al. |
| 2013/0266640 A1 | 10/2013 | De Fougerolles et al. |
| 2014/0010861 A1 | 1/2014 | Bancel et al. |
| 2014/0044772 A1 | 2/2014 | MacLachlan et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221465 A1 | 8/2014 | Bancel et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0294937 A1 | 10/2014 | MacLachlan et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0111945 A1 | 4/2015 | Geisbert et al. |
| 2015/0166465 A1 | 6/2015 | Chen et al. |
| 2015/0190515 A1 | 7/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0082092 A1 | 3/2016 | Hoerr et al. |
| 2016/0089424 A1 | 3/2016 | Hoerr et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0199485 A1 | 7/2016 | Manoharan et al. |
| 2016/0213785 A1 | 7/2016 | Manoharan et al. |
| 2016/0237108 A1 | 8/2016 | Fraley et al. |
| 2016/0237134 A1 | 8/2016 | Hoge et al. |
| 2016/0250354 A1 | 9/2016 | Manoharan et al. |
| 2016/0251681 A1 | 9/2016 | Yaworski et al. |
| 2016/0256567 A1 | 9/2016 | Heyes et al. |
| 2016/0256568 A1 | 9/2016 | Heyes et al. |
| 2016/0256573 A1 | 9/2016 | de Fougerolles et al. |
| 2016/0264971 A1 | 9/2016 | Geisbert et al. |
| 2016/0264975 A1 | 9/2016 | Schrum et al. |
| 2016/0274089 A1 | 9/2016 | Ciufolini et al. |
| 2016/0304552 A1 | 10/2016 | Roy et al. |
| 2016/0317647 A1 | 11/2016 | Ciaramella et al. |
| 2016/0317676 A1 | 11/2016 | Hope et al. |
| 2016/0331828 A1 | 11/2016 | Ciaramella et al. |
| 2016/0348099 A1 | 12/2016 | Roy et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2016/0367687 A1 | 12/2016 | Manoharan et al. |
| 2016/0367702 A1 | 12/2016 | Hoge et al. |
| 2016/0375134 A1 | 12/2016 | Bancel et al. |
| 2017/0000858 A1 | 1/2017 | Fotin-Mleczek et al. |
| 2017/0000870 A1 | 1/2017 | Hoerr et al. |

(56) References Cited

U.S. PATENT DOCUMENTS

| | | |
|---|---|---|
| 2017/0000871 A1 | 1/2017 | Probst et al. |
| 2017/0002060 A1 | 1/2017 | Bolen et al. |
| 2017/0007702 A1 | 1/2017 | Heyes et al. |
| 2017/0014496 A1 | 1/2017 | Fotin-Mleczek et al. |
| 2017/0028059 A1 | 2/2017 | Baumhof et al. |
| 2017/0029847 A1 | 2/2017 | Thess |
| 2017/0042814 A1 | 2/2017 | Yaworski et al. |
| 2017/0056528 A1 | 3/2017 | De Fougerolles et al. |
| 2017/0056529 A1 | 3/2017 | Thess et al. |
| 2017/0065675 A1 | 3/2017 | Bancel et al. |
| 2017/0065727 A1 | 3/2017 | Fotin-Mleczek et al. |
| 2017/0114378 A1 | 4/2017 | Wochner et al. |
| 2017/0128549 A1 | 5/2017 | Fotin-Mleczek et al. |
| 2017/0136131 A1 | 5/2017 | Roy et al. |
| 2017/0136132 A1 | 5/2017 | Roy et al. |
| 2017/0143631 A1 | 5/2017 | Chen et al. |
| 2017/0143796 A1 | 5/2017 | Schrum et al. |
| 2017/0151333 A1 | 6/2017 | Heyes et al. |
| 2017/0157268 A1 | 6/2017 | Ansell et al. |
| 2017/0166905 A1 | 6/2017 | Eberle et al. |
| 2017/0173128 A1 | 6/2017 | Hoge et al. |
| 2017/0175129 A1 | 6/2017 | Roy et al. |
| 2017/0182081 A1 | 6/2017 | Mutzke |
| 2017/0182150 A1 | 6/2017 | Kallen et al. |

FOREIGN PATENT DOCUMENTS

| | | |
|---|---|---|
| EP | 1519 714 | 10/2010 |
| EP | 2449 106 | 5/2012 |
| EP | 2338 478 | 6/2013 |
| EP | 2823 809 | 1/2015 |
| WO | WO2005/026372 | 3/2005 |
| WO | WO2005/121348 A1 | 12/2005 |
| WO | WO2009/127060 | 10/2009 |
| WO | WO2010042877 A1 | 4/2010 |
| WO | WO2011/068810 A1 | 6/2011 |
| WO | WO2011/141705 | 11/2011 |
| WO | WO2012/019168 | 2/2012 |
| WO | WO2012/135805 | 10/2012 |
| WO | WO2013/039857 | 3/2013 |
| WO | WO2013/039861 | 3/2013 |
| WO | WO2013/090186 A1 | 6/2013 |
| WO | WO2013/101690 | 7/2013 |
| WO | WO2013/126803 | 8/2013 |
| WO | WO2013/130161 | 9/2013 |
| WO | WO2013/151663 | 10/2013 |
| WO | WO2013/151664 | 10/2013 |
| WO | WO2013/151666 | 10/2013 |
| WO | WO2013/151667 | 10/2013 |
| WO | WO2013/151668 | 10/2013 |
| WO | WO2013/151670 | 10/2013 |
| WO | WO2013/151671 | 10/2013 |
| WO | WO2013/151672 | 10/2013 |
| WO | WO2013/151736 | 10/2013 |
| WO | WO2013/185069 A1 | 12/2013 |
| WO | WO2014/113089 | 7/2014 |
| WO | WO2014/144039 | 9/2014 |
| WO | WO2014/144711 | 9/2014 |
| WO | WO2014/144767 | 9/2014 |
| WO | WO2014/152027 | 9/2014 |
| WO | WO2014/152030 | 9/2014 |
| WO | WO2014/152031 | 9/2014 |
| WO | WO2014/152211 | 9/2014 |
| WO | WO2014/152540 | 9/2014 |
| WO | WO2014/158795 | 10/2014 |
| WO | WO2014/159813 | 10/2014 |
| WO | WO2015/006747 A2 | 1/2015 |
| WO | WO2015/048744 | 4/2015 |
| WO | WO2015/051169 | 4/2015 |
| WO | WO2015/051173 | 4/2015 |
| WO | WO2015/058069 | 4/2015 |
| WO | WO2015/085318 | 6/2015 |
| WO | WO2015/089511 | 6/2015 |
| WO | WO2015/011633 | 1/2016 |
| WO | WO2016/054421 | 4/2016 |
| WO | WO2016/070166 A2 | 5/2016 |
| WO | WO2016/071857 | 5/2016 |
| WO | WO2016/077123 | 5/2016 |
| WO | WO2016/077125 | 5/2016 |
| WO | WO2016/118724 | 7/2016 |
| WO | WO2016/118725 | 7/2016 |
| WO | WO2016118697 A1 | 7/2016 |
| WO | WO2016/154127 | 9/2016 |
| WO | WO2016/164762 | 10/2016 |
| WO | WO2016/183366 A2 | 11/2016 |
| WO | WO2016/197132 A1 | 12/2016 |
| WO | WO2016/197133 A1 | 12/2016 |
| WO | WO2016/201377 A1 | 12/2016 |
| WO | WO2017/019891 A2 | 2/2017 |
| WO | WO2017/049074 A1 | 3/2017 |
| WO | WO2017/049275 A2 | 3/2017 |
| WO | WO2017/049286 A1 | 3/2017 |
| WO | WO2017/102010 A1 | 6/2017 |
| WO | WO2017/103088 A1 | 6/2017 |
| WO | WO2017/108087 A1 | 6/2017 |
| WO | WO2017/109134 A1 | 6/2017 |
| WO | WO2017/109161 A1 | 6/2017 |
| WO | WO2017/218524 A1 | 12/2017 |
| WO | WO2019/207060 | 10/2019 |

OTHER PUBLICATIONS

Brandt et al., "Messenger RNA (mRNA) delivery to the liver corrects ornithine transcarbamylase deficiency in a mouse disease model", Molecular Genetics and Metabolism, vol. 120, No. 1-2, p. S31, (2017).

Database EMBL, Database Accession No. BAW43135 (Dec. 5, 2013).

Engel et al., "Analysis of mRNA transcripts improves the success rate of molecular genetic testing in OTC deficiency", Molecular Genetics and Metabolism, vol. 94, No. 3, pp. 292-297, (2008).

International Search Report and Written Opinion for PCT/US18/66970, dated Jun. 27, 2019.

Kowalski et al., "Delivering the Messenger: Advances in Technologies for Therapeutic mRNA Delivery", Mol Ther., 27(4), pp. 710-728, (2019).

Matsui et al., "Messenger RNA-based therapeutics for the treatment of apoptosis- associated diseases", Sci Rep., 5:15810, (2015).

Moscioni et al., "Long-term correction of ammonia metabolism and prolonged survival in ornithine transcarbamylase-deficient mice following liver-directed treatment with adeno-associated viral vectors", Mol Ther., Jul. 2006, vol. 14, No. 1, pp. 25-33, (2006).

Prieve et al., "Abstract 413: Correction of Ornithine Transcarbamylase Deficiency Following Treatment with PhaseRx's Hybrid mRNA TechnologyTM Delivery System and Safety Evaulation in Rats and Non-Human Primates", 20th Annual Meeting of the American-Society-Of-Gene-And-Cell-Therapy (ASGCT), vol. 25, p. 191, (2017).

Prieve et al., "Targeted mRNA Therapy for Ornithine Transcarbamylase Deficiency" Molecular Therapy: The Journal of the American Society of Gene Therapy, vol. 26, No. 3, (2018).

Trepotec et al., "Delivery of mRNA Therapeutics for the Treatment of Hepatic Diseases", Mol Ther., 27(4), pp. 794-802, (2019).

Wang et al., "Preclinical evaluation of a clinical candidate AAV8 vector for ornithine transcarbamylase (OTC) deficiency reveals functional enzyme from each persisting vector genome", Mol Genet Metab., Feb. 2012, vol. 105, No. 2, pp. 203-211, (2012).

Wang et al., "Sustained correction of OTC deficiency in spf( ash) mice using optimized self-complementary AAV2/8 vectors", Gene Ther., Apr. 2012, vol. 19, No. 4, pp. 404-410, (2012).

* cited by examiner

COMPOSITION AND METHODS FOR TREATMENT OF ORNITHINE TRANSCARBAMYLASE DEFICIENCY

RELATED APPLICATIONS

This application is a Divisional Application of U.S. application Ser. No. 16/228,596, filed Dec. 20, 2018, which claims priority to U.S. Provisional Application, Ser. No. 62/608,547, filed on Dec. 20, 2017, the disclosure in its entirety is hereby incorporated by reference.

INCORPORATION BY REFERENCE OF SEQUENCE LISTING

The content of the text file named "MRT-2010US2_SL25.txt", which was created on Sep. 24, 2021 and is 17.4 kilobytes in size, is hereby incorporated by reference in its entirety.

BACKGROUND

Ornithine transcarbamylase (OTC) deficiency is an X-linked genetic disorder characterized by mutations in the gene for OTC. Mutations in the OTC gene eliminate or reduce the ability of the OTC enzyme catalyze the synthesis of citrulline (in the liver and small intestine) from carbamoyl phosphate and ornithine. As a result, excess nitrogen, in the form of ammonia, accumulates in the blood, and travels to the nervous system, resulting in the symptoms associated with OTC deficiency. Mutations that abolish OTC activity completely result in the severe, neonatal-onset form while mutations leading to decreased OTC activity result in the late-onset phenotypes.

OTC deficiency is the most common type of urea cycle disorder. Males with the severe, neonatal-onset type are normal at birth but develop poor sucking, hypotonia and lethargy after a few days, rapidly progressing into somnolence and coma. Seizures and hyperventilation may also be present. If untreated, severe encephalopathy will develop with a high risk for death. Patients with a milder form can present at any age. In infants, symptoms can be induced when switching from breast milk to whole milk. In children and adults, environmental stressors (i.e. fasting, high protein diet, pregnancy and the postpartum period, intercurrent illness, surgery) can trigger episodes of hyperammonemic encephalopathy along with nausea, vomiting, headaches, erratic behavior, delirium and combativeness. These episodes can also result in hyperammonemic coma. Neurological complications of hyperammonemic coma include developmental delay and (sometimes) severe cognitive impairment. Many female carriers are asymptomatic; however they can be affected to the same extent as males if the degree of X-inactivation of the disease allele is unfavorable. Coagulopathy is a frequent finding during metabolic decompensation and sometimes evolves into acute liver failure.

Currently, there is no cure for OTC deficiency and long-term therapy involves life-long restriction of protein intake and nitrogen scavenger therapy (with sodium phenyl acetate or sodium phenyl butyrate and/or sodium benzoate). Liver transplantation may also be considered in patients with severe, neonatal-onset OTC deficiency (usually performed by 6 months of age) or those with frequent hyperammonemic episodes.

SUMMARY OF THE INVENTION

The present invention provides, among other things, improved methods and compositions for treatment of ornithine transcarbamylase (OTC) deficiency. The invention is based in part on the unexpected discovery that surprisingly low amounts of an mRNA can be administered to a subject using the methods of the invention to obtain a therapeutically beneficial outcome. For example, therapeutically effective levels of OTC protein expression in vivo can be achieved by administering a surprisingly low amounts of OTC mRNA. Consequently, efficacy associated with low doses of the mRNA composition can provide the advantage of a wide therapeutic index for the composition. The low efficacious doses of OTC mRNA in a wide therapeutic index provide for a significant safety margin, which can be advantageous for treating certain patient groups, such as pediatric subjects and in particular children. The methods of the invention provide among other things, a longer time interval for therapeutic administration. The invention provides a therapeutic mRNA composition and methods for administration, resulting in highly efficient and sustained protein production in vivo and successful reduction of, for example, ammonia accumulation in blood, orotic acid levels in urine, and/or any clinically relevant disease marker.

In one aspect, the present invention provides a method of treating ornithine transcarbamylase (OTC) deficiency in a human, the method comprising administering to a human in need of treatment a pharmaceutical composition comprising an mRNA encoding an ornithine transcarbamylase protein formulated in a lipid nanoparticle at a therapeutic low dose of 0.5 mg/kg or less of mRNA and at a dosing interval of once every two weeks or at a longer dosing internal for a period sufficient to treat at least one symptom, or reduce the level of a biomarker associated with ornithine transcarbamylase deficiency in the human relative to a control.

In some embodiments, the therapeutic low dose is 0.4 mg/kg or less, or 0.3 mg/kg or less, or 0.2 mg/kg or less, or 0.15 mg/kg less, or 0.10 mg/kg or less, or 0.05 mg/kg or less, or 0.01 mg/kg or less, of mRNA encoding ornithine transcarbamylase protein.

In some embodiments, the therapeutic low dose is 0.3 mg/kg of mRNA or less. In some embodiments, the therapeutic low dose is 0.15 mg/kg of mRNA or less. In some embodiments, the therapeutic low dose is 0.001 mg/kg of mRNA or higher. In some embodiments, the therapeutic low dose is 0.005 mg/kg of mRNA or higher. In some embodiments, the low dose is 0.005 mg/kg mRNA encoding ornithine transcarbamylase protein. In certain embodiments, the therapeutic low dose is between 0.005 mg/kg and 0.3 mg/kg of mRNA. In certain embodiments, the therapeutic low dose is between 0.008 mg/kg and 0.2 mg/kg of mRNA. In certain embodiments, the therapeutic low dose is between 0.008 mg/kg and 0.12 mg/kg of mRNA. In certain embodiments, the therapeutic low dose is between 0.01 mg/kg and 0.10 mg/kg of mRNA. In certain embodiments, the therapeutic low dose is 0.01 mg/kg of mRNA. In certain embodiments, the therapeutic low dose is 0.02 mg/kg of mRNA. In certain embodiments, the therapeutic low dose is 0.03 mg/kg of mRNA. In certain embodiments, the therapeutic low dose is 0.04 mg/kg of mRNA. In certain embodiments, the therapeutic low dose is 0.05 mg/kg of mRNA. In certain embodiments, the therapeutic low dose is 0.06 mg/kg of mRNA. In certain embodiments, the therapeutic low dose is 0.07 mg/kg of mRNA. In certain embodiments, the therapeutic low dose is 0.08 mg/kg of mRNA. In certain embodiments, the therapeutic low dose is 0.09 mg/kg of mRNA. In certain embodiments, the therapeutic low dose is 0.10 mg/kg of mRNA.

In some embodiments, the longer dosing interval is once every two weeks or longer, once every three weeks or longer, or once every 4 weeks or longer. In some embodiments, the longer dosing interval is once every two weeks or longer. In some embodiments, the longer dosing interval is once every three weeks or longer. In some embodiments, the longer dosing interval is once every four weeks or longer.

In some embodiments, the mRNA is codon optimized.

In some embodiments, the symptom comprises hyperammonemia.

In some embodiments, the biomarker is selected from the group consisting of: high plasma ammonia level, high tissue ammonia level, urinary orotic acid, citrulline, serum glutamate, brain myoinositol, serum amino acids, and combination thereof. In some embodiments, the control is the baseline symptom or level prior to the treatment.

In some embodiments, the mRNA is administered for the period of at least two weeks, at least a month, at least two months, at least three months, at least four months, at least five months, at least six months or at least a year.

In one aspect, the invention provides a method of treating OTC deficiency in a human comprising: administering a pharmaceutical composition comprising an mRNA encoding an ornithine transcarbamylase protein at a therapeutic low dose of 0.5 mg/kg or less of mRNA and at a dosing interval of once every two weeks or a longer dosing interval, thereby to reduce an ammonia level relative to a control level prior to the treatment for the period of the dosing interval or longer. In some embodiments, the therapeutic low dose is 0.4 mg/kg or less, or 0.3 mg/kg or less, or 0.2 mg/kg or less, or 0.15 mg/kg less, or 0.10 mg/kg or less, or 0.05 mg/kg or less, or 0.01 mg/kg or less, of mRNA encoding ornithine transcarbamylase protein. In some embodiments, the therapeutic low dose is 0.3 mg/kg of mRNA or less. In some embodiments, the therapeutic low dose is 0.15 mg/kg of mRNA or less. In some embodiments, the therapeutic low dose is 0.001 mg/kg of mRNA or higher. In some embodiments, the therapeutic low dose is 0.005 mg/kg of mRNA or higher. In some embodiments, the low dose is 0.005 mg/kg mRNA encoding ornithine transcarbamylase protein.

In some embodiments, the therapeutic low dose is sufficient to maintain the reduced ammonia level in a tissue or a body fluid of the human for the period of the dosing interval or longer.

In some embodiments, a single administration of the pharmaceutical composition is sufficient to reduce and maintain the ammonia level in the tissue or the body fluid of the human to a level less than the level prior to the treatment for 3 weeks or longer.

In some embodiments, the single administration of the pharmaceutical composition is sufficient to reduce and maintain the ammonia level in the tissue or the body fluid of the human to level less than the level prior to the treatment for 4 weeks or longer.

In some embodiments, the mRNA is codon optimized.

In some embodiments, the mRNA is formulated in a lipid nanoparticle. In some embodiments, the mRNA is encapsulated in the lipid nanoparticle. In some embodiments, the lipid nanoparticle comprises one or more cationic lipids. In some embodiments, the one or more cationic lipids are selected from the group consisting of C12-200, MC3, DLinDMA, DLinkC2DMA, cKK-E12 (ML2), ICE (Imidazole-based), HGT5000, HGT5001, OF-02, DODAC, DDAB, DMRIE, DOSPA, DOTMA, DOGS, DODAP, DODMA and DMDMA, DODAC, DLenDMA, DMRIE, CLinDMA, CpLinDMA, DMOBA, DOcarbDAP, DLin-DAP, DLincarbDAP, DLinCDAP, KLin-K-DMA, DLin-K-XTC2-DMA, ALNY-100, NC98-5, HGT4003, aminolipids, DLin-MC3-DMA (MC3), (13Z, 16Z)—N,N-dimethyl-3-nonyldocosa-13,16-dien-1-amine (L608), KL22, KL25, KL10, 1,2-dilinoleyloxy-N,N-dimethylaminopropane (DLin-DMA) and combinations thereof. In some embodiments, the lipid nanoparticle comprises one or more non-cationic lipids. In some embodiments, the one or more non-cationic lipids are selected from the group consisting of DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (2-dioleoyl-sn-glycero-3-phospho-(1'-rac-glycerol)) and combinations thereof. In some embodiments, the cationic lipid is (3S,6R)-3,6-bis(4-(bis((R)-2-hydroxydodecyl)amino)butyl)piperazine-2,5-dione).

In some embodiments, the lipid nanoparticle comprises one or more PEGylated lipids.

In some embodiments, the one or more PEGylated lipids comprises a poly(ethylene) glycol chain of up to 5 kDa in length covalently attached to a lipid comprising one or more alkyl chains of C6-C20 in length. In some embodiments, the PEG-lipid is 1,2-dimyristoyl-rac-glycero-3-methylpolyoxyethylene (DMG-PEG-2K).

In some embodiments, the pharmaceutical composition further comprises one or more excipients.

In some embodiments, the mRNA comprises one or more modified nucleotides. In some embodiments, the one or more modified nucleotides are selected from pseudouridine, N-1-methyl-pseudouridine, 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and/or 2-thiocytidine. In some embodiments, the administering of the pharmaceutical composition is performed intravenously.

In some embodiments, the body fluid is serum. In some embodiments, the body fluid is blood plasma. In some embodiments, administering the pharmaceutical composition reduces and maintains the plasma ammonia level of the human at less than 1,000 micromol/L. In some embodiments, administering the pharmaceutical composition reduces an orotic acid level in the urine. In some embodiments, the orotic acid level in the urine is reduced to less than 1.5 mmol/mol creatinine. In some embodiments, administering the pharmaceutical composition increases a plasma citrulline level relative to the baseline level prior to the treatment. In some embodiments, the plasma citrulline level is increased to greater than 10 µM. In some embodiments, the administering the pharmaceutical composition reduces a plasma glutamate level relative to the baseline level prior to the treatment.

In some embodiments, the mRNA is administered concurrently with an additional therapy. In some embodiments, the additional therapy is selected from the following: administering sodium phenylacetate, administering sodium phenylbutyrate, administering benzoate, administering arginine hydrochloride, administering amino acid supplement and dietary protein intake restriction.

In some embodiments the administration of the mRNA composition has a high tolerance and safety profile as determined by lack of adverse effects in subjects following the administration. In some embodiments the adverse effect is an at least 2-fold elevation in liver enzyme AST levels above baseline for a subject. In some embodiments the adverse effect is denoted by at least 2-fold elevation in liver enzyme ALT levels above baseline for a subject. In some embodiments, the baseline AST or the baseline ALT is a corresponding value of the respective liver enzyme level in the subject prior to the first administration of the mRNA composition. In some embodiments the adverse effect is an infusion related reaction. In some embodiments the infusion related reaction is any one or more symptoms from a group consisting of: arthralgia (joint pain), bronchospasm, cough, dizziness, dyspnea (shortness of breath), fatigue (asthenia, lethargy, malaise), fever, headache, hypertension, hypotension, myalgia (muscle pain), nausea, pruritus/itching, rash/desquamation, rigors/chills, sweating (diaphoresis), tachycardia, urticaria (hives, welts, wheals), and vomiting.

In some embodiments the adverse effect is an immune reaction.

The method of any one of the preceding claims wherein the administration results in distribution of the mRNA to the liver.

In some embodiments the mRNA is administered concurrently with an additional therapy.

In another aspect, the present invention provides a method of diagnosing ornithine transcarbamylase (OTC) deficiency in a human, the method comprising administering to a human a single administration of a pharmaceutical composition comprising an mRNA encoding an ornithine transcarbamylase protein formulated in a lipid nanoparticle and assessing if one or more symptoms and/or one or more biomarkers associated with ornithine transcarbamylase deficiency in the human is alleviated or reduced. In certain embodiments, the human has a genetic mutation outside the coding region for OTC protein that causes OTC deficiency. In certain embodiments, the human has a genetic mutation adjacent to the coding region for OTC protein that causes OTC deficiency.

In some embodiments, the method comprises administering to a human a single administration of a pharmaceutical composition comprising an mRNA encoding an ornithine transcarbamylase protein formulated in a lipid nanoparticle and assessing if one or more symptoms associated with ornithine transcarbamylase deficiency is alleviated or reduced. In certain embodiments, the symptom is high plasma ammonia level. In certain embodiments, the reduced high plasma ammonia level is determined relative to the human's plasma ammonia level prior to administration of the pharmaceutical composition comprising an mRNA encoding an ornithine transcarbamylase protein formulated in a lipid nanoparticle. In certain embodiments, the reduced high plasma ammonia level is determined relative to reduction in plasma ammonia level in a control.

In some embodiments, the method comprises administering to a human a single administration of a pharmaceutical composition comprising an mRNA encoding an ornithine transcarbamylase protein formulated in a lipid nanoparticle and assessing if one or more biomarker levels associated with ornithine transcarbamylase deficiency is reduced. In certain embodiments, the biomarker level(s) is selected from the group consisting of plasma ammonia level, tissue ammonia level, urinary orotic acid level, citrulline level, serum glutamate level, brain myoinositol level, serum amino acid levels, or combinations thereof. In certain embodiments, the biomarker is plasma ammonia level. In certain embodiments, the biomarker is tissue ammonia level. In certain embodiments, the biomarker is urinary orotic acid level. In certain embodiments, the biomarker is citrulline level. In certain embodiments, the biomarker is serum glutamate level. In certain embodiments, the biomarker is a serum amino acid level. In certain embodiments, the reduced biomarker level is determined relative to the human's biomarker level prior to administration of the pharmaceutical composition comprising an mRNA encoding an ornithine transcarbamylase protein formulated in a lipid nanoparticle. In certain embodiments, the reduced biomarker level is determined relative to reduction in the biomarker level in a control.

In some embodiments, the dose administered in a pharmaceutical composition comprising the mRNA encoding an ornithine transcarbamylase protein formulated in a lipid nanoparticle to the human to assess if one or more symptoms associated with ornithine transcarbamylase deficiency is alleviated or reduced is between 0.005 mg/kg and 0.3 mg/kg of mRNA. In certain embodiments, the dose is between 0.008 mg/kg and 0.2 mg/kg of mRNA. In certain embodiments, the dose is between 0.008 mg/kg and 0.12 mg/kg of mRNA. In certain embodiments, the dose is between 0.01 mg/kg and 0.10 mg/kg of mRNA. In certain embodiments, the dose is 0.01 mg/kg of mRNA. In certain embodiments, the dose is 0.02 mg/kg of mRNA. In certain embodiments, the dose is 0.03 mg/kg of mRNA. In certain embodiments, the dose is 0.04 mg/kg of mRNA. In certain embodiments, the dose is 0.05 mg/kg of mRNA. In certain embodiments, the dose is 0.06 mg/kg of mRNA. In certain embodiments, the dose is 0.07 mg/kg of mRNA. In certain embodiments, the dose is 0.08 mg/kg of mRNA. In certain embodiments, the dose is 0.09 mg/kg of mRNA. In certain embodiments, the dose is 0.10 mg/kg of mRNA.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only not for limitation.

DEFINITIONS

Figure 1:
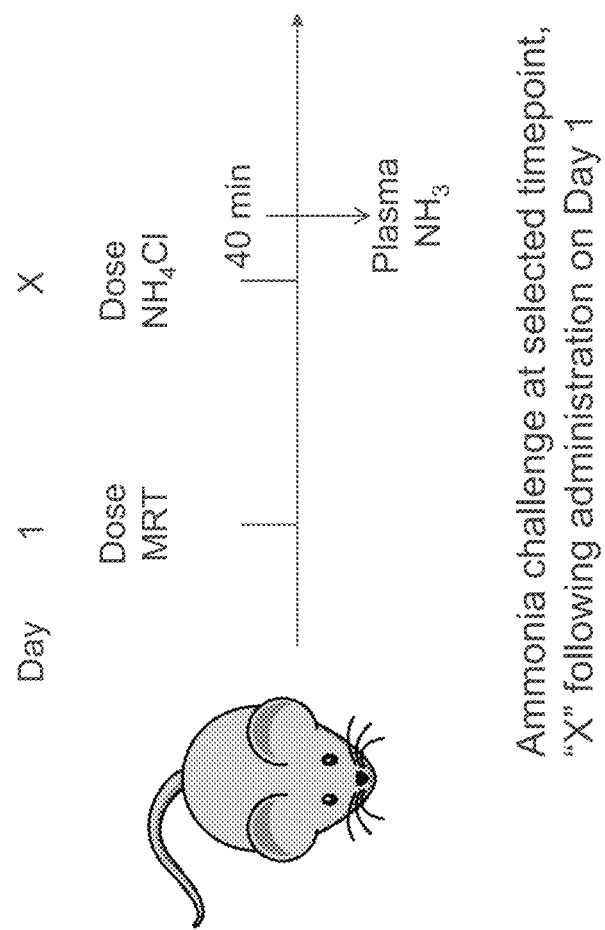
FIG. 1 is a schematic diagram that outlines a test set up for monitoring the ability of hOTC protein produced from hOTC mRNA to reduce plasma ammonia levels thereby reducing and/or maintaining the reduction of hyperammonemia.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Alkyl: As used herein, "alkyl" refers to a radical of a straight-chain or branched saturated hydrocarbon group having from 1 to 15 carbon atoms ("$C_{1-15}$ alkyl"). In some embodiments, an alkyl group has 1 to 3 carbon atoms ("$C_{1-3}$ alkyl"). Examples of $C_{1-3}$ alkyl groups include methyl ($C_1$), ethyl ($C_2$), n-propyl ($C_3$), and isopropyl ($C_3$). In some embodiments, an alkyl group has 8 to 12 carbon atoms ("$C_{8-12}$ alkyl"). Examples of $C_{8-12}$ alkyl groups include, without limitation, n-octyl ($C_8$), n-nonyl ($C_9$), n-decyl ($C_{10}$), n-undecyl ($C_{11}$), n-dodecyl ($C_{12}$) and the like. The prefix "n-" (normal) refers to unbranched alkyl groups. For example, n-$C_8$ alkyl refers to —$(CH_2)_7CH_3$, n-$C_{10}$ alkyl refers to —$(CH_2)_9CH_3$, etc.

Amino acid: As used herein, term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"). Other exemplary situations include one in which an mRNA is delivered to a target tissue and the encoded protein is expressed and secreted into patient's circulation system (e.g., serum) and systematically distributed and taken up by other tissues (also referred to as "systemic distribution" or "systemic delivery"). In other exemplary situations, the mRNA is delivered systemically and is taken up in a wide variety of cells and tissues in vivo. In some exemplary situations, the delivery is intravenous, intramuscular or subcutaneous.

Dosing interval: As used herein dosing interval in the context of a method for treating a disease is the frequency of administering a therapeutic composition in a subject (mammal) in need thereof, for example an mRNA composition, at an effective dose of the mRNA, such that one or more symptoms associated with the disease is reduced; or one or more biomarkers associated with the disease is reduced, at least for the period of the dosing interval. Dosing frequency and dosing interval may be used interchangeably in the current disclosure.

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Effective dose: As used herein, an effective dose is a dose of the mRNA in the pharmaceutical composition which when administered to the subject in need thereof, hereby a mammalian subject, according to the methods of the invention, is effective to bring about an expected outcome in the subject, for example reduce a symptom associated with the disease.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

Messenger RNA (mRNA): As used herein, the term "messenger RNA (mRNA)" refers to a polyribonucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, in vitro transcribed, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolopyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid. As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quaternization of an amine using an appropriate electrophile, e.g., an alkyl halide, to form a quarternized alkylated amino salt.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, improved methods and compositions for treating ornithine transcarbamylase (OTC) deficiency based on mRNA therapy. Messenger RNA therapy is a safe and effective mode of introducing a genetic material which can stably produce the encoded protein in vivo for a period of time. The method of treatment encompasses administering to a subject in need of treatment an improved composition comprising an mRNA encoding ornithine transcarbamylase (OTC) at an effective dose and an administration interval such that at least one symptom or feature of OTC deficiency is reduced in intensity, severity, or frequency or has a delayed onset.

In one aspect, the invention provides a composition comprising a codon optimized OTC mRNA, and a lipid formulation for improved delivery of the mRNA and sustained in vivo function, such that at least one symptom or feature of OTC deficiency is reduced in intensity, severity, or frequency or has a delayed onset. In some embodiments, the mRNA is not codon optimized. OTC deficiency symptom is marked by increased accumulation of ammonia in the tissues and serum of the patient, a condition known as hyperammonemia. The present invention further provides methods of treating OTC deficiency comprising administering to a subject in need of treatment a therapeutically effective amount of a composition comprising an mRNA encoding acid OTC such that hyperammonemia in the subject is treated. In some embodiments, the mRNA is encapsulated within one or more liposomes. As used herein, the term "liposome" refers to any lamellar, multilamellar, or solid nanoparticle vesicle. Typically, a liposome as used herein can be formed by mixing one or more lipids or by mixing one or more lipids and polymer(s). Thus, the term "liposome" as used herein encompasses both lipid and polymer-based nanoparticles. In some embodiments, a liposome suitable for the present invention contains cationic or non-cationic lipid(s), cholesterol-based lipid(s) and PEG-modified lipid(s).

Ornithine Transcarbamylase (OTC) Deficiency

OTC deficiency is a urea cycle disrupting disease, specifically, an X-linked monogenic disorder characterized by mutations in the gene for the enzyme ornithine transcarbamylase (OTC). The OTC enzyme is also known as ornithine carbamoyltransferase, mitochondrial. The OTC gene is also known as: MGC129967, MGC129968, OCTD, ornithine carbamoyltransferase precursor, ornithine transcarbamylase, and OTC_HUMAN. More than 300 mutations that cause OTC deficiency have been identified in the OTC gene. Many of the mutations in the OTC gene likely affect the structure of the resulting protein and decrease its activity. Some genetic mutations that cause OTC deficiency may appear outside the coding sequence for OTC deficiency. Such mutations typically cannot be diagnosed by sequencing a patients OTC protein, endogenous OTC mRNA, or endogenous gene coding for OTC protein. In such cases, ex juvantibus methods for diagnosing OTC deficiency as described herein may be used.

Mutations in or relating to the OTC gene eliminate or reduce the ability of the OTC enzyme catalyze the synthesis of citrulline (in the liver and small intestine) from carbamoyl phosphate and ornithine. As a result, excess nitrogen, in the form of ammonia, accumulates in the blood, and travels to the nervous system, resulting in the symptoms associated with OTC deficiency. The accumulation of ammonia can lead to brain damage and death. Mutations that abolish OTC activity completely result in the severe, neonatal-onset form while mutations leading to decreased OTC activity result in the late-onset phenotypes.

Ornithine Transcarbamylase (OTC) Diagnosis

In many instances, OTC deficiency may be diagnosed through by sequencing a patients OTC protein, endogenous OTC mRNA, or endogenous gene coding for OTC protein. However, ex juvantibus methods for diagnosing OTC deficiency as described herein, optionally using compositions as described herein, may be used as alternatives to sequencing and in addition to sequencing and/or clinical observation. These ex juvantibus methods are particularly useful for patients suffering from OTC deficiency who have a genetic mutation that causes OTC deficiency but is outside the coding sequence for OTC protein. Accordingly, the present invention provides ex juvantibus methods for diagnosing ornithine transcarbamylase (OTC) deficiency in a patient suspected of having OTC deficiency, wherein the patient is administered a pharmaceutical composition comprising an mRNA encoding an ornithine transcarbamylase protein formulated in a lipid nanoparticle. Then the patient is assessed for an alleviation or reduction in one or more symptoms and/or one or more biomarkers associated with ornithine transcarbamylase deficiency. In certain embodiments, the patient has a genetic mutation outside the coding region for OTC protein that causes OTC deficiency. In certain embodiments, the patient has a genetic mutation adjacent to the coding region for OTC protein that causes OTC deficiency.

In some embodiments, the ex juvantibus methods comprise administering to a patient suspected of having OTC deficiency a pharmaceutical composition comprising an mRNA encoding an ornithine transcarbamylase protein formulated in a lipid nanoparticle and one or more symptoms associated with ornithine transcarbamylase deficiency is assessed. In certain embodiments, the symptom is high plasma ammonia level. In certain embodiments, OTC deficiency is diagnosed if the high plasma ammonia level is reduced by a determined amount relative to the patient's plasma ammonia level prior to administration of the pharmaceutical composition. In certain embodiments, OTC deficiency is diagnosed if the high plasma ammonia level is reduced relative to a control. In certain embodiments, OTC deficiency is diagnosed if the high plasma ammonia level is reduced relative to a predetermined value.

In some embodiments, the ex juvantibus methods comprise administering to a patient a pharmaceutical composition comprising an mRNA encoding an ornithine transcarbamylase protein formulated in a lipid nanoparticle and one or more biomarker levels associated with ornithine transcarbamylase deficiency is reduced. The biomarker level(s) can include one or more of plasma ammonia level, tissue ammonia level, urinary orotic acid level, citrulline level, serum glutamate level, brain myoinositol level, serum amino acid levels, or a combination thereof. In certain embodiments, OTC deficiency is diagnosed if one or more biomarker levels is reduced by a determined amount relative to the patient's corresponding biomarker level(s) prior to administration of the pharmaceutical composition. In certain embodiments, the OTC deficiency is diagnosed if one or more biomarker levels is reduced relative to a control. In certain embodiments, the OTC deficiency is diagnosed if one or more biomarker levels is reduced relative to a predetermined value for the corresponding biomarkers.

In some embodiments, the dose administered in a pharmaceutical composition comprising the mRNA encoding an ornithine transcarbamylase protein formulated in a lipid nanoparticle to the human for diagnosing a patient with OTC deficiency is between 0.005 mg/kg and 0.3 mg/kg of mRNA. In certain embodiments, the dose is between 0.008 mg/kg and 0.2 mg/kg of mRNA. In certain embodiments, the dose is between 0.008 mg/kg and 0.12 mg/kg of mRNA. In certain embodiments, the dose is between 0.01 mg/kg and 0.10 mg/kg of mRNA. In certain embodiments, the dose is 0.01 mg/kg of mRNA. In certain embodiments, the dose is 0.02 mg/kg of mRNA. In certain embodiments, the dose is 0.03 mg/kg of mRNA. In certain embodiments, the dose is 0.04 mg/kg of mRNA. In certain embodiments, the dose is 0.05 mg/kg of mRNA. In certain embodiments, the dose is 0.06 mg/kg of mRNA. In certain embodiments, the dose is 0.07 mg/kg of mRNA. In certain embodiments, the dose is 0.08 mg/kg of mRNA. In certain embodiments, the dose is 0.09 mg/kg of mRNA. In certain embodiments, the dose is 0.10 mg/kg of mRNA.

Ornithine Transcarbamylase (OTC) Gene and Protein Sequence

In some embodiments, the present invention provides methods and compositions for delivering mRNA encoding OTC to a subject for the treatment of OTC deficiency. A suitable OTC mRNA encodes any full length, fragment or portion of an OTC protein which can be substituted for naturally-occurring OTC protein activity and/or reduce the intensity, severity, and/or frequency of one or more symptoms associated with OTC deficiency.

In some embodiments, a suitable mRNA sequence is an mRNA sequence encoding a human OTC protein. The naturally-occurring human OTC mRNA coding sequence and the corresponding amino acid sequence are shown in Table 1:

TABLE 1

Human OTC

| | |
|---|---|
| Human OTC (mRNA coding sequence) | (SEQ ID NO: 1)<br>AUGCUGUUUAAUCUGAGGAUCCUGUUAAACAAUGCAGCUUUUAGAAA<br>UGGUCACAACUUCAUGGUUCGAAAUUUUCGGUGUGGACAACCACUAC<br>AAAAUAAAGUGCAGCUGAAGGGCCGUGACCUUCUCACUCUAAAAAAC<br>UUUACCGGAGAAGAAAUUAAAUAUAUGCUAUGGCUAUCAGCAGAUCU<br>GAAAUUUAGGAUAAAACAGAAAGGAGAGUAUUUGCCUUUAUUGCAAG<br>GGAAGUCCUUAGGCAUGAUUUUUGAGAAAAGAAGUACUCGAACAAGA<br>UUGUCUACAGAAACAGGCUUUGCACUUCUGGGAGGACAUCCUUGUUU<br>UCUUACCACACAAGAUAUUCAUUUGGGUGUGAAUGAAAGUCUCACGG<br>ACACGGCCCGUGUAUUGUCUAGCAUGGCAGAUGCAGUAUUGGCUCGA<br>GUGUAUAAACAAUCAGAUUUGGACACCCUGGCUAAAGAAGCAUCCAU<br>CCCAAUUAUCAAUGGGCUGUCAGAUUUGUACCAUCCUAUCCAGAUCCU<br>GGCUGAUUACCUCACGCUCCAGGAACACUAUAGCUCUCUGAAAGGUCU<br>UACCCUCAGCUGGAUCGGGGAUGGGAACAAUAUCCUGCACUCCAUCAU<br>GAUGAGCGCAGCGAAAUUCGGAAUGCACCUUCAGGCAGCUACUCCAAA<br>GGGUUAUGAGCCGGAUGCUAGUGUAACCAAGUUGGCAGAGCAGUAUG<br>CCAAAGAGAAUGGUACCAAGCUGUUGCUGACAAAUGAUCCAUUGGAA<br>GCAGCGCAUGGAGGCAAUGUAUUAAUUACAGACACUUGGAUAAGCAU<br>GGGACAAGAAGAGGAGAAGAAAAAGCGGCUCCAGGCUUUCCAAGGUU<br>ACCAGGUUACAAUGAAGACUGCUAAAGUUGCUGCCUCUGACUGGACA |

TABLE 1-continued

Human OTC

| | |
|---|---|
| | UUUUUACACUGCUUGCCCAGAAAGCCAGAAGAAGUGGAUGAUGAAGU<br>CUUUUAUUCUCCUCGAUCACUAGUGUUCCCAGAGGCAGAAAACAGAA<br>AGUGGACAAUCAUGGCUGUCAUGGUGUCCCUGCUGACAGAUUACUCA<br>CCUCAGCUCCAGAAGCCUAAAUUUUGA |
| Human<br>OTC<br>(DNA<br>Sequence) | (SEQ ID NO: 2)<br>ATGCTGTTTAATCTGAGGATCCTGTTAAACAATGCAGCTTTTAGAAATGG<br>TCACAACTTCATGGTTCGAAATTTTCGGTGTGGACAACCACTACAAAATA<br>AAGTGCAGCTGAAGGGCCGTGACCTTCTCACTCTAAAAAACTTTACCGG<br>AGAAGAAATTAAATATATGCTATGGCTATCAGCAGATCTGAAATTTAGG<br>ATAAAACAGAAAGGAGAGTATTTGCCTTTATTGCAAGGGAAGTCCTTAG<br>GCATGATTTTTGAGAAAAGAAGTACTCGAACAAGATTGTCTACAGAAAC<br>AGGCTTTGCACTTCTGGGAGGACATCCTTGTTTTCTTACCACACAAGATA<br>TTCATTTGGGTGTGAATGAAAGTCTCACGGACACGGCCCGTGTATTGTCT<br>AGCATGGCAGATGCAGTATTGGCTCGAGTGTATAAACAATCAGATTTGG<br>ACACCCTGGCTAAAGAAGCATCCATCCCAATTATCAATGGGCTGTCAGA<br>TTTGTACCATCCTATCCAGATCCTGGCTGATTACCTCACGCTCCAGGAC<br>ACTATAGCTCTCTGAAAGGTCTTACCCTCAGCTGGATCGGGGATGGGAA<br>CAATATCCTGCACTCCATCATGATGAGCGCAGCGAAATTCGGAATGCAC<br>CTTCAGGCAGCTACTCCAAAGGGTTATGAGCCGGATGCTAGTGTAACCA<br>AGTTGGCAGAGCAGTATGCCAAAGAGAATGGTACCAAGCTGTTGCTGAC<br>AAATGATCCATTGGAAGCAGCGCATGGAGGCAATGTATTAATTACAGAC<br>ACTTGGATAAGCATGGGACAAGAAGAGGAGAAGAAAAAGCGGCTCCAG<br>GCTTTCCAAGGTTACCAGGTTACAATGAAGACTGCTAAAGTTGCTGCCTC<br>TGACTGGACATTTTTACACTGCTTGCCCAGAAAGCCAGAAGAAGTGGAT<br>GATGAAGTCTTTTATTCTCCTCGATCACTAGTGTTCCCAGAGGCAGAAAA<br>CAGAAAGTGGACAATCATGGCTGTCATGGTGTCCCTGCTGACAGATTAC<br>TCACCTCAGCTCCAGAAGCCTAAATTTTGA |
| Human<br>OTC<br>Protein<br>Sequence | (SEQ ID NO: 3)<br>MLFNLRILLNNAAFRNGHNFMVRNFRCGQPLQNKVQLKGRDLLTLKNFTG<br>EEIKYMLWLSADLKFRIKQKGEYLPLLQGKSLGMIFEKRSTRTRLSTETGFA<br>LLGGHPCFLTTQDIHLGVNESLTDTARVLSSMADAVLARVYKQSDLDTLAK<br>EASIPIINGLSDLYHPIQILADYLTLQEHYSSLKGLTLSWIGDGNNILHSIMMS<br>AAKFGMHLQAATPKGYEPDASVTKLAEQYAKENGTKLLLTNDPLEAAHGG<br>NVLITDTWISMGQEEEKKKRLQAFQGYQVTMKTAKVAASDWTFLHCLPRK<br>PEEVDDEVFYSPRSLVFPEAENRKWTIMAVMVSLLTDYSPQLQKPKF |

In some embodiments, a suitable mRNA is a wild-type human OTC mRNA of sequence (SEQ ID NO: 1). In some embodiments, a suitable therapeutic candidate mRNA may be a codon optimized hOTC sequence that can encode an OTC amino acid sequence shown in Table 1 as SEQ ID NO: 3 or an amino acid sequence at least 70%, 75%, 80%, 85%, 90%, 95%, 96%, 97%, 98%, or 99% identical to SEQ ID NO: 3.

Exemplary Suitable Codon Optimized OTC mRNA Sequences

In some embodiments, a suitable mRNA may be a codon optimized sequence as shown in SEQ ID NO: 4:

(SEQ ID NO: 4)
AUGCUGUUCAACCUGAGAAUCCUGCUGAACAACGCCGCCUUCAGAAACGG

CCACAACUUCAUGGUGAGAAACUUCAGAUGCGGCCAGCCCCUGCAGAACA

AGGUGCAGCUGAAGGGCAGAGACCUGCUGACCCUGAAGAACUUCACCGGC

GAGGAGAUCAAGUACAUGCUGUGGCUGAGCGCCGACCUGAAGUUCAGAAU

CAAGCAGAAGGGCGAGUACCUGCCCCUGCUGCAGGGCAAGAGCCUGGGCA

UGAUCUUCGAGAAGAGAAGCACCAGAACCAGACUGAGCACCGAGACCGGC

UUCGCCCUGCUGGGCGGCCACCCCUGCUUCCUGACCACCCAGGACAUCCA

CCUGGGCGUGAACGAGAGCCUGACCGACACCGCCAGAGUGCUGAGCAGCA

UGGCCGACGCCGUGCUGGCCAGAGUGUACAAGCAGAGCGACCUGGACACC

CUGGCCAAGGAGGCCAGCAUCCCCAUCAUCAACGGCCUGAGCGACCUGUA

CCACCCCAUCCAGAUCCUGGCCGACUACCUGACCCUGCAGGAGCACUACA

GCAGCCUGAAGGGCCUGACCCUGAGCUGGAUCGGCGACGGCAACAACAUC

CUGCACAGCAUCAUGAUGAGCGCCGCCAAGUUCGGCAUGCACCUGCAGGC

CGCCACCCCCAAGGGCUACGAGCCCGACGCCAGCGUGACCAAGCUGGCCG

AGCAGUACGCCAAGGAGAACGGCACCAAGCUGCUGCUGACCAACGACCCC

CUGGAGGCCGCCCACGGCGGCAACGUGCUGAUCACCGACACCUGGAUCAG

CAUGGGCCAGGAGGAGGAGAAGAAGAAGAGACUGCAGGCCUUCCAGGGCU

ACCAGGUGACCAUGAAGACCGCCAAGGUGGCCGCCAGCGACUGGACCUUC

CUGCACUGCCUGCCCAGAAAGCCCGAGGAGGUGGACGACGAGGUGUUCUA

CAGCCCCAGAAGCCUGGUGUUCCCCGAGGCCGAGAACAGAAAGUGGACCA

UCAUGGCCGUGAUGGUGAGCCUGCUGACCGACUACAGCCCCCAGCUGCAG

AAGCCCAAGUUCUGA

In some embodiments, a suitable mRNA may be a codon optimized sequence as shown in SEQ ID NO: 5:

(SEQ ID NO: 5)
AUGCUGUUCAACCUUCGGAUCUUGCUGAACAACGCUGCGUUCCGGAAUGG

UCACAACUUCAUGGUCCGGAACUUCAGAUGCGGCCAGCCGCUCCAGAACA

AGGUGCAGCUCAAGGGGAGGGACCUCCUCACCCUGAAAAACUUCACCGGA

GAAGAGAUCAAGUACAUGCUGUGGCUGUCAGCCGACCUCAAAUUCCGGAU

CAAGCAGAAGGGCGAAUACCUUCCUUUGCUGCAGGGAAAGUCCCUGGGGA

UGAUCUUCGAGAAGCGCAGCACUCGCACUAGACUGUCAACUGAAACCGGC

UUCGCGCUGCUGGGAGGACACCCCUGCUUCCUGACCACCCAAGAUAUCCA

UCUGGGUGUGAACGAAUCCCUCACCGACACAGCGCGGGUGCUGUCGUCCA

UGGCAGACGCGGUCCUCGCCCGCGUGUACAAGCAGUCUGAUCUGGACACU

CUGGCCAAGGAAGCCUCCAUUCCUAUCAUUAAUGGAUUGUCCGACCUCUA

CCAUCCCAUCCAGAUUCUGGCCGAUUAUCUGACUCUGCAAGAACAUUACA

GCUCCCUGAAGGGGCUUACCCUUUCGUGGAUCGGCGACGGCAACAACAUU

CUGCACAGCAUUAUGAUGAGCGCUGCCAAGUUUGGAAUGCACCUCCAAGC

AGCGACCCCGAAGGGAUACGAGCCAGACGCCUCCGUGACGAAGCUGGCUG

AGCAGUACGCCAAGGAGAACGGCACUAAGCUGCUGCUCACCAACGACCCU

CUCGAAGCCGCCCACGGUGGCAACGUGCUGAUCACCGAUACCUGGAUCUC

CAUGGGACAGGAGGAGGAAAAGAAGAAGCCGCCUGCAAGCAUUUCAGGGGU

ACCAGGUGACUAUGAAAACCGCCAAGGUCGCCGCCUCGGACUGGACCUUC

UUGCACUGUCUGCCCAGAAAGCCCGAAGAGGUGGACGACGAGGUGUUCUA

CAGCCCGCGGUCGCUGGUCUUUCCGGAGGCCGAAAACAGGAAGUGGACUA

UCAUGGCCGUGAUGGUGUCCCUGCUGACCGAUUACUCCCCGCAGCUGCAG

AAACCAAAGUUCUGA

In some embodiments, a suitable mRNA may be a
codon optimized sequence as shown in SEQ ID NO: 6.
(SEQ ID NO: 6)
AUGCUUUUCAACCUGAGAAUUCUGCUGAACAACGCAGCCUUCCGCAACGG

ACACAACUUCAUGGUCCGGAACUUCAGAUGCGGACAACCGCUGCAGAACA

AGGUCCAGCUCAAGGGUCGGGACCUGUUGACUCUUAAGAAUUUCACCGGA

GAAGAAAUCAAGUACAUGCUGUGGCUGUCCGCCGACCUGAAGUUCGCAU

CAAGCAGAAGGGGGAGUACCUCCCCCUGCUGCAAGGAAAGUCCCUGGGAA

UGAUUUUCGAGAAGCGCUCCACCCGCACUAGACUUUCCACCGAAACCGGC

UUCGCUCUGCUGGGCGGACAUCCUUGCUUUCUGACGACUCAGGACAUCCA

CCUCGGAGUGAACGAAUCCCUCACCGAUACCGCCAGGGUGCUGAGCAGCA

UGGCCGACGCUGUGCUGGCUCGGGUGUACAAGCAGUCCGACCUCGACACC

CUGGCCAAGGAAGCCUCGAUCCCUAUCAUCAAUGGCCUGUCAGACCUGUA

CCACCCAAUCCAGAUUCUGGCCGACUACCUGACUCUCCAAGAGCACUACA

GCAGCCUCAAGGGGCUCACAUUGUCCUGGAUCGGCGACGGCAACAACAUC

CUUCACUCCAUUAUGAUGUCGGCCGCCAAAUUCGGGAUGCAUCUGCAGGC

AGCCACCCCUAAGGGAUACGAGCCCGAUGCCUCCGUGACCAAGCUCGCCG

AACAGUAUGCGAAGGAGAACGGCACCAAGCUCCUGCUCACUAACGAUCCG

UUGGAAGCUGCCCACGGCGGAAACGUGCUGAUUACCGACACCUGGAUCAG

CAUGGGGCAGGAAGAAGAGAAGAAGAAGCGGCUGCAGGCGUUUCAGGGUU

ACCAAGUCACCAUGAAAACUGCCAAAGUCGCGGCAUCCGACUGGACUUUC

CUGCACUGUCUGCCGAGGAAACCAGAGGAAGUGGAUGACGAAGUGUUCUA

CUCACCCCGGUCGCUGGUGUUCCGGAAGCGGAGAACCGGAAGUGGACCA

UCAUGGCCGUGAUGGUGUCGCUGCUCACCGAUUACUCUCCGCAACUGCAG

AAGCCCAAGUUCUGA

In some embodiments, a suitable mRNA may be a
codon optimized sequence as shown in SEQ ID NO: 7.
(SEQ ID NO: 7)
AUGCUGUUUAACCUGAGAAUUCUGCUGAACAACGCCGCGUUCAGGAACGG

CACAAUUUCAUGGUCCGCAACUUUAGAUGCGGACAGCCUCUCCAAAACAAG

GUCCAGCUCAAGGGGCGGGACUUGCUGACCCUUAAGAACUUUACCGGCGAA

GAGAUCAAGUACAUGCUGUGGUUGUCAGCGGACCUGAAGUUCCGCAUCAAG

CAGAAAGGGGAGUAUCUGCCGCUGCUCCAAGGAAAGUCGCUCGGCAUGAUC

UUCGAGAAGCGCUCGACCAGAACCCGGCUGUCCACUGAAACUGGUUUCGCC

CUUCUGGGUGGACACCCUUGUUUCCUGACAACCCAGGACAUCCAUCUGGGC

GUGAACGAAAGCCUCACUGACACCGCCAGGGUGCUGAGCUCCAUGGCCGAC

GCUGUCCUUGCCCGGGUGUACAAGCAGUCCGAUCUGGACACUCUGGCCAAG

GAAGCGUCCAUCCCGAUCAUUAACGGACUGUCCGACCUGUACCACCCGAUC

CAGAUUCUGGCCGACUACCUGACCUUGCAAGAGCACUACAGCUCACUGAAG

GGCUUGACCCUGAGCUGGAUCGGCGACGAAACAACAUUCUGCAUUCGAUC

AUGAUGUCCGCGGCCAAGUUCGGAAUGCAUCUGCAGGCCGCAACUCCCAAG

GGAUACGAACCUGAUGCGUCCGUGACUAAGCUGGCCGAGCAGUACGCAAAG

GAAAACGGCACCAAGCUGCUGCUGACCAACGACCCGCUCGAAGCUGCCCAC

GGAGGGAACGUGCUCAUUACCGACACUUGGAUCUCCAUGGGGCAGGAAGAA

GAGAAGAAGAAGCGGCUCCAGGCAUUCCAGGGUUACCAGGUCACCAUGAAA

ACGGCCAAAGUGGCCGCUUCGGAUUGGACUUUCCUCCACUGCCUUCCCGC

AAACCUGAGGAAGUGGAUGAUGAAGUGUUCUACUCCCCACGCUCCCUCGUG

UUCCCCGAGGCCGAGAAUCGGAAGUGGACCAUUAUGGCCGUGAUGGUGUCA

CUGCUGACCGACUACAGCCCCAACUGCAAAAGCCGAAGUUCUGA

In some embodiments, a suitable mRNA may be a
codon optimized sequence as shown in SEQ ID NO: 8.
(SEQ ID NO: 8)
AUGCUGUUCAACCUCCGGAUCCUCCUCAACAACGCCGCGUUCCGCAACGG

CCACAACUUCAUGGUCCGGAAUUUCCGAUGCGGACAGCCACUGCAGAACA

AGGUCCAGCUGAAGGGCCGGGACUUGCUGACUCUCAAGAACUUUACCGGG

GAAGAAAUCAGUACAUGCUGUGGCUUUCCGCCGACCUGAAGUUCAGAAU

CAAGCAGAAGGGCGAAUAUCUCCCCCUGCUGCAAGGAAAGAGCCUGGGCA

UGAUUUUCGAGAAGAGAUCGACACGCACCCGGCUGUCCACCGAGACUGGG

UUUGCCCUGCUGGGAGGACACCCGUGUUUCCUGACCACCCAAGAUAUCCA

UCUCGGAGUGAACGAAUCCCUUACUGACACUGCCCGCGUGUUGUCCUCCA

UGGCUGAUGCAGUGCUCGCUCGGGUGUACAAGCAGAGCGACCUGGACACU

CUGGCGAAGGAAGCCUCAAUUCCUAUCAUUAACGGGCUGUCGGACCUGUA

CCACCCGAUCCAGAUUCUGGCCGACUACCUGACCCUGCAAGAACACUACU

CAAGCCUGAAGGGUCUUACCCUGUCCUGGAUCGGCGACGGCAACAACAUC

CUGCACUCCAUCAUGAUGUCGGCCGCGAAGUUCGGAAUGCACCUCCAAGC

AGCGACUCCGAAGGGUUACGAGCCAGAUGCCUCCGUGACCAAGCUGGCGG

AGCAGUACGCUAAGGAAAACGGAACCAAGCUGCUGCUCACUAACGACCCG

UUGGAAGCCGCCCAUGGUGGAAAUGUGCUGAUCACGGAUACCUGGAUCAG

-continued
CAUGGGCCAGGAGGAAGAGAAGAAGAAAAGGCUCCAGGCCUUCCAAGGGU

ACCAGGUCACCAUGAAAACCGCCAAAGUCGCCGCAUCCGAUUGGACCUUC

CUCCACUGCCUGCCUCGGAAGCCUGAAGAGGUCGACGACGAAGUGUUCUA

CUCUCCCCGCUCCCUUGUGUUCCCCGAGGCCGAGAACAGGAAGUGGACCA

UUAUGGCCGUGAUGGUGUCGCUCCUGACCGACUACAGCCCGCAGCUGCAG

AAGCCCAAGUUCUGA

In some embodiments, a suitable mRNA may be a
codon optimized sequence as shown in SEQ ID NO: 9.
(SEQ ID NO: 9)
AUGCUGUUCAAUCUUCGGAUCCUGCUGAACAACGCCGCCUUUCGGAACGG

GCACAACUUCAUGGUCCGCAACUUCCGCUGUGGACAGCCGCUGCAGAACA

AGGUCCAGCUUAAGGGCCGGGAUCUCCUGACCCUGAAGAACUUUACCGGA

GAAGAAAUCAAGUACAUGCUCUGGCUGAGCGCCGACCUCAAGUUCCGGAU

UAAGCAGAAGGGGGAGUACCUCCCGCUGCUUCAAGGAAAGUCCCUGGGGA

UGAUCUUCGAGAAGCGGAGCACUAGGACCAGGCUGUCGACCGAAACGGGC

UUUGCACUGCUGGGUGGACACCCAUGCUUCCUGACCACCAAGAUAUUCA

UCUCGGCGUGAACGAAUCCUUGACUGACACUGCGCGCGUCCUCUCAUCGA

UGGCUGAUGCCGUGUUGGCUAGAGUGUACAAGCAGUCAGACCUGGACACU

CUGGCUAAGGAAGCCUCCAUUCCGAUCAUCAACGGCCUGUCCGACCUGUA

CCACCCGAUUCAGAUUCUGGCCGACUACCUGACCCUGCAAGAGCACUAUU

CGAGCCUUAAAGGGUUGACCCUGUCCUGGAUCGGCGACGGAAACAAUAUC

UUGCACUCCAUUAUGAUGUCCGCCGCCAAGUUCGGCAUGCAUCUCCAAGC

CGCGACUCCUAAGGGUUACGAGCCCGACGCAUCCGUGACAAAACUGGCCG

AGCAGUACGCGAAGGAAAACGGUACCAAGCUCCUGCUGACCAAUGAUCCU

CUCGAGGCUGCGCACGAGGAAACGUGCUCAUCACCGACACCUGGAUCAG

CAUGGGACAGGAAGAGGAAAAGAAAAAGCGCCUGCAGGCAUUCCAGGGCU

ACCAAGUCACUAUGAAAACCGCCAAAGUGGCCGCCUCGGAUUGGACCUUC

CUUCACUGCCUGCCAAGAAAGCCUGAGGAAGUGGACGACGAAGUGUUCUA

CUCCCCCGCUCUCUCGUGUUCCCCGAGGCCGAGAACCGGAAGUGGACCA

UCAUGGCCGUGAUGGUGUCACUGCUCACUGACUACAGCCCGCAGCUGCAG

AAGCCCAAGUUCUAA

In some embodiments, a suitable mRNA may be a
codon optimized sequence as shown in SEQ ID NO: 10.
(SEQ ID NO: 10)
AUGCUGUUCAACCUCCGGAUUCUGCUGAACAACGCCGCUUUCCGCAACGG

CCACAAUUUCAUGGUCCGGAACUUCAGAUGCGGCCAGCCGUUGCAGAACA

AGGUCCAGCUUAAGGGACGCGAUCUGCUGACCCUGAAGAACUUCACCGGA

GAGGAAAUCAAGUAUAUGCUGUGGCUCUCGGCCGACCUGAAGUUCAGGAU

CAAGCAGAAGGGGGAGUACCUCCCGCUGUUGCAAGGAAAGUCCCUGGGCA

UGAUUUCGAGAAGCGCUCAACUCGCACCAGGCUCUCCACCGAAACUGGU

UUUGCCCUUCUGGGCGGUCAUCCUUGCUUUCUGACGACCCAGGACAUUCA

CCUCGGAGUGAAUGAGAGCCUGACCGACACUGCCAGAGUGCUGUCCUCCA

UGGCGGAUGCAGUGUUGGCGCGGGUGUACAAGCAGUCAGACCUGGACACC

CUGGCGAAGGAAGCGUCAAUCCCCAUCAUUAACGGACUGAGCGACCUGUA

CCACCCGAUCCAGAUCCUCGCCGACUACCUGACUCUCCAAGAACACUACU

CGUCCCUGAAAGGGCUGACCUUGAGCUGGAUCGGCGACGGCAACAACAUC

CUGCAUUCCAUCAUGAUGAGCGCCGCCAAGUUCGGAAUGCACCUUCAAGC

CGCAACACCGAAGGGCUACGAGCCGGAUGCCUCGGUGACCAAGCUGGCCG

AGCAGUACGCCAAGGAAAACGGGACCAAGCUGCUGCUCACUAACGACCCU

CUGGAAGCUGCUCACGGGGAAACGUGCUGAUCACCGACACCUGGAUUUC

CAUGGGACAGGAAGAAGAGAAAAAGAAGCGGCUUCAGGCGUUCCAGGGUU

ACCAAGUCACCAUGAAAACCGCCAAAGUGGCAGCCAGCGACUGGACUUUC

CUGCAUUGUCUCCCUCGGAAGCCUGAGGAAGUGGAUGACGAAGUGUUUA

CUCUCCCCGCUCCCUGGUGUUCCCCGAGGCCGAGAACCGGAAGUGGACUA

UCAUGGCCGUGAUGGUGUCCCUCCUGACCGAUUACUCCCCACAACUGCAG

AAGCCCAAGUUCUGA

In some embodiments, a suitable mRNA sequence may be an mRNA sequence a homolog or an analog of human OTC protein. For example, a homolog or an analog of human OTC protein may be a modified human OTC protein containing one or more amino acid substitutions, deletions, and/or insertions as compared to a wild-type or naturally-occurring human OTC protein while retaining substantial OTC protein activity. In some embodiments, an mRNA suitable for the present invention encodes an amino acid sequence at least 70%, 75%, 80%, 85%, 90%, 91%, 92%, 93%, 94%, 95%, 96%, 97%, 98%, 99% or more homologous to SEQ ID NO: 3. In some embodiments, an mRNA suitable for the present invention encodes a protein substantially identical to human OTC protein. In some embodiments, an mRNA suitable for the present invention encodes an amino acid sequence at least 70%, 75%, 80%, 85%, 90%, 91%, 92%, 93%, 94%, 95%, 96%, 97%, 98%, 99% or more identical to SEQ ID NO: 3. In some embodiments, an mRNA suitable for the present invention encodes a fragment or a portion of human OTC protein. In some embodiments, an mRNA suitable for the present invention encodes a fragment or a portion of human OTC protein, wherein the fragment or portion of the protein still maintains OTC activity similar to that of the wild-type protein. In some embodiments, an mRNA suitable for the present invention has a nucleotide sequence at least 70%, 75%, 80%, 85%, 90%, 91%, 92%, 93%, 94%, 95%, 96%, 97%, 98%, 99% or more identical to SEQ ID NO: 1, SEQ ID NO: 4, SEQ ID NO: 5, SEQ ID NO: 6, SEQ ID NO: 7, SEQ ID NO: 8, SEQ ID NO: 9, or SEQ ID NO: 10.

In some embodiments, a suitable mRNA encodes a fusion protein comprising a full length, fragment or portion of an OTC protein fused to another protein (e.g., an N or C terminal fusion). In some embodiments, the protein fused to the mRNA encoding a full length, fragment or portion of an OTC protein encodes a signal or a cellular targeting sequence.

Messenger RNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Modified mRNA

In some embodiments, mRNA according to the present invention may be synthesized as unmodified or modified mRNA. Typically, mRNAs are modified to enhance stability. Modifications of mRNA can include, for example, modifications of the nucleotides of the RNA. A modified mRNA according to the invention can thus include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, mRNAs (e.g., OTC-encoding mRNAs) may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs (e.g., OTC-encoding mRNAs) may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs (e.g., OTC-encoding mRNAs) may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methylguanosine 5'-triphosphate, pseudouridine 5'-triphosphate, puromycin 5'-triphosphate or xanthosine 5'-triphosphate.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs (e.g., OTC-encoding mRNAs) include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

In some embodiments, mRNAs (e.g., OTC-encoding mRNAs) include a 3' poly(A) tail structure. A poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Cap Structure

In some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form $m^7G(5')ppp(5')G$ ("$m^7GpppG$") as an initiator of transcription.

To date, a usual form of a synthetic dinucleotide cap used in in vitro translation experiments is the Anti-Reverse Cap Analog ("ARCA") or modified ARCA, which is generally a modified cap analog in which the 2' or 3' OH group is replaced with —OCH$_3$.

Additional cap analogs include, but are not limited to, a chemical structures selected from the group consisting of $m^7GpppG$, $m^7GpppA$, $m^7GpppC$; unmethylated cap analogs (e.g., GpppG); dimethylated cap analog (e.g., $m^{2,7}GpppG$), trimethylated cap analog (e.g., $m^{2,2,7}GpppG$), dimethylated symmetrical cap analogs (e.g., $m^7Gpppm^7G$), or anti reverse cap analogs (e.g., ARCA; $m^{7,2'Ome}GpppG$, $m^{72'd}GpppG$, $m^{7,3'Ome}GpppG$, $m^{7,3'd}GpppG$ and their tetraphosphate derivatives) (see, e.g., Jemiility, J. et al., "Novel 'anti-reverse' cap analogs with superior translational properties", RNA, 9: 1108-1122 (2003)).

In some embodiments, a suitable cap is a 7-methyl guanylate ("$m^7G$") linked via a triphosphate bridge to the 5'-end of the first transcribed nucleotide, resulting in $m^7G$ (5')ppp(5')N, where N is any nucleoside. A preferred embodiment of a m$^7$G cap utilized in embodiments of the invention is $m^7G(5')ppp(5')G$.

In some embodiments, the cap is a Cap0 structure. Cap0 structures lack a 2'-O-methyl residue of the ribose attached to bases 1 and 2. In some embodiments, the cap is a Cap1 structure. Cap1 structures have a 2'-O-methyl residue at base 2. In some embodiments, the cap is a Cap2 structure. Cap2 structures have a 2'-O-methyl residue attached to both bases 2 and 3.

A variety of m$^7$G cap analogs are known in the art, many of which are commercially available. These include the m$^7$GpppG described above, as well as the ARCA 3'-OCH$_3$ and 2'-OCH$_3$ cap analogs (Jemiility, J. et al., RNA, 9: 1108-1122 (2003)). Additional cap analogs for use in embodiments of the invention include N7-benzylated dinucleoside tetraphosphate analogs (described in Grudzien, E. et al., RNA, 10: 1479-1487 (2004)), phosphorothioate cap analogs (described in Grudzien-Nogalska, E., et al., RNA, 13: 1745-1755 (2007)), and cap analogs (including biotinylated cap analogs) described in U.S. Pat. Nos. 8,093,367 and 8,304,529, incorporated by reference herein.

Tail Structure

Typically, the presence of a "tail" serves to protect the mRNA from exonuclease degradation. The poly A tail is thought to stabilize natural messengers and synthetic sense RNA. Therefore, in certain embodiments a long poly A tail can be added to an mRNA molecule thus rendering the RNA more stable. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)).

In some embodiments, mRNAs include a 3' poly(A) tail structure. Typically, the length of the poly A tail can be at least about 10, 50, 100, 200, 300, 400 at least 500 nucleotides. In some embodiments, a poly-A tail on the 3' terminus of mRNA typically includes about 10 to 300 adenosine nucleotides (e.g., about 10 to 200 adenosine nucleotides, about 10 to 150 adenosine nucleotides, about 10 to 100 adenosine nucleotides, about 20 to 70 adenosine nucleotides, or about 20 to 60 adenosine nucleotides). In some embodiments, mRNAs include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the length of the poly A or poly C tail is adjusted to control the stability of a modified sense mRNA molecule of the invention and, thus, the transcription of protein. For example, since the length of the poly A tail can influence the half-life of a sense mRNA molecule, the length of the poly A tail can be adjusted to modify the level of resistance of the mRNA to nucleases and thereby control the time course of polynucleotide expression and/or polypeptide production in a target cell.

5' and 3' Untranslated Region

In some embodiments, mRNAs include a 5' untranslated region (UTR). In some embodiments, mRNAs include a 3' untranslated region. In some embodiments, mRNAs include both a 5' untranslated region and a 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and 5' untranslated region sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

In certain embodiments of the invention, a codon-optimized human ornithine transcarbamylase messenger RNA (OTC mRNA) is synthesized by in vitro transcription from a plasmid DNA template encoding the gene, which is followed by the addition of a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail of approximately 100, 200, 250, 300, 400 or 500 nucleotides in length as determined by gel electrophoresis.

In certain embodiments, the codon-optimized OTC mRNA includes a coding region having a codon-optimized coding region flanked by 5' and 3' untranslated regions as represented as X and Y, respectively (vide infra)

X-Coding Region-Y where the coding region sequence is SEQ ID NO: 4 or a sequence 70%, 75%, 80%, 85%, 90%, 91%, 92%, 93%, 94%, 95%, 96%, 97%, 98%, 99% or more identical to SEQ ID NO: 4; or SEQ ID NO: 5 or a sequence 70%, 75%, 80%, 85%, 90%, 91%, 92%, 93%, 94%, 95%, 96%, 97%, 98%, 99% or more identical to SEQ ID NO: 5; or SEQ ID NO: 6 or a sequence 70%, 75%, 80%, 85%, 90%, 91%, 92%, 93%, 94%, 95%, 96%, 97%, 98%, 99% or more identical to SEQ ID NO: 6; or SEQ ID NO: 7 or a sequence 70%, 75%, 80%, 85%, 90%, 91%, 92%, 93%, 94%, 95%, 96%, 97%, 98%, 99% or more identical to SEQ ID NO: 7; or SEQ ID NO: 8 or a sequence 70%, 75%, 80%, 85%, 90%, 91%, 92%, 93%, 94%, 95%, 96%, 97%, 98%, 99% or more identical to SEQ ID NO: 8; or SEQ ID NO: 9 or a sequence 70%, 75%, 80%, 85%, 90%, 91%, 92%, 93%, 94%, 95%, 96%, 97%, 98%, 99% or more identical to SEQ ID NO: 9; or SEQ ID NO: 10 or a sequence 70%, 75%, 80%, 85%, 90%, 91%, 92%, 93%, 94%, 95%, 96%, 97%, 98%, 99% or more identical to SEQ ID NO: 10; and where X (5' UTR Sequence) is (SEQ ID NO: 11)
GGACAGAUCGCCUGGAGACGCCAUCCACGCUGUUUUGACCUCCAUAGAA

GACACCGGGACCGAUCCAGCCUCCGCGGCCGGGAACGGUGCAUUGGAAC

GCGGAUUCCCCGUGCCAAGAGUGACUCACCGUCCUUGACACG or a sequence 70%, 75%, 80%, 85%, 90%, 91%, 92%, 93%, 94%, 95%, 96%, 97%, 98%, 99% or more identical to SEQ ID NO: 11; and where Y (3' UTR Sequence) is (SEQ ID NO: 12)
CGGGUGGCAUCCCUGUGACCCCUCCCCAGUGCCUCUCCUGGCCCUGGAA

GUUGCCACUCCAGUGCCCACCAGCCUUGUCCUAAUAAAAUUAAGUUGCA

UCAAGCU or a sequence 70%, 75%, 80%, 85%, 90%, 91%, 92%, 93%, 94%, 95%, 96%, 97%, 98%, 99% or more identical to SEQ ID NO: 12, or (SEQ ID NO: 13)
GGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAU

CAAAGCU or a sequence 70%, 75%, 80%, 85%, 90%, 91%, 92%, 93%, 94%, 95%, 96%, 97%, 98%, 99% or more identical to SEQ ID NO: 13.

Delivery Vehicles

According to the present invention, mRNA encoding an OTC protein (e.g., a full length, fragment or portion of an OTC protein) as described herein may be delivered as naked RNA (unpackaged) or via delivery vehicles. As used herein, the terms "delivery vehicle," "transfer vehicle," "nanoparticle" or grammatical equivalent, are used interchangeably.

In some embodiments, mRNAs encoding an OTC protein may be delivered via a single delivery vehicle. In some embodiments, mRNAs encoding an OTC protein may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags.

Liposomal Delivery Vehicles

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). In the context of the present invention, a liposomal delivery vehicle typically serves to transport a desired mRNA to a target cell or tissue.

Cationic Lipids

As used herein, the phrase "cationic lipids" refers to any of a number of lipid species that have a net positive charge at a selected pH, such as physiological pH. Several cationic lipids have been described in the literature, many of which are commercially available. Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z, 9Z, 28Z, 31Z)-heptatriaconta-6,9,28,31-tetraen-19-yl 4-(dimethylamino) butanoate, having a compound structure of:

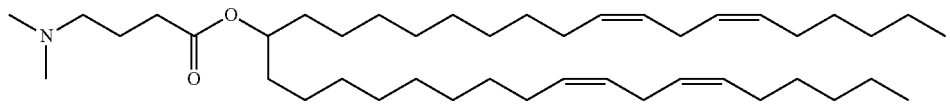 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

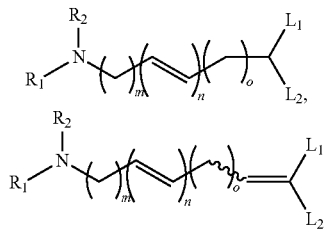

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)—N,N-dimethyl-6-(9Z, 12Z)-octadeca-9,12-dien-1-yl) tetracosa-15,18-dien-1-amine ("HGT5000"), having a compound structure of:

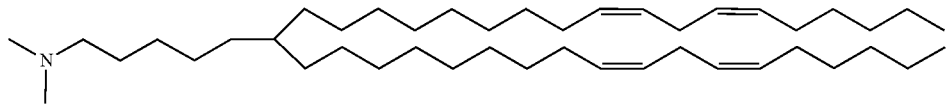 [SMILES: CCCCC/C=C\C/C=C\CCCCCCCCC(CCCCCCCC/C=C\C/C=C\CCCCC)CCCCCN(C)C]

and pharmaceutically acceptable salts thereof. In certain embodiments, the compositions an methods of the present invention include the cationic lipid (15Z, 18Z)—N,N-dimethyl-6-((9Z, 12Z)-octadeca-9,12-dien-1-yl) tetracosa-4,15,18-trien-1-amine ("HGT5001"), having a compound structure of:

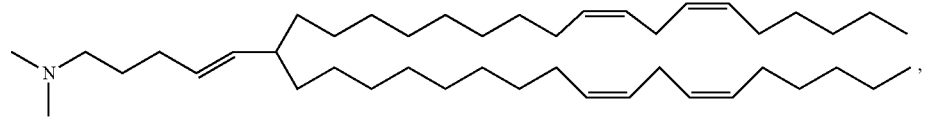 [SMILES: CCCCC/C=C\C/C=C\CCCCCCCCC(/C=C/CCCN(C)C)CCCCCCCC/C=C\C/C=C\CCCCC]

and pharmaceutically acceptable salts thereof. In certain embodiments, the compositions and methods of the present invention include the cationic lipid and (15Z, 18Z)—N,N-dimethyl-6-((9Z, 12Z)-octadeca-9,12-dien-1-yl) tetracosa-5,15,18-trien-1-amine ("HGT5002"), having a compound structure of:

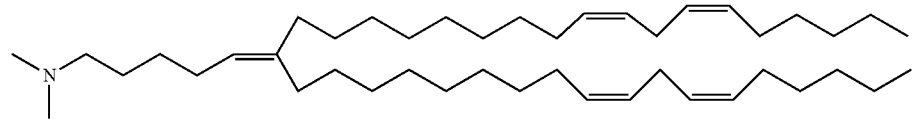 [SMILES: CCCCC/C=C\C/C=C\CCCCCCCCC(=CCCCCN(C)C)CCCCCCCC/C=C\C/C=C\CCCCC]

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

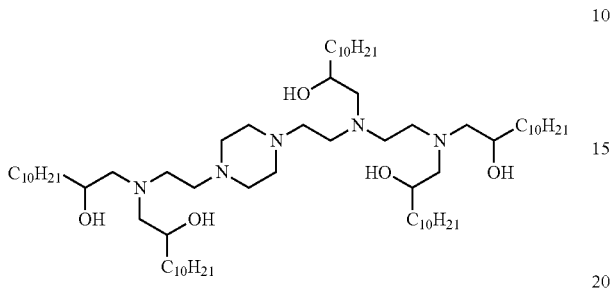

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

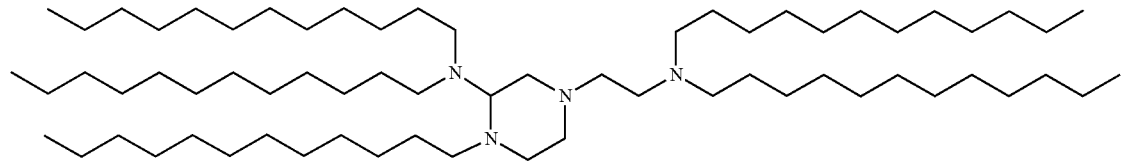 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

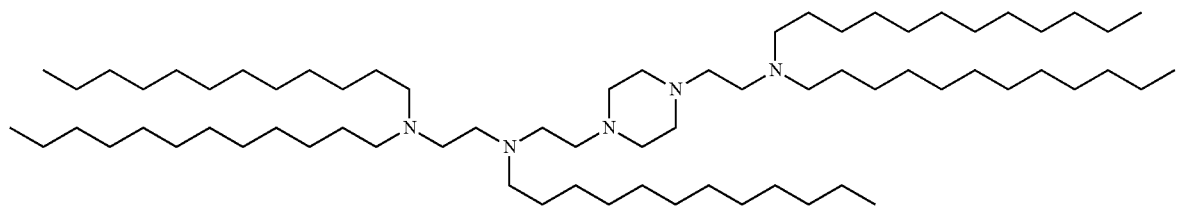 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publication WO 2017/112865, which is incorporated herein by reference. In certain embodiments, the compositions and methods of the present invention include a cationic lipid having a compound structure of:

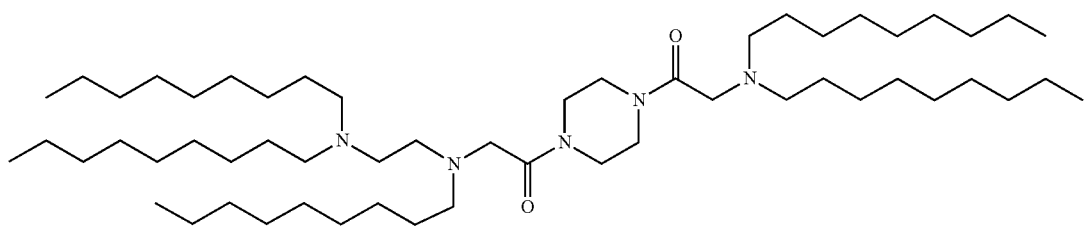 [SMILES: CCCCCCCCCN(CCCCCCCCC)CCN(CCCCCCCCC)CC(=O)N1CCN(C(=O)CN(CCCCCCCCC)CCCCCCCCC)CC1]

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

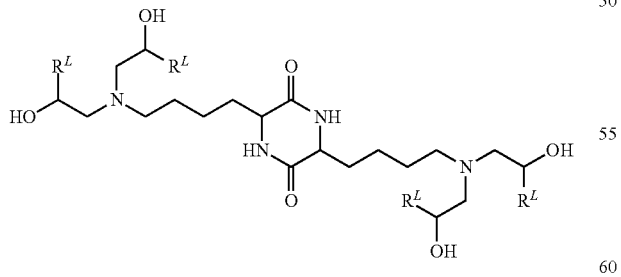

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

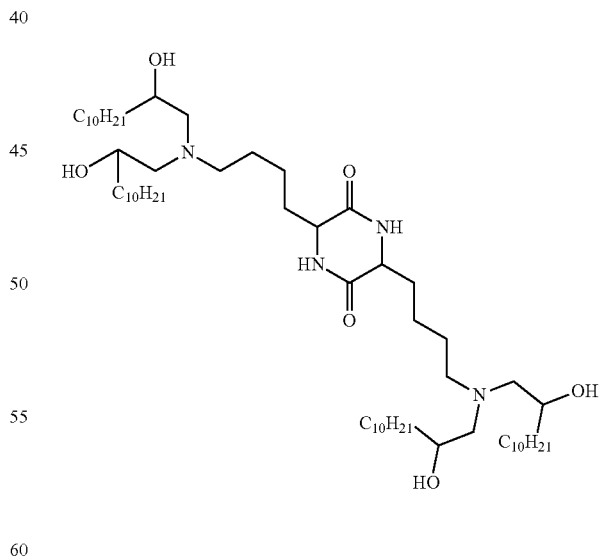

and pharmaceutically acceptable salts thereof. In certain embodiments, the compositions and methods of the present invention include a cationic lipid having a compound structure of:

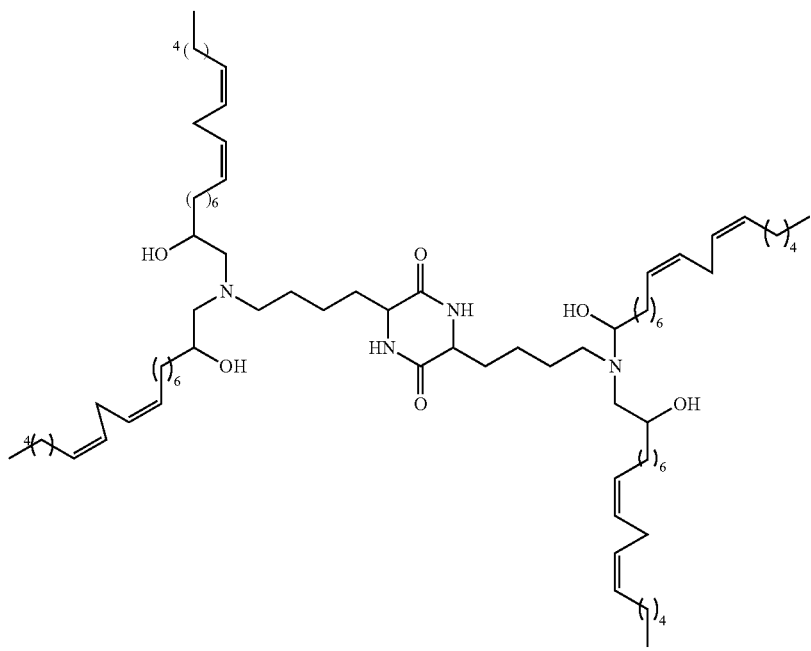

and pharmaceutically acceptable salts thereof. In certain embodiments, the compositions and methods of the present invention include a cationic lipid having a compound structure of:

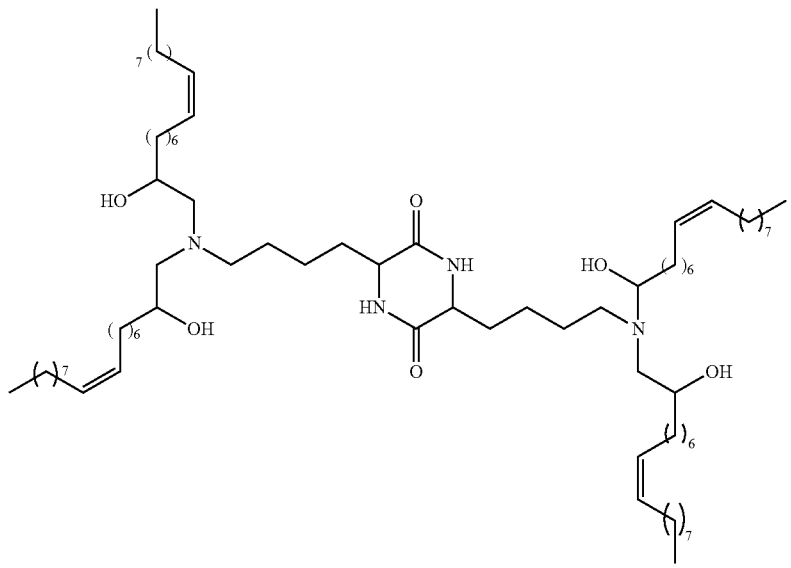

and pharmaceutically acceptable salts thereof. In certain embodiments, the compositions and methods of the present invention include a cationic lipid having a compound structure of:

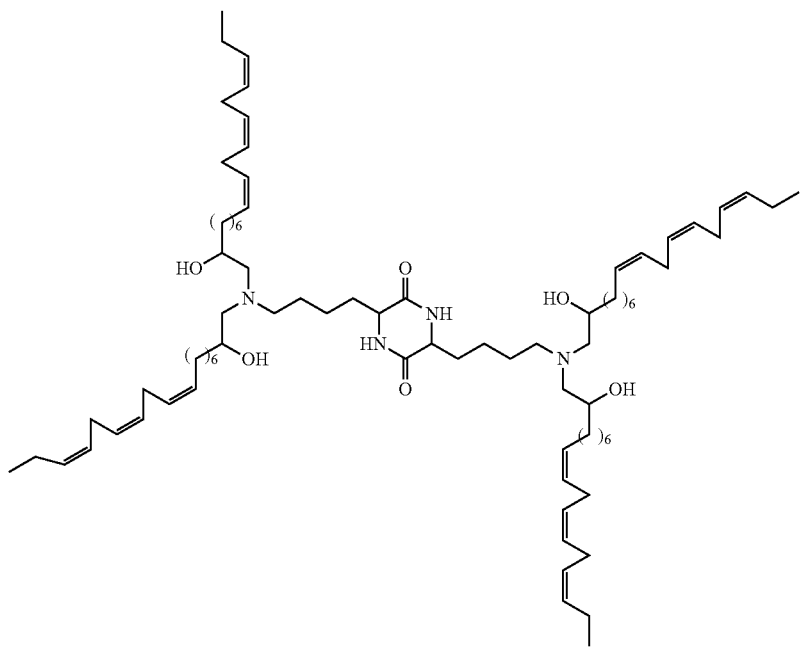

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

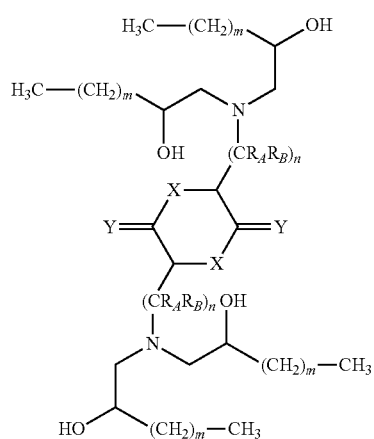

or a pharmaceutically acceptable salt thereof, wherein each X independently is O or S; each Y independently is O or S; each m independently is 0 to 20; each n independently is 1 to 6; each RA is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each RB is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

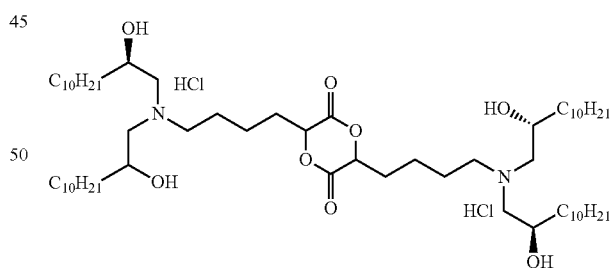

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

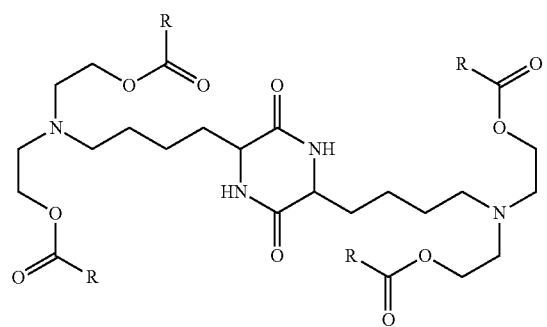
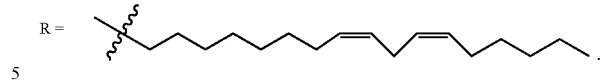

or a pharmaceutically acceptable salt thereof. In some embodiments, the compositions and methods of the present invention include a cationic lipid having the compound structure:

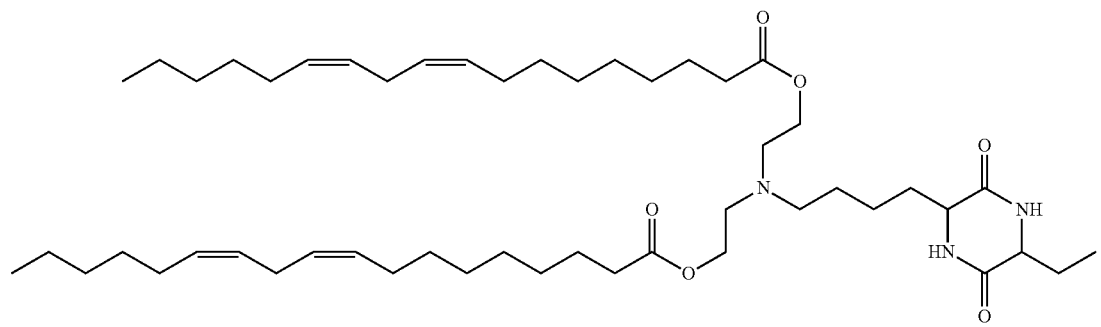 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

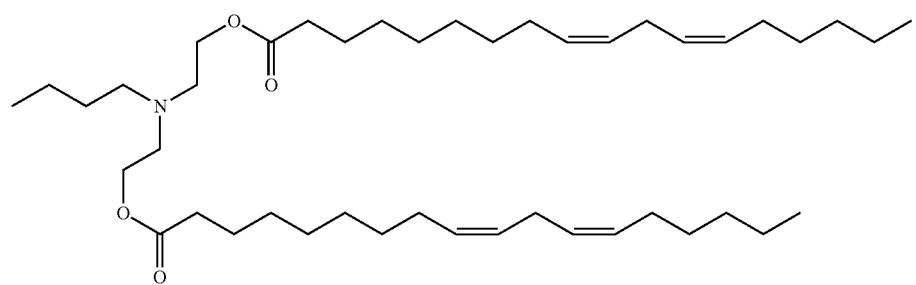 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

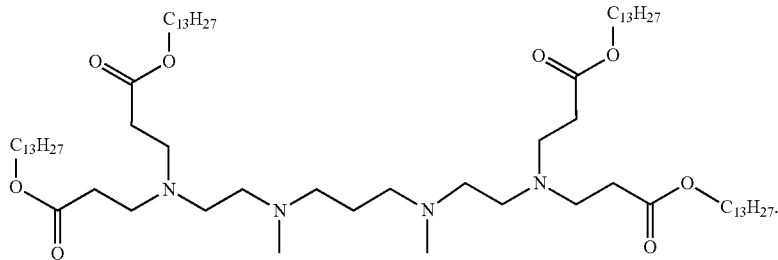

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

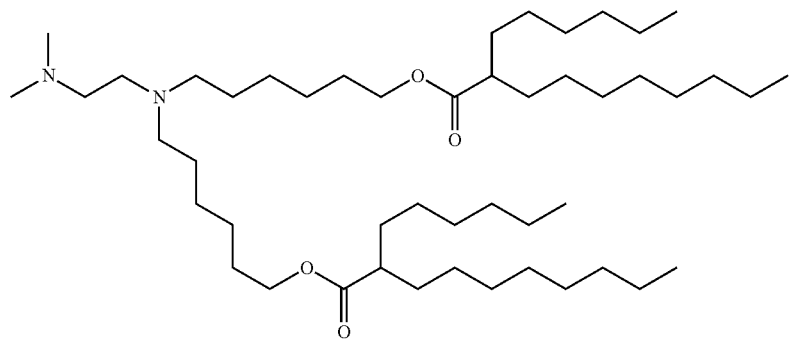 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

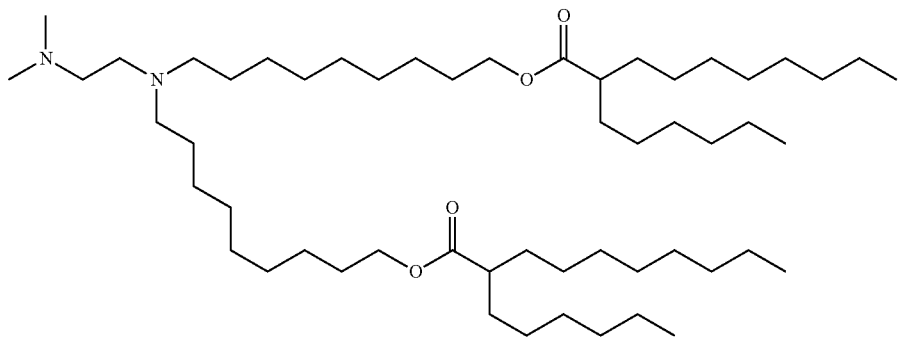 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

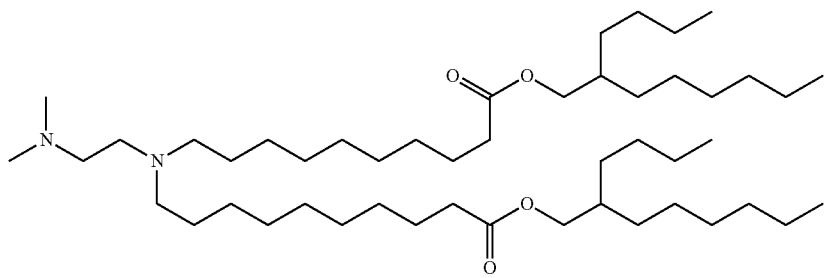 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

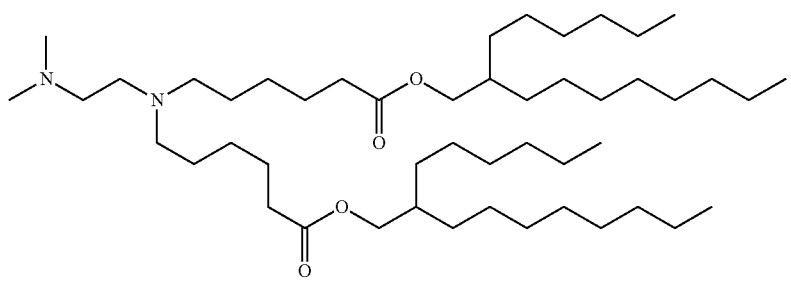 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

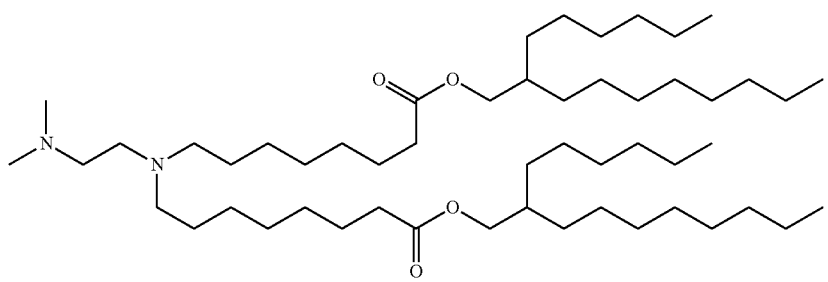 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

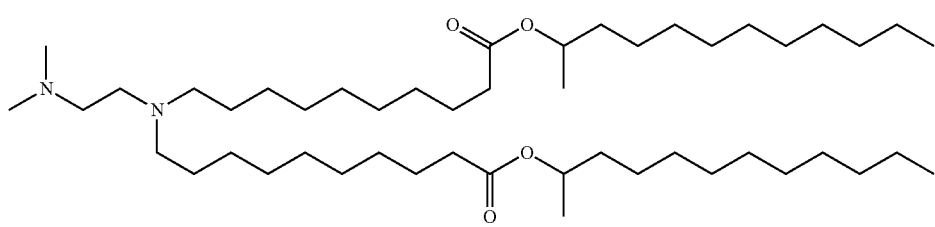 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

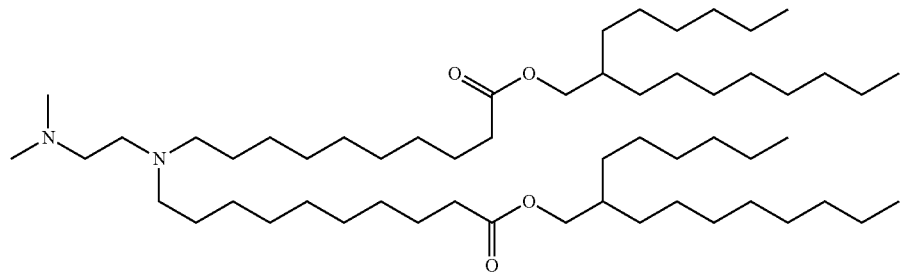 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

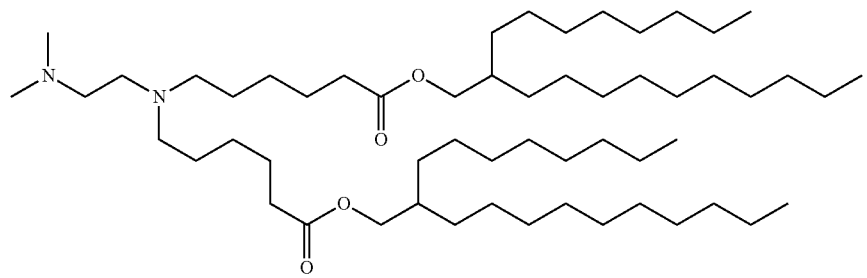 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

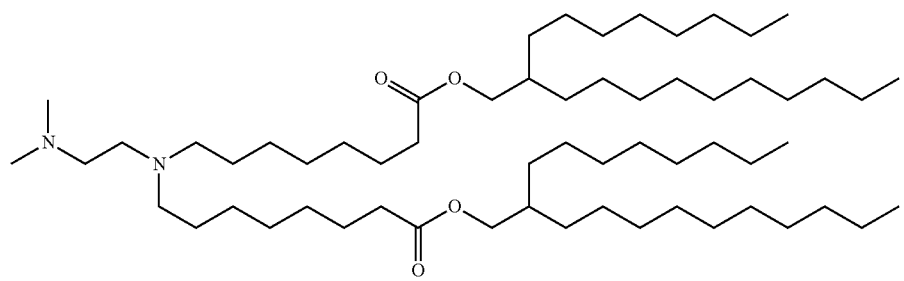 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

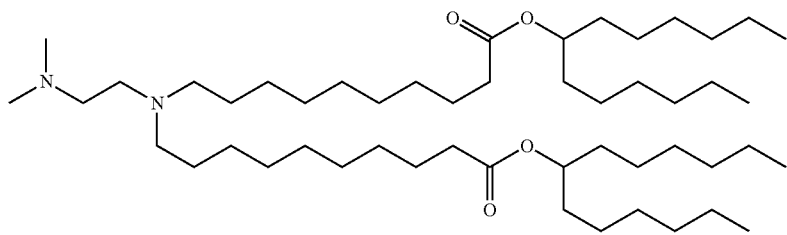 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

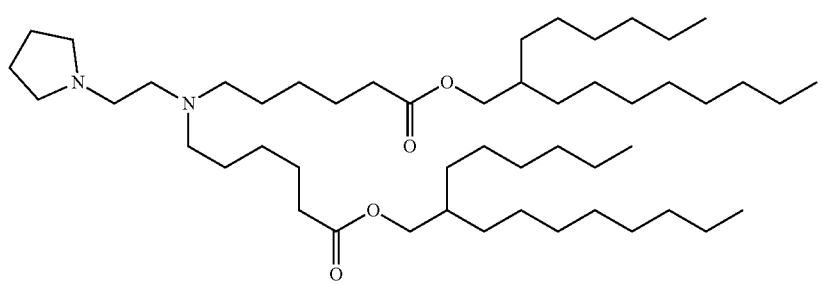 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

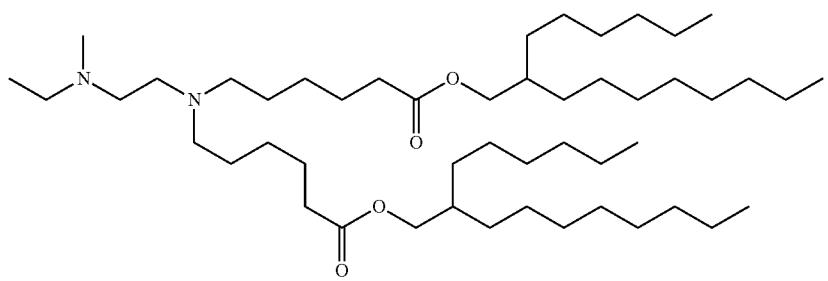 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

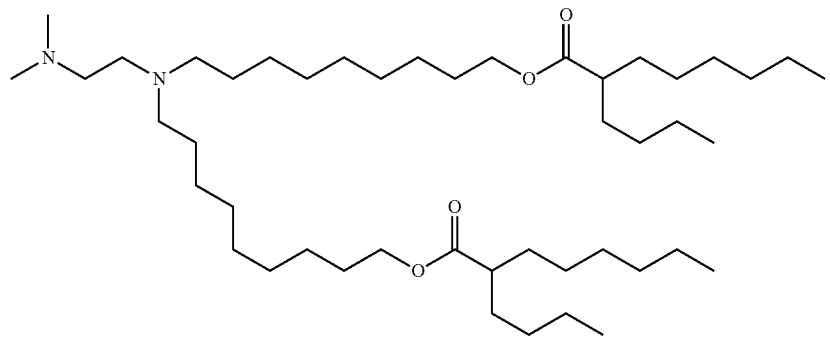 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

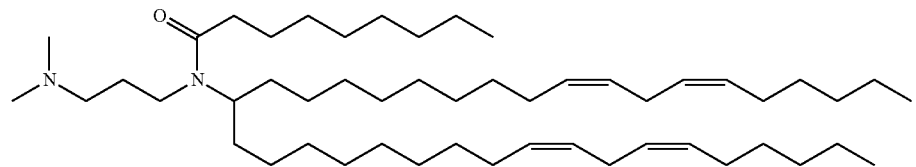 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

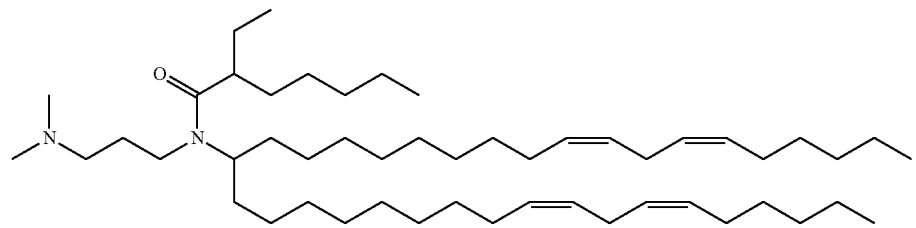 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

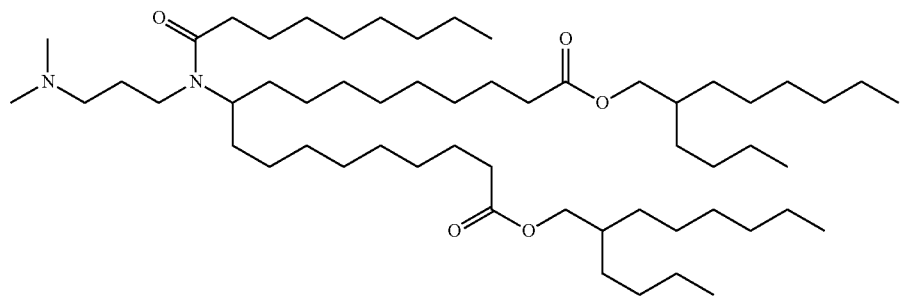 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

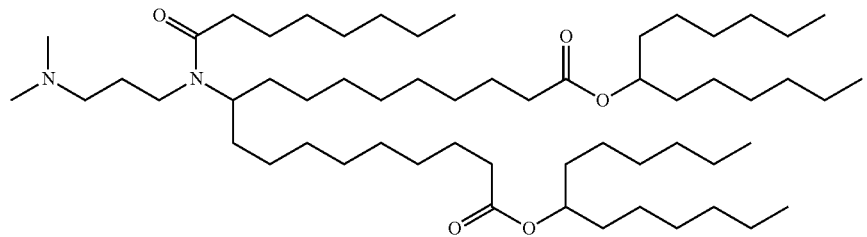 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

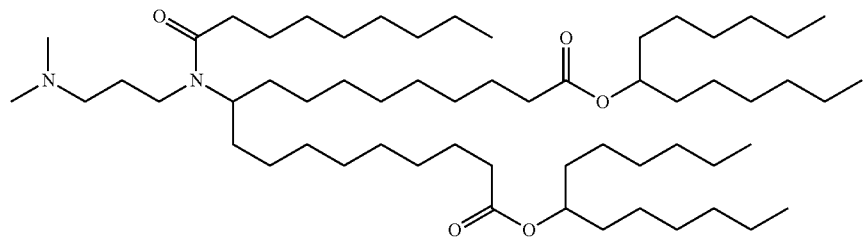 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

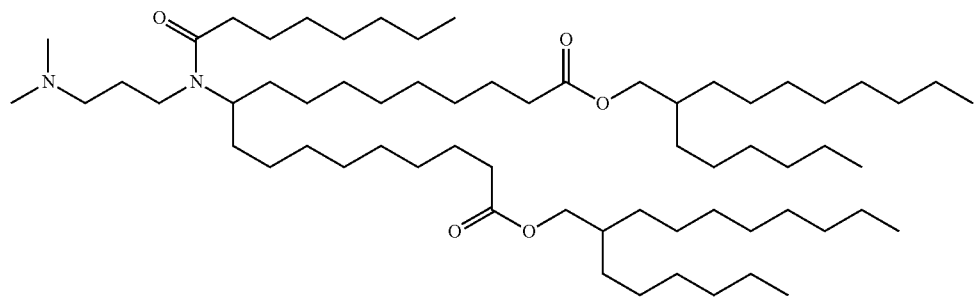 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

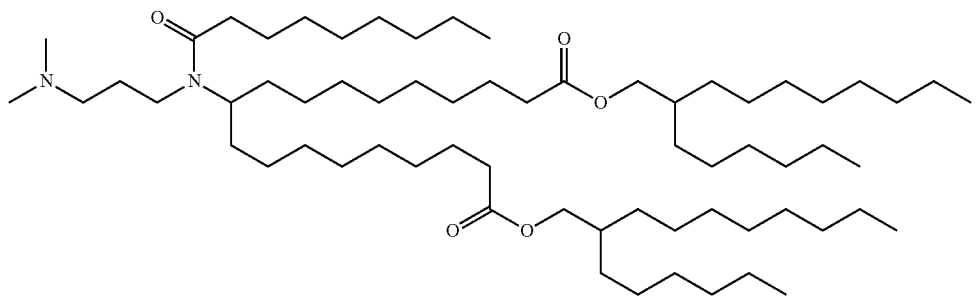 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

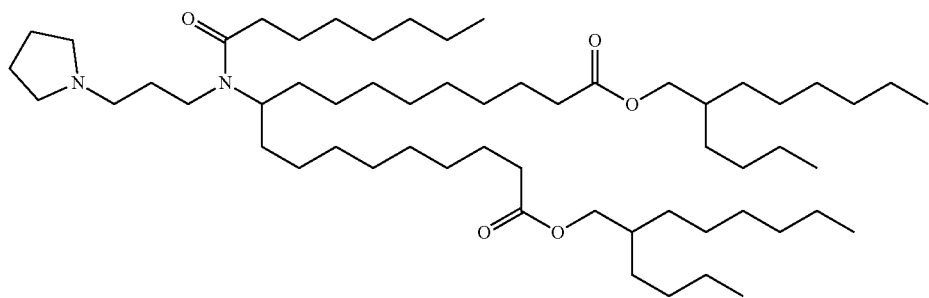 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

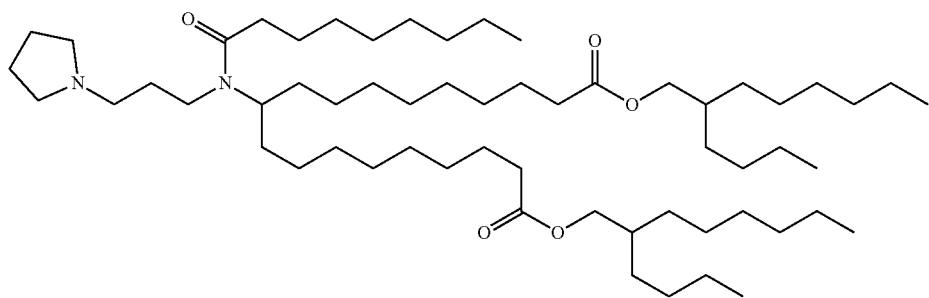 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

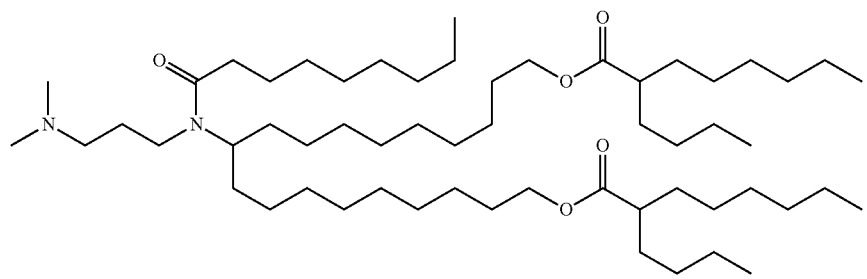 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

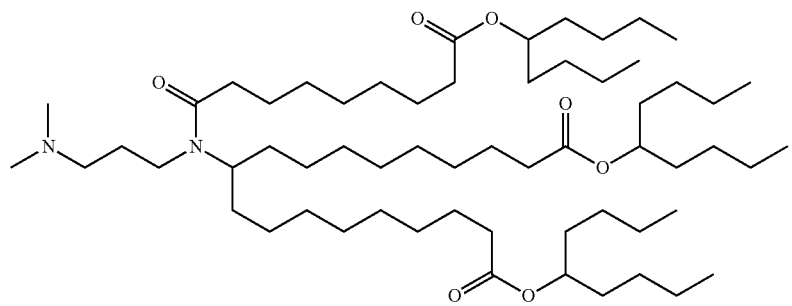 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

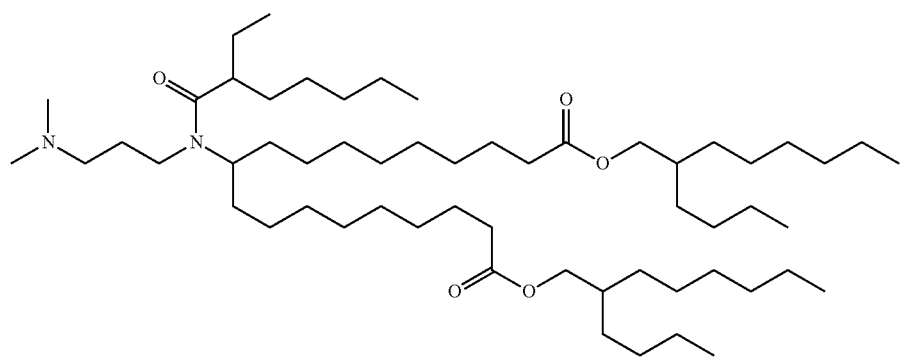 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

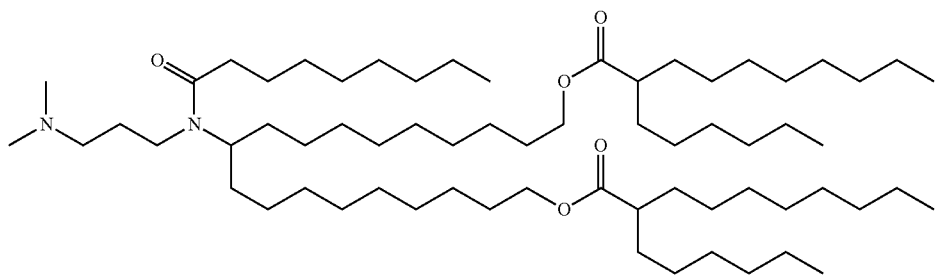 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

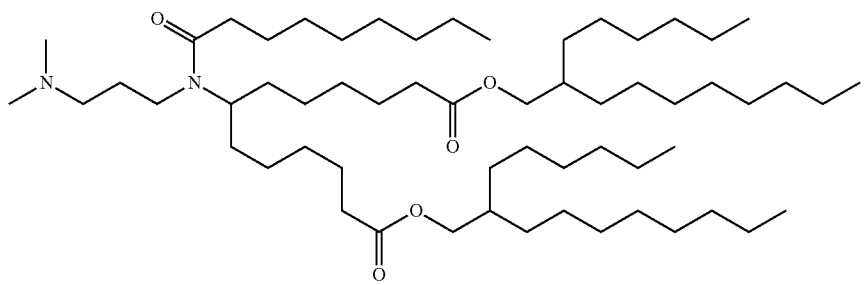 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

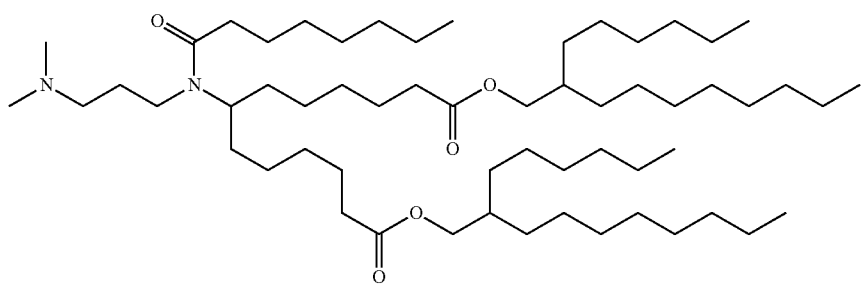 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

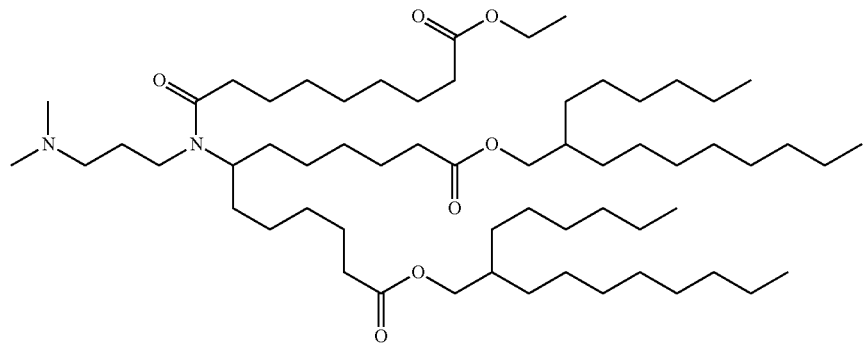 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

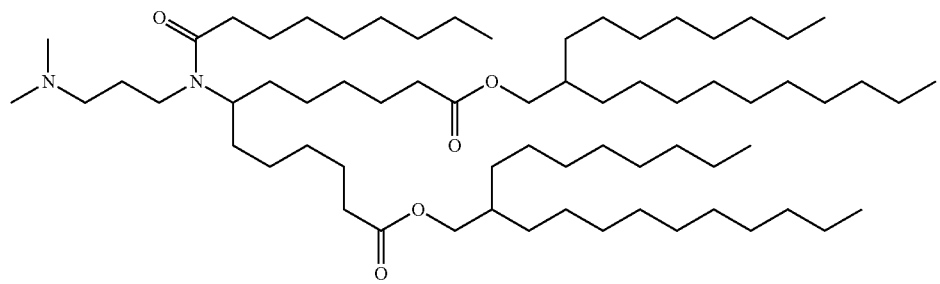 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

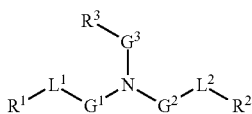

or a pharmaceutically acceptable salt thereof, wherein one of $L^1$ or $L^2$ is —O(C=O)—, —(C=O)O—, —C(=O)—, —O—, —S(O)$_x$—, —S—S—, —C(=O)S—, —SC(=O)—, —NR$^a$C(=O)—, —C(=O)NR$^a$—, NR$^a$C(=O)NR$^a$—, —OC(=O)NR$^a$—, or —NR$^a$C(=O)O—; and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; Ra is H or $C_1$-$C_{12}$ alkyl; $R^1$ and $R^2$ are each independently $C_6$-$C_{24}$ alkyl or $C_6$-$C_{24}$ alkenyl; $R^3$ is H, OR$^5$, CN, —C(=O)OR$^4$, —OC(=O)R$^4$ or —NR$^5$C(=O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

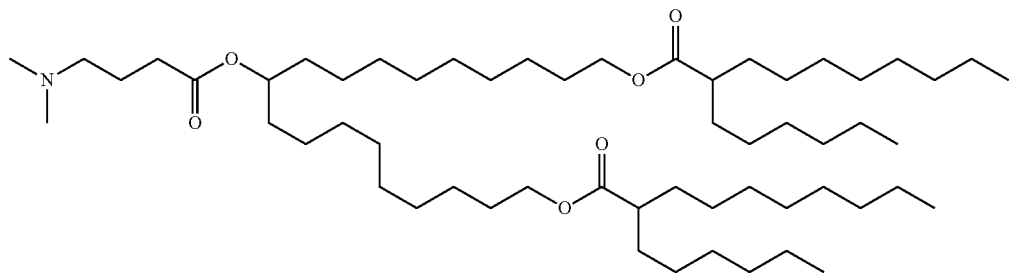 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the resent invention include a cationic lipid having the compound structure:

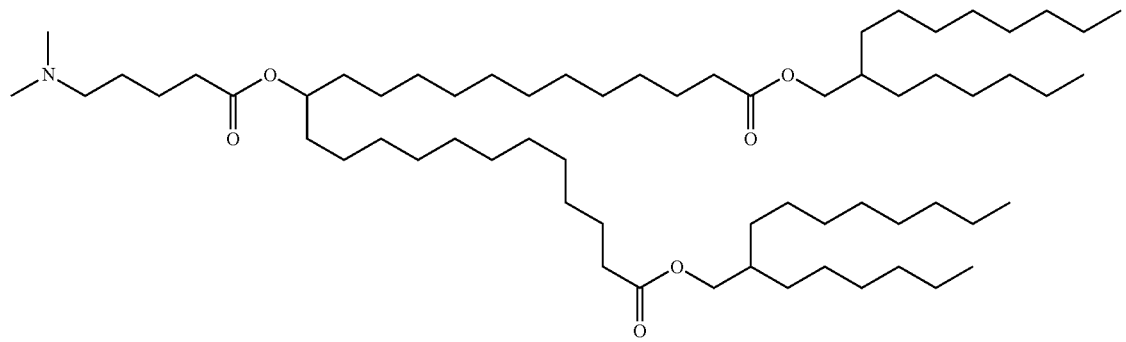 [SMILES: CCCCCCCCC(CCCCCC)COC(=O)CCCCCCCCCCCC(CCCCCCCCCCCC(=O)OCC(CCCCCC)CCCCCCCC)OC(=O)CCCCN(C)C]

and pharmaceutically acceptable salts thereof. In some embodiments, the compositions and methods of the present invention include a cationic lipid having the compound structure:

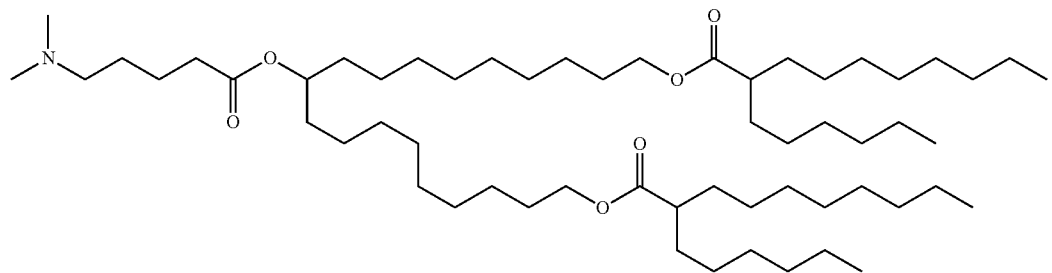 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

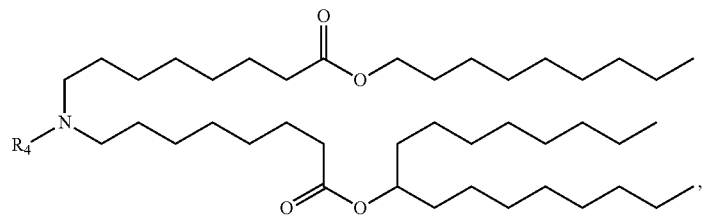

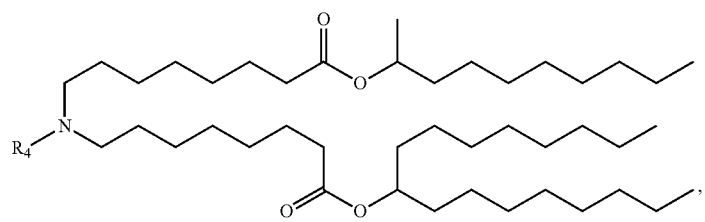

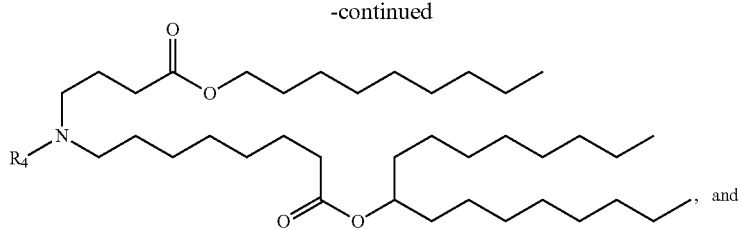

, and

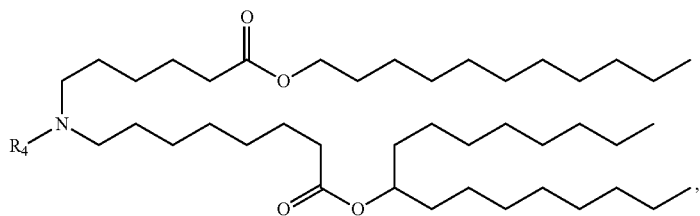

, and pharmaceutically acceptable salts thereof. For any one of these four formulas, $R_4$ is independently selected from —$(CH_2)_nQ$ and —$(CH_2)_nCHQR$; Q is selected from the group consisting of —OR, —OH, —O$(CH_2)_nN(R)_2$, —OC(O)R, —$CX_3$, —CN, —N(R)C(O)R, —N(H)C(O)R, —N(R)S(O)$_2$R, —N(H)S(O)$_2$R, —N(R)C(O)N(R)$_2$, —N(H)C(O)N(R)$_2$, —N(H)C(O)N(H)(R), —N(R)C(S)N(R)$_2$, —N(H)C(S)N(R)$_2$, —N(H)C(S)N(H)(R), and a heterocycle; and n is 1, 2, or 3. In certain embodiments, the compositions and methods of the present invention include a cationic lipid having a compound structure of:

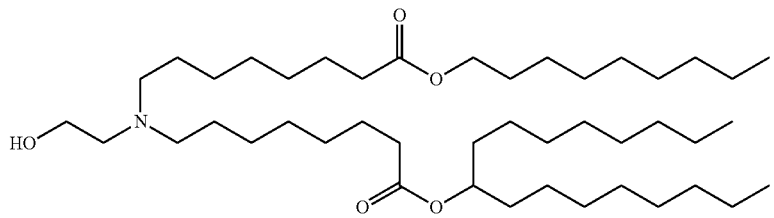 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

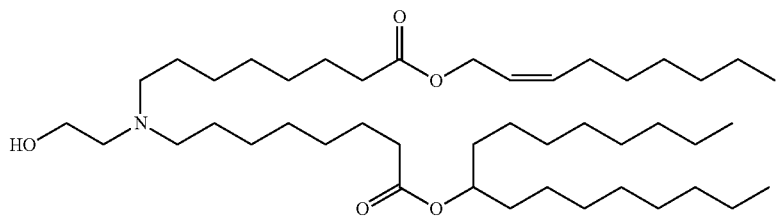 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

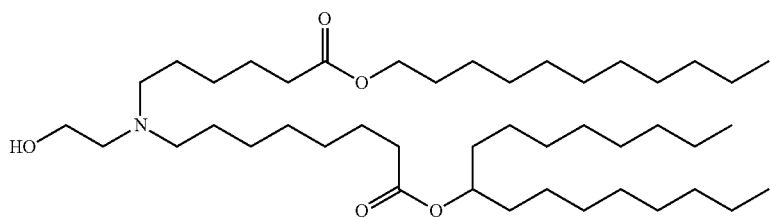 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

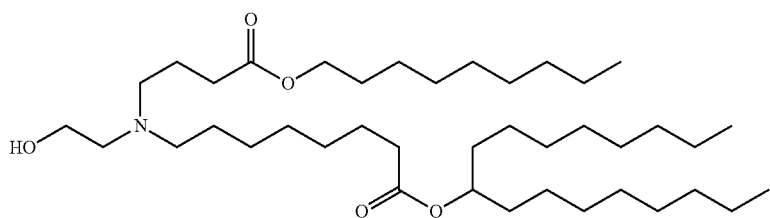 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

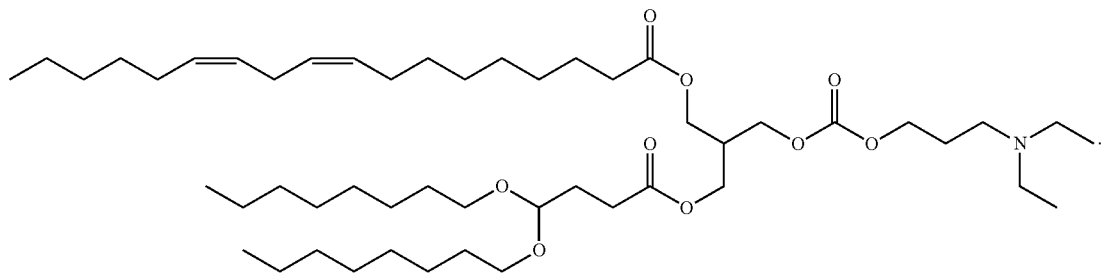 [SMILES: CCCCC/C=C\C/C=C\CCCCCCCC(=O)OCC(COC(=O)CCC(OCCCCCCCC)OCCCCCCCC)COC(=O)OCCCN(CC)CC]

and pharmaceutically acceptable salts thereof. In certain embodiments, the compositions and methods of the present invention include a cationic lipid having a compound structure of:

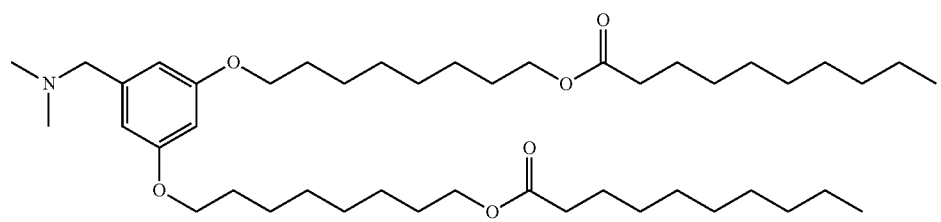 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

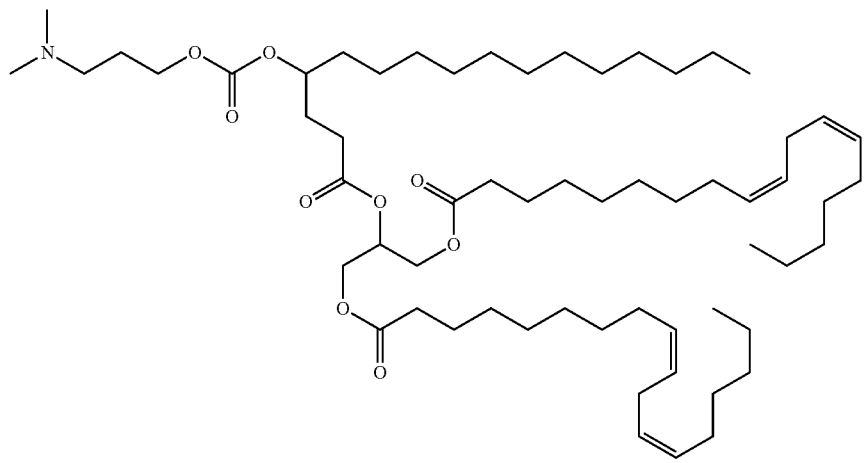 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

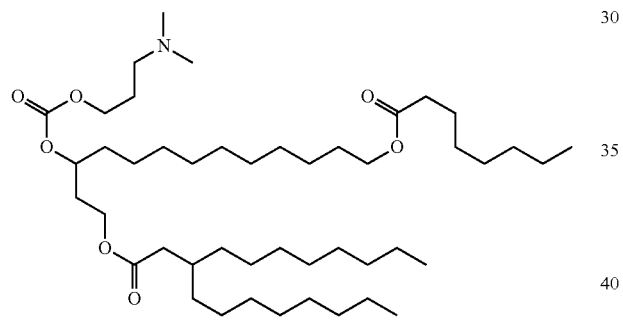

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

$$R_1 \!\!-\!\!(\ )_n\!\!-\!\!S\!\!-\!\!S\!\!-\!\!R_2,$$

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

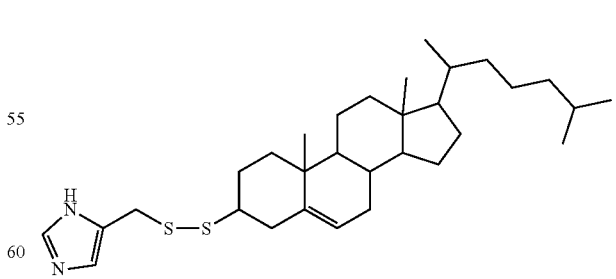

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

and pharmaceutically acceptable salts thereof. In certain embodiments, the compositions and methods of the present invention include a cationic lipid, "HGT4002", having a compound structure of:

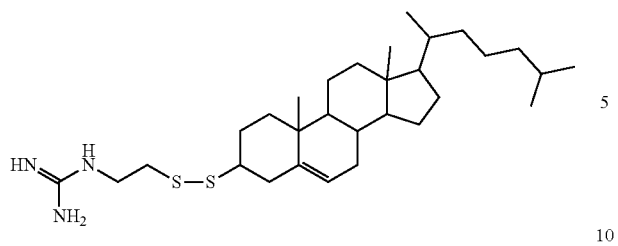

and pharmaceutically acceptable salts thereof. In certain embodiments, the compositions and methods of the present invention include a cationic lipid, "HGT4003", having a compound structure of:

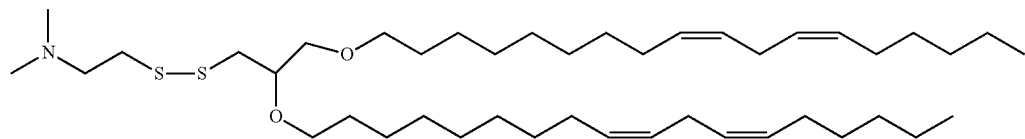 [SMILES: CCCCC/C=C\C/C=C\CCCCCCCCOCC(CSSCCN(C)C)OCCCCCCCC/C=C\C/C=C\CCCCC]

and pharmaceutically acceptable salts thereof. In certain embodiments, the compositions and methods of the present invention include a cationic lipid, "HGT4004", having a compound structure of:

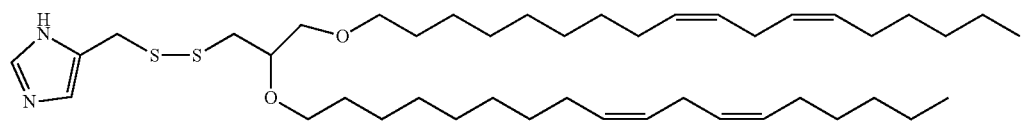

and pharmaceutically acceptable salts thereof. In certain embodiments, the compositions and methods of the present invention include a cationic lipid "HGT4005", having a compound structure of:

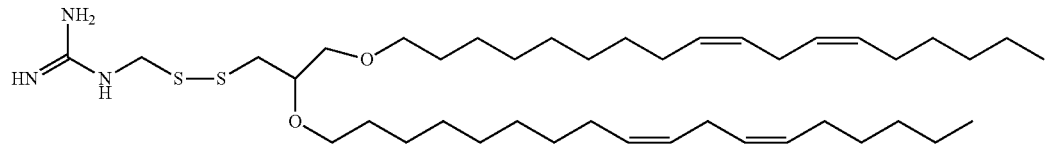 [SMILES: CCCCC/C=C\C/C=C\CCCCCCCCOCC(CSSCNC(=N)N)OCCCCCCCC/C=C\C/C=C\CCCCC]

and pharmaceutically acceptable salts thereof.

Other suitable cationic lipids for use in the compositions and methods of the present invention include cleavable cationic lipids as described in U.S. Provisional Application No. 62/672,194, filed May 16, 2018, and incorporated herein by reference. In certain embodiments, the compositions and methods of the present invention include a cationic lipid that is any of general formulas or any of structures (1a)-(21a) and (1b)-(21b) and (22)-(237) described in U.S. Provisional Application No. 62/672,194. In certain embodiments, the compositions and methods of the present invention include a cationic lipid that has a structure according to Formula (I'),

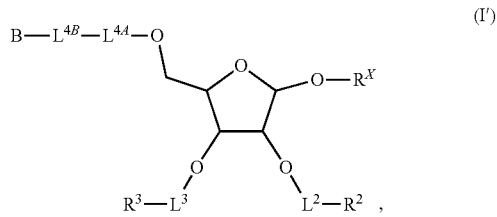

wherein:

$R^X$ is independently —H, -$L^1$-$R^1$, or -$L^{5A}$-$L^{5B}$-B';

each of $L^1$, $L^2$, and $L^3$ is independently a covalent bond, —C(O)—, —C(O)O—, —C(O)S—, or —C(O)$NR^L$—;

each $L^{4A}$ and $L^{5A}$ is independently —C(O)—, —C(O)O—, or —C(O)NR$^L$;

each $L^{4B}$ and $L^{5B}$ is independently $C_1$-$C_{20}$ alkylene; $C_2$-$C_{20}$ alkenylene; or $C_2$-$C_{20}$ alkynylene;

each B and B' is NR$^4$R$^5$ or a 5- to 10-membered nitrogen-containing heteroaryl;

each R$^1$, R$^2$, and R$^3$ is independently $C_6$-$C_{30}$ alkyl, $C_6$-$C_{30}$ alkenyl, or $C_6$-$C_{30}$ alkynyl;

each R$^4$ and R$^5$ is independently hydrogen, $C_1$-$C_{10}$ alkyl; $C_2$-$C_{10}$ alkenyl; or $C_2$-$C_{10}$ alkynyl; and each R$^L$ is independently hydrogen, $C_1$-$C_{20}$ alkyl, $C_2$-$C_{20}$ alkenyl, or $C_2$-$C_{20}$ alkynyl.

In certain embodiments, the compositions and methods of the present invention include a cationic lipid that is Compound (139) of 62/672,194, having a compound structure of:

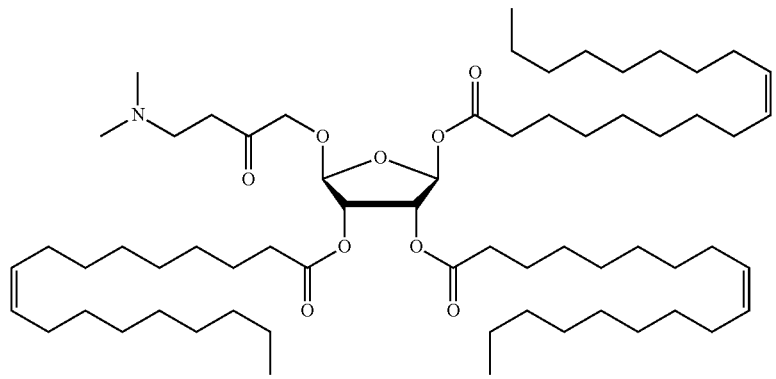

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido) ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylammonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethyl-1-(cis,cis-9',1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoylcarbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N,N-dimethyl-3-[(9Z, 12Z)-octadeca-9,12-dien-1-yloxy]propane-1-amine ("Octyl-CLinDMA"); (2R)-2-((8-[(3beta)-cholest-5-en-3-yloxy]octyl)oxy)-N, N-dimethyl-3-[(9Z, 12Z)-octadeca-9, 12-dien-1-yloxy]propan-1-amine ("Octyl-CLinDMA (2R)"); (2S)-2-((8-[(3P)-cholest-5-en-3-yloxy]octyl)oxy)-N, fsl-dimethyh3-[(9Z, 12Z)-octadeca-9, 12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z, 12Z)-octadeca-9,12-dien-1-yl)-1,3-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V. et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)—N,N-dimethyl-2,2-di((9Z, 12Z)-octadeca-9,12-dienyl)tetrahydro-3aH-cyclopenta[d] [1,3]dioxol-5-amine ("ALNY-100") and/or 4,7,13-tris(3-oxo-3-(undecylamino)propyl)-N1,N16-diundecyl-4,7,10, 13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle In some embodiments, sterol-based cationic lipids may be use instead or in addition to cationic lipids described herein. Suitable sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta [a]phenanthren-3-yl 3-(1H-imidazol-4-yl)propanoate, as represented by structure (I) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta [a]phenanthren-3-yl 3-(1H-imidazol-4-yl)propanoate, as represented by the following structure:

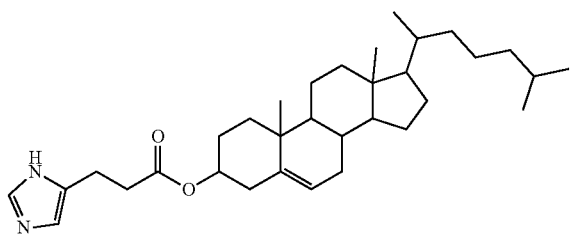 [SMILES: CC(C)CCCC(C)C1CCC2C3CC=C4CC(OC(=O)CCc5cnc[nH]5)CCC4(C)C3CCC12C]

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., ICE lipid) constitutes about 30%, about 35%, about 40%, about 45%, or about 50% of the liposome by molar ratio.

In some embodiments, cationic lipids constitute at least about 5%, 10%, 20%, 30%, 35%, 40%, 45%, 50%, 55%, 60%, 65%, or 70% of the total lipids in a suitable lipid solution by weight or by molar. In some embodiments, cationic lipid(s) constitute(s) about 30-70% (e.g., about 30-65%, about 30-60%, about 30-55%, about 30-50%, about 30-45%, about 30-40%, about 35-50%, about 35-45%, or about 35-40%) of the total lipid mixture by weight or by molar.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other excipients, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, the percentage of cholesterol-based lipid in the lipid nanoparticle may be greater than 5, %, 10%, greater than 20%, greater than 30%, or greater than 40%.

PEGylated Lipids

In some embodiments, provided liposomes comprise one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention in combination with one or more of the cationic and, in some embodiments, other lipids together which comprise the liposome. Contemplated PEG-modified lipids include, but are not limited to, a polyethylene glycol chain of up to 2 kDa, up to 3 kDa, up to 4 kDa or 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target cell, (Klibanov et al. (1990) FEBS Letters, 268 (1): 235-237), or they may be selected to rapidly exchange out of the formulation in vivo (see U.S. Pat. No. 5,885,613). In some embodiments, a PEG-modified or PEGylated lipid is PEGylated cholesterol or PEG-2K. In some embodiments, particularly useful exchangeable lipids are PEG-ceramides having shorter acyl chains (e.g., $C_{14}$ or $C_{18}$).

In some embodiments, particularly useful exchangeable lipids are PEG-ceramides having shorter acyl chains (e.g., $C_{14}$ or $C_{18}$). The PEG-modified phospholipid and derivatized lipids of the present invention may comprise a molar ratio from about 0% to about 15%, about 0.5% to about 15%, about 1% to about 15%, about 4% to about 10%, or about 2% of the total lipid present in the liposome. PEG-modified phospholipid and derivatized lipids may constitute at least about 5%, 10%, 20%, 30%, 40%, 50%, 60%, or 70% of the total lipids in a suitable lipid solution by weight or by molar. In some embodiments, PEGylated lipid lipid(s) constitute(s) about 30-50% (e.g., about 30-45%, about 30-40%, about 35-50%, about 35-45%, or about 35-40%) of the total lipids in a suitable lipid solution by weight or by molar.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the mRNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass polymer containing nanoparticles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

A suitable liposome for the present invention may include one or more of any of the cationic lipids, non-cationic lipids, cholesterol lipids, PEGylated lipids and/or polymers described herein at various ratios. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; or ICE, DOPE, cholesterol and DMG-PEG2K or ICE, DOPE and DMG-PEG2K. Additional combinations of lipids are described in the art, e.g., U.S. Ser. No. 62/420,421 (filed on Nov. 10, 2016), U.S. Ser. No. 62/421,021 (filed on Nov. 11, 2016), U.S. Ser. No. 62/464,327 (filed on Feb. 27, 2017), and PCT Application entitled "Novel ICE-based Lipid Nanoparticle Formulation for Delivery of mRNA," filed on Nov. 10, 2017, the disclosures of which are included here in their full scope by reference.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEGylated lipid(s) may be between about 30-60:25-35:20-30:1-15, respectively. In some embodiments, the ratio of cationic lipid(s) to non-cationic lipid(s) to cholesterol-based lipid(s) to PEGylated lipid(s) is approximately 40:30:20:10, respectively. In some embodiments, the ratio of cationic lipid(s) to non-cationic lipid(s) to cholesterol-based lipid(s) to PEGylated lipid(s) is approximately 40:30:25:5, respectively. In some embodiments, the ratio of cationic lipid(s) to non-cationic lipid(s) to cholesterol-based lipid(s) to PEGylated lipid(s) is approximately 40:32:25:3, respectively. In some embodiments, the ratio of cationic lipid(s) to non-cationic lipid(s) to cholesterol-based lipid(s) to PEGylated lipid(s) is approximately 50:25:20:5.

Formation of Liposomes

The liposomal transfer vehicles for use in the compositions of the invention can be prepared by various techniques, which are presently known in the art. The liposomes for use in provided compositions can be prepared by various techniques, which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then added to the vessel with a vortexing motion which results in the formation of MHLVs. Unilamellar vesicles (ULV) can then be formed by homogenization, sonication or extrusion of the multilamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (Zeta potential), targeting ligands and/or combinations thereof. In some embodiments, the one or more liposome may have a different composition of cationic lipids, neutral lipid, PEG-modified lipid and/or combinations thereof. In some embodiments the one or more liposomes may have a different molar ratio of cationic lipid, neutral lipid, cholesterol and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating an mRNA into a transfer vehicle, such as a liposome, is often to protect the nucleic acid from an environment, which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Liposome Size

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues. For example, a liposome may be sized such that its dimensions are larger than the fenestrations of the endothelial layer lining hepatic sinusoids to thereby limit distribution of the liposomes to hepatocytes.

In some embodiments, the size of a liposome is determined by the length of the largest diameter of the liposome particle. In some embodiments, a suitable liposome has a size no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, a suitable liposome has a size ranging from about 100-250 nm (e.g., ranging from about 100-225 nm, 100-200 nm, 100-175 nm, 100-150 nm). In some embodiments, a suitable liposome has a size ranging from about 10-100 nm (e.g., ranging from about 10-90 nm, 10-80 nm, 10-70 nm, 10-60 nm, or 10-50 nm). In a particular embodiment, a suitable liposome has a size less than about 100 nm.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Pharmaceutical Compositions

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

Provided liposomally-encapsulated or associated mRNAs, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject, the mammal, (e.g., treating, modulating, curing, preventing and/or ameliorating OTC deficiency). For example, a therapeutically effective amount may be an amount sufficient to achieve a desired therapeutic and/or prophylactic effect. Generally, the amount of a therapeutic agent (e.g., mRNA encoding a OTC protein) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

In some embodiments, the therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 90 mg/kg body weight, from about 0.005 mg/kg body weight to 80 mg/kg body weight, from about 0.005 mg/kg body weight to 70 mg/kg body weight, from about 0.005 mg/kg body weight to 60 mg/kg body weight, from about 0.005 mg/kg body weight to 50 mg/kg body weight, from about 0.005 mg/kg body weight to 40 mg/kg body weight, from about 0.005 mg/kg body weight to 30 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg body weight.

In some embodiments, the therapeutically effective dose is greater than about 0.1 mg/kg body weight, greater than about 0.5 mg/kg body weight, greater than about 1.0 mg/kg body weight, greater than about 3 mg/kg body weight, greater than about 5 mg/kg body weight, greater than about 10 mg/kg body weight, greater than about 15 mg/kg body weight, greater than about 20 mg/kg body weight, greater than about 30 mg/kg body weight, greater than about 40 mg/kg body weight, greater than about 50 mg/kg body weight, greater than about 60 mg/kg body weight, greater than about 70 mg/kg body weight, greater than about 80 mg/kg body weight, greater than about 90 mg/kg body weight, greater than about 100 mg/kg body weight, greater than about 150 mg/kg body weight, greater than about 200 mg/kg body weight, greater than about 250 mg/kg body weight, greater than about 300 mg/kg body weight, greater than about 350 mg/kg body weight, greater than about 400 mg/kg body weight, greater than about 450 mg/kg body weight, greater than about 500 mg/kg body weight. In a particular embodiment, the therapeutically effective dose is 1.0 mg/kg. In some embodiments, the therapeutically effective dose of 1.0 mg/kg is administered intramuscularly or intravenously.

A therapeutically effective dose can comprise a surprisingly low dose of the mRNA encoding an ornithine transcarbamylase protein. A therapeutically effective low dose also makes it possible for the drug to be available for pediatric administration. Moreover it was observed that using the methods of the invention, a therapeutically effective administration of the mRNA could be achieved at longer dosing intervals. In one embodiment, the therapeutically effective low dose can be administered to a subject at a dosing interval of one week or longer. In some embodiments, the dosing interval is two weeks or longer. In some embodiments, the dosing interval is three weeks or longer. In some embodiments, the dosing interval is two weeks or longer. In some embodiments, the dosing interval is four weeks or longer. In some embodiments, the dosing interval is five weeks or longer. In some embodiments, the dosing interval is six weeks or longer. In some embodiments, the dosing interval is seven weeks or longer. In some embodiments, the dosing interval is eight weeks or longer. In some embodiments, the dosing interval is nine weeks or longer. In some embodiments, the dosing interval is ten weeks or longer.

The present invention provides, among other things, a therapeutic low dose of 0.5 mg/kg or less of mRNA and at a dosing interval of once every two weeks or a longer dosing interval.

The low dose and the longer dosing interval was effective to reduce an ammonia level relative to a control level prior to the treatment, thereby providing a clear advantage of the present methods over methods requiring higher amounts of mRNA and at greater frequency of administration. Lower dose of mRNA could be associated with safety and tolerance parameters. This, coupled with longer dosing intervals lead to better compliance of the subject to whom the therapeutic composition is administered. Administration of the therapeutic composition to the subject in need thereof can be performed intravenously. In some embodiments, such administration can be performed subcutaneously. In some embodiments, such administration can be performed intramuscularly. In some embodiments, such administration can be performed intrathecally or by any means deemed suitable by one of skill in the art.

In some embodiments, the therapeutic low dose is 0.5 mg/kg or less of OTC-encoding mRNA. In some embodiments, the therapeutic low dose is 0.4 mg/kg or less of OTC-encoding mRNA. In some embodiments, the therapeutic low dose is 0.3 mg/kg or less of OTC-encoding mRNA. In some embodiments, the therapeutic low dose is 0.2 mg/kg or less of OTC-encoding mRNA. In some embodiments, the therapeutic low dose is 0.15 mg/kg of mRNA or less of OTC-encoding mRNA. In some embodiments, the therapeutic low dose is 0.10 mg/kg or less of OTC-encoding mRNA. In some embodiments, the therapeutic low dose is 0.05 mg/kg or less of OTC-encoding mRNA. In some embodiments, the therapeutic low dose is 0.03 mg/kg or less of OTC-encoding mRNA. In some embodiments, the therapeutic low dose is 0.01 mg/kg or less of OTC-encoding mRNA. In some embodiments, the therapeutic low dose is 0.001 mg/kg or less of OTC-encoding mRNA. In some embodiments, the therapeutic low dose is 0.005 mg/kg or less of OTC-encoding mRNA. In some embodiments, the low dose is 0.005 mg/kg of OTC-encoding mRNA.

In some embodiments, the therapeutic low dose is sufficient to maintain the reduced ammonia level in a tissue or a body fluid of the human for the period of the dosing interval or longer.

In some embodiments, the effective low dose of OTC encoding mRNA is suitable for administration to a pediatric subject. A pediatric subject may be about eighteen years of age or younger. A pediatric subject may be about fifteen, or about twelve, or about ten or about five or about two or about one year of age or younger.

The "effective dose or effective amount" for the purposes herein may be determined by such relevant considerations as are known to those of ordinary skill in experimental clinical research, pharmacological, clinical and medical arts.

A therapeutic low dose is a dose that is less than the maximal effective dose in the subject, but is a dose that shows therapeutic effectiveness. Determining a therapeutic low dose is important in developing a formulation into a drug. A therapeutic low dose may be higher than the minimal effective low dose. A therapeutic low dose may be in the range where the dose is optimally effective without causing any adverse effect.

In some embodiments, an effective therapeutic low dose is administered to the mammal wherein the therapeutic low dose of the pharmaceutical composition comprising an mRNA encoding ornithine transcarbamylase protein is administered at a dosing interval sufficient to reduce for the period of the dosing interval or longer the level of at least one symptom or biomarker associated with ornithine transcarbamylase deficiency in the mammal relative to its state prior to the treatment.

In some embodiments the mRNA encoding ornithine transcarbamylase protein is administered at a dose of 1 mg/kg or less of mRNA at a dosing interval of once every two weeks or a longer dosing interval, wherein the dose and dosing interval is sufficient to reduce for the period of the dosing interval or longer, the level of at least one symptom or biomarker associated with ornithine transcarbamylase deficiency in the mammal relative to the state prior to the treatment. In some embodiments the mRNA encoding ornithine transcarbamylase protein is administered at a dose of 0.5 mg/kg or less of mRNA. In some embodiments the mRNA encoding ornithine transcarbamylase protein is administered at a dose of 0.45 mg/kg or less of mRNA. In some embodiments the mRNA encoding ornithine transcarbamylase protein is administered at a dose of 0.40 mg/kg or less of mRNA. In some embodiments the mRNA encoding ornithine transcarbamylase protein is administered at a dose of 0.35 mg/kg or less of mRNA. In some embodiments the mRNA encoding ornithine transcarbamylase protein is administered at a dose of 0.30 mg/kg or less of mRNA. In some embodiments the mRNA encoding ornithine transcarbamylase protein is administered at a dose of 0.25 mg/kg or less. In some embodiments the mRNA encoding ornithine transcarbamylase protein is administered at a dose of 0.2 mg/kg or less.

In some embodiments the mRNA encoding ornithine transcarbamylase protein is administered at a dose of 0.15 mg/kg or less, administered at a dosing interval of once in 2 weeks or longer, and wherein the dose of 0.15 mg/kg or less at an interval of 2 weeks or longer reduces at least one symptom or the level of at least one biomarker associated with OTC deficiency in the mammal for the period of the dosing interval of 2 weeks or longer. In some embodiments the mRNA encoding ornithine transcarbamylase protein is administered at a dose of 0.125 mg/kg or less. In some embodiments the mRNA encoding ornithine transcarbamylase protein is administered at a dose of 0.10 mg/kg or less. In some embodiments the mRNA encoding ornithine transcarbamylase protein is administered at a dose of 0.09 mg/kg or less of mRNA, or at less than 0.08 mg/kg of mRNA, or at less than 0.07 mg/kg of mRNA, or at less than 0.06 mg/kg of mRNA, or at less than 0.05 mg/kg of mRNA, or at less than 0.04 mg/kg of mRNA, or at less than 0.03 mg/kg of mRNA, or at less than 0.02 mg/kg of mRNA, at less than 0.01 mg/kg of mRNA, or at 0.005 mg/kg of mRNA at a dosing interval sufficient to reduce the level of at least one symptom or biomarker associated with ornithine transcarbamylase deficiency in the mammal relative to the state prior to the treatment.

In some embodiments, the therapeutic low dose of the pharmaceutical composition comprising mRNA encoding ornithine transcarbamylase protein is 0.01 mg/kg of mRNA at a dosing interval sufficient to reduce the level of at least one symptom or biomarker associated with ornithine transcarbamylase deficiency in the mammal relative to the state prior to the treatment.

In some embodiments, the therapeutic low dose of the pharmaceutical composition comprising mRNA encoding ornithine transcarbamylase protein is about 0.005 mg/kg of mRNA at a dosing interval of once every 2 weeks or longer, wherein the level of at least one symptom or biomarker associated with ornithine transcarbamylase deficiency in the mammal is reduced at maintained at a reduced level relative to the state prior to the treatment for the period of the dosing interval or longer.

In some embodiments the mammal is a human. A suitable therapeutic dose that may be applicable for a human being can be derived based on animal studies. A basic guideline for deriving a human equivalent dose from studies performed in animals can be obtained from the U.S>Food and Drug Administration (FDA) website at www.fda.gov/downloads/drugs/guidances/ucm078932.pdf, entitled, "Guidance for Industry Estimating the Maximum Safe Starting Dose in Initial Clinical Trials for Therapeutics in Adult Healthy Volunteers." Based on the guidelines for allometric scaling, a suitable dose of, for example, 0.6 mg/kg in a mouse (as shown in Example 2), would relate to a human equivalent dose of 0.0048 mg/kg. Thus, considering the derived human equivalent dose, a projected human therapeutic dose can be derived based on studies in other animals.

In some embodiments, the projected human therapeutic low dose of the pharmaceutical composition comprising mRNA encoding ornithine transcarbamylase protein is about 0.005 mg/kg of mRNA at a dosing interval of once every 2 weeks or longer, wherein the level of at least one symptom or biomarker associated with ornithine transcarbamylase deficiency in the mammal is reduced at maintained at a reduced level relative to the state prior to the treatment for the period of the dosing interval or longer. In some embodiments, the projected human therapeutic low dose of the pharmaceutical composition comprising mRNA encoding ornithine transcarbamylase protein is about 0.001 mg/kg of mRNA or higher. In some embodiments, the projected human therapeutic low dose of the pharmaceutical composition comprising mRNA encoding ornithine transcarbamylase protein is about 0.002 mg/kg of mRNA or higher. In some embodiments, the projected human therapeutic low dose of the pharmaceutical composition comprising mRNA encoding ornithine transcarbamylase protein is about 0.003 mg/kg of mRNA or higher. In some embodiments, the projected human therapeutic low dose of the pharmaceutical composition comprising mRNA encoding ornithine transcarbamylase protein is about 0.004 mg/kg of mRNA or higher. In some embodiments, the projected human therapeutic low dose of the pharmaceutical composition comprising mRNA encoding ornithine transcarbamylase protein is about 0.005 mg/kg of mRNA or higher.

In some embodiments, the dosing interval is once every 15 days or longer, or once every 20 days or longer, or once every 21 days, or once every 22 days, or once every 23 days, or once every 24 days, or once every 25 days, once every 26 days, or once every 27 days, or once every 28 days, or once every 29 days or longer, or once every 30 days or longer, or once every 31 days or longer. In some embodiments, the dosing interval is once every 40, 45 or 50 days or 60 days, or any number of days in between. In some embodiments, the dosing interval is once every 80, 90 or 120 days or 150 days, or any number of days in between.

In some embodiments, the therapeutic low dose is administered at a dosing interval of once every 2 weeks or longer, which is sufficient to reduce the level of at least one symptom or biomarker associated with ornithine transcarbamylase deficiency in the mammal relative to the state prior to the treatment. In some embodiments, the therapeutic low dose is administered at a dosing interval of once every 3 weeks or longer, which is sufficient to reduce the level of at least one symptom or biomarker associated with ornithine transcarbamylase deficiency in the mammal relative to the state prior to the treatment. In some embodiments, the dosing interval is once every 4 weeks or longer. In some embodiments, the dosing interval is once every 5 weeks or longer. In some embodiments, the dosing interval is once every 6 weeks or longer. In some embodiments, the dosing interval is once every 8 weeks or longer. In some embodiments, the dosing interval is once every 12 or 15 or 18 weeks or longer.

In some embodiments, the dosing interval is once a month. In some embodiments, the dosing interval is once in every two months. In some embodiments, the dosing interval is once every three months, or once every four months or once every five months or once every six months or anywhere in between.

In some embodiments, administering the provided composition results in an increased OTC mRNA expression level in a biological sample from a subject as compared to a baseline expression level before treatment. Typically, the baseline level is measured immediately before treatment. Biological samples include, for example, whole blood, serum, plasma, urine and tissue samples (e.g., muscle, liver, skin fibroblasts). In some embodiments, administering the provided composition results in an increased OTC mRNA expression level by at least about 10%, 20%, 30%, 40%, 50%, 60%, 70%, 80%, 90%, or 95% as compared to the baseline level immediately before treatment. In some embodiments, administering the provided composition results in an increased OTC mRNA expression level as compared to an OTC mRNA expression level in subjects who are not treated.

According to the present invention, a therapeutically effective dose of the provided composition, when administered regularly, results in an increased OTC protein expression or activity level in a subject as compared to a baseline OTC protein expression or activity level before treatment. Typically, the OTC protein expression or activity level is measured in a biological sample obtained from the subject such as blood, plasma or serum, urine, or solid tissue extracts. The baseline level is measured immediately before treatment. In some embodiments, administering the provided composition results in an increased OTC protein expression or activity level in a biological sample (e.g., plasma/serum or urine) by at least about 10%, 20%, 30%, 40%, 50%, 60%, 70%, 80%, 90%, or 95% as compared to a baseline level before treatment. In some embodiments, administering the provided composition results in an increased OTC protein expression or activity level in a biological sample (e.g., plasma/serum or urine) by at least about 10%, 20%, 30%, 40%, 50%, 60%, 70%, 80%, 90%, or 95% as compared to a baseline level before treatment for at least 24 hours, at least 48 hours, at least 72 hours, at least 3 days, at least 4 days, at least 5 days, at least 6 days, at least 7 days, at least 8 days, at least 9 days, at least 10 days, at least 11 days, at least 12 days, at least 13 days, at least 14 days, or at least 15 days.

In some embodiments, the therapeutic low dose is sufficient to achieve at least some stabilization, improvement or elimination of symptoms and other indicators, such as biomarkers, are selected as appropriate measures of disease progress, regression or improvement by those of skill in the art. For example, a suitable amount and dosing regimen is one that causes at least transient protein (e.g., enzyme) production. In some embodiments, the symptom comprises hyperammonemia. Hyperammonemia is a condition involving excess accumulation of ammonia in the tissue or body fluids. This is caused, in the context of OTC deficiency, by the lack of conversion of ammonia to citrulline, owing to lack of the functional enzyme ornithine transcarbamylase.

In some embodiments, the therapeutic low dose is sufficient to reduce the level of one or more biomarkers of the disease related to OTC deficiency for at least the period of the dosing interval, compared to a level prior to the initial administration of the therapeutic composition. In some embodiments, the biomarker is plasma ammonia accumulation level. In some embodiments, the biomarker is urinary orotic acid. In some embodiments, the biomarker is selected from a group comprising: plasma ammonia accumulation, tissue ammonia accumulation, urinary orotic acid, serum glutamate, brain myoinositol and serum amino acids.

Typically, the orotic acid, ammonia or glutamine level before or after the treatment may be measured in a biological sample obtained from the subject such as, blood, plasma, serum, urine, or solid tissue extracts. The baseline orotic acid, ammonia or glutamine level is measured immediately before treatment. In some embodiments, treatment according to the present invention results in an reduction of the orotic acid, ammonia, or glutamine level in a biological sample (e.g., blood, serum, or urine) obtained from the subject by at least 10%, 20%, 30%, 40%, 50%, 60%, 70%, 80%, 90%, or 95% as compared to the baseline orotic acid, ammonia, or glutamine level, respectively.

In some embodiments, ammonia levels are measured before and after the treatment from blood plasma. In some embodiments, ammonia levels are measured before and after the treatment from tissues. In some embodiments, ammonia levels are measured before and after the treatment from the liver. In some embodiments, ammonia levels are measured before and after the treatment from the brain.

In some embodiments, the therapeutically effective dose is sufficient to reduce and maintain reduced ammonia level in the tissue or a body fluid of the subject for the period of the therapeutic interval or longer.

In some embodiments, the therapeutically effective dose is such that a single administration of the pharmaceutical preparation is sufficient to reduce and maintain reduced ammonia level in the tissue or a body fluid of the subject relative to a level prior to the treatment for about 6 months.

In some embodiments, the therapeutically effective dose is such that a single administration of the pharmaceutical preparation is sufficient to reduce and maintain reduced ammonia level in the tissue or a body fluid of the subject relative to a level prior to the treatment for about 4 months.

In some embodiments, the therapeutically effective dose is such that a single administration of the pharmaceutical preparation is sufficient to reduce and maintain reduced ammonia level in the tissue or a body fluid of the subject relative to a level prior to the treatment for about 2 months. In some embodiments, the therapeutically effective dose is such that a single administration of the pharmaceutical preparation is sufficient to reduce and maintain reduced ammonia level in the tissue or a body fluid of the subject relative to a level prior to the treatment for at least about 8 weeks, or for about 7 weeks, or for about 6 weeks, or for about 5 weeks or for about 4 weeks.

In some embodiments, the therapeutically effective dose of the pharmaceutical composition is sufficient to reduce and maintain the plasma ammonia level of the administered mammalian subject at less than 1000 micromol/L for the period of dosing interval or longer. In some embodiments, the plasma ammonia level of the administered mammalian subject at reduced to and maintained at less than 800 micromol/L, or to less than 500 micromol/L for the period of dosing interval or longer. In some embodiments, the plasma ammonia level of the administered mammalian subject at reduced to and maintained at less than 400 micromol/L for the period of dosing interval or longer. In some embodiments, the plasma ammonia level of the administered mammalian subject at reduced to and maintained at less than 300 micromol/L for the period of dosing interval or longer. In some embodiments, the plasma ammonia level of the subject at reduced to and maintained at less than 250 micromol/L for the period of dosing interval. In some embodiments, the plasma ammonia level of the administered mammalian subject at reduced to and maintained at less than 200 micromol/L for the period of dosing interval or longer. In some embodiments, the plasma ammonia level of the administered mammalian subject at reduced to and maintained at less than 180 micromol/L, or less than 150 micromol/L, or less than 140 micromol/L, or less than 130 micromol/L, or less than 120 micromol/L, or less than 110 micromol/L, or less than 100 micromol/Liter, or less than 90 micromol/L, or less than 80 micromol/Liter, or less than 70 micromol/L, or less than 60 micromol/Liter, or less than 50 micromol/L, or less than 30 micromol/Liter for the period of dosing interval or longer. In some embodiments, a therapeutically mRNA composition, when administered regularly, reduces the plasma ammonia level of the subject at less than 50 micromol/L. In some embodiments, a therapeutically mRNA composition, when administered at the dosing interval, reduces and maintains the plasma ammonia level of the mammal at less than 30 micromol/L.

In some embodiments, a single administration of the pharmaceutical preparation at the low therapeutic dose is sufficient to reduce the plasma ammonia accumulation level of the administered mammalian subject to less than 100 micromol/L or less for the period of the therapeutic interval or longer.

In some embodiments, a single administration of the pharmaceutical preparation at the low therapeutic dose is sufficient to reduce the plasma ammonia accumulation level of the administered mammalian subject to less than 50 micromol/L or less, for period of the therapeutic interval or longer.

In some embodiments, a therapeutically effective dose of the provided composition, when administered regularly, results in decreased plasma ammonia level in a subject as compared to a baseline, which is the level of ammonia prior to any treatment. In some embodiments the plasma ammonia level is decreased by at least 10%, or by at least 20%. In some embodiments the plasma ammonia may be reduced by 30-50%.

In some embodiments, the therapeutically effective dose is such that a single administration of the pharmaceutical preparation is sufficient to reduce and maintain reduced urinary orotic acid level of the mammalian subject relative to a level prior to the treatment for the period of the dosing interval or longer. In some embodiments, the orotic acid level is reduced to and maintained at less than 2 mmol/mol creatinine. In some embodiments, the orotic acid level is reduced to and maintained at less than 1.8 mmol/mol creatinine. In some embodiments, the orotic acid level is reduced to and maintained at less than 1.7 mmol/mol creatinine. In some embodiments, the orotic acid level is reduced to and maintained at less than 1.6 mmol/mol creatinine. In some embodiments, the orotic acid level is reduced to and maintained at less than 1.5 mmol/mol creatinine. In some embodiments, the orotic acid level is reduced to and maintained at less than 1.4 mmol/mol creatinine. In some embodiments, the orotic acid level is reduced to and maintained at less than 1.3 mmol/mol creatinine. In some embodiments, the orotic acid level is reduced to and maintained at less than 1.2 mmol/mol creatinine. In some embodiments, the orotic acid level is reduced to and maintained at less than 1 mmol/mol creatinine. In some embodiments, the orotic acid level is reduced to and maintained at less than 0.8 mmol/mol creatinine. In some embodiments, the orotic acid level is reduced to and maintained at less than 0.5 mmol/mol creatinine for the period of the dosing interval or longer.

In some embodiments, the therapeutically effective dose is such that a single administration of the pharmaceutical preparation is sufficient to reduce and maintain reduced urinary the orotic acid level at less than 1.5 mmol/mol creatinine for the period of the dosing interval or longer.

In some embodiments, the therapeutically effective dose is such that a single administration of the pharmaceutical preparation is sufficient to reduce plasma glutamate levels to less than 750 microliters/L. In some embodiments, the therapeutically effective dose is such that a single administration of the pharmaceutical preparation is sufficient to reduce plasma glutamate levels to less than 700 microliters/L, or less than 600 microliters/L, or less than 500 microliters/L, or less than 400 microliters/L, or less than 300 microliters/L.

In some embodiments, a therapeutically effective dose of the provided composition, when administered regularly, results in an increased citrulline production in a subject as compared to a baseline citrulline production before treatment. Typically, the citrulline level before or after the treatment may be measured in a biological sample obtained from the subject such as, blood, plasma or serum, urine, or solid tissue extracts. In some embodiments, treatment according to the present invention results in an increase of the citrulline level in a biological sample (e.g., plasma, serum, or urine) by at least 10%, 20%, 30%, 40%, 50%, 60%, 70%, 80%, 90%, 1-fold, 1.5-fold, 2-fold, 2.5-fold, or 3-fold as compared to the base line citrulline level, respectively.

In some embodiments, plasma citrulline level is increased to a detectable level in the mammal, following treatment with a single dose of low dose of the therapeutic composition. In some embodiments, the plasma citrulline level become detectable in the plasma of the following one or more administrations of the therapeutic composition. In some embodiments, plasma citrulline level is increased to 5 μM following treatment with the therapeutic composition. In some embodiments, plasma citrulline level is increased to 10 μM, or 15, or 20 or 30 or 40 μM or 50 μM, following treatment with the therapeutic composition. In some embodiments, administering the provided composition results in an increased OTC protein level in the liver of a subject as compared to a baseline level before treatment. Typically, the baseline level is measured immediately before treatment. In some embodiments, administering the provided composition results in an increased ornithine transcarbamylase protein level in the liver by at least about 10%, 20%, 30%, 40%, 50%, 60%, 70%, 80%, 90%, or 95% as compared to a baseline level before treatment. In some embodiments, administering the provided composition results in an increased ornithine transcarbamylase protein level in the liver as compared to a ornithine transcarbamylase protein level in the liver of subjects who are not treated.

In some embodiments, the urinary orotidic acid level is reduced to less than 1.5 mmol/mol creatinine.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal.

In some embodiments, the therapeutically effective dose comprising the mRNA encoding ornithine transcarbamylase protein is administered to the mammal by intravenous administration.

In some embodiments, the therapeutically effective dose comprising the mRNA encoding ornithine transcarbamylase protein is administered to the mammal by intramuscular administration.

In some embodiments, the therapeutically effective dose comprising the mRNA encoding ornithine transcarbamylase protein is administered to the mammal by subcutaneous administration.

In particular embodiments, the intramuscular administration is to a muscle selected from the group consisting of skeletal muscle, smooth muscle and cardiac muscle. In some embodiments the administration results in delivery of the mRNA to a muscle cell. In some embodiments the administration results in delivery of the mRNA to a hepatocyte (i.e., liver cell). In a particular embodiment, the intramuscular administration results in delivery of the mRNA to a muscle cell.

Alternatively or additionally, liposomally encapsulated mRNAs and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

In particular embodiments, OTC encoding mRNA is administered intravenously, wherein, intravenous administration is associated with delivery of the mRNA to hepatocytes.

In some embodiments, the therapeutically effective dose comprising the mRNA encoding ornithine transcarbamylase protein is administered for suitable delivery to the mammal's liver. In some embodiments, the therapeutically effective dose comprising the mRNA encoding ornithine transcarbamylase protein is administered for suitable expression in hepatocytes of the administered mammal.

Provided methods of the present invention contemplate single as well as multiple administrations of a therapeutically effective amount of the therapeutic agents (e.g., mRNA encoding an OTC protein) described herein. Therapeutic agents can be administered at regular intervals, depending on the nature, severity and extent of the subject's condition (e.g., OTC deficiency). In some embodiments, a therapeutically effective amount of the therapeutic agents (e.g., mRNA encoding an OTC protein) of the present invention may be administered intrathecally periodically at regular intervals (e.g., once every year, once every six months, once every five months, once every three months, bimonthly (once every two months), monthly (once every month), biweekly (once every two weeks), twice a month, once every 30 days, once every 28 days, once every 14 days, once every 10 days, once every 7 days, weekly, twice a week, daily or continuously).

In some embodiments, provided liposomes and/or compositions are formulated such that they are suitable for extended-release of the mRNA contained therein. Such extended-release compositions may be conveniently administered to a subject at extended dosing intervals. For example, in one embodiment, the compositions of the present invention are administered to a subject twice a day, daily or every other day. In one embodiment, the compositions of the present invention are administered to a subject twice a week, once a week, once every 7 days, once every 10 days, once every 14 days, once every 28 days, once every 30 days, once every two weeks, once every three weeks, or more preferably once every four weeks, once a month, twice a month, once every six weeks, once every eight weeks, once every other month, once every three months, once every four months, once every six months, once every eight months, once every nine months or annually. Also contemplated are compositions and liposomes which are formulated for depot administration (e.g., intramuscularly, subcutaneously, intravitreally) to either deliver or release an mRNA over extended periods of time. Preferably, the extended-release means employed are combined with modifications made to the mRNA to enhance stability.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts. According to the present invention, a therapeutically effective dose of the provided composition, when administered regularly, results in at least one symptom or feature of the OTC deficiency is reduced in intensity, severity, or frequency or has delayed onset.

Also contemplated herein are lyophilized pharmaceutical compositions comprising one or more of the liposomes disclosed herein and related methods for the use of such compositions as disclosed for example, in International Patent Application PCT/US12/41663, filed Jun. 8, 2012, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the OTC mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered. Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

According to various embodiments, the timing of expression of delivered mRNAs can be tuned to suit a particular medical need. In some embodiments, the expression of the protein encoded by delivered mRNA is detectable 1, 2, 3, 6, 12, 24, 48, 72, 96 hours, 1 week, 2 weeks, or 1 month after administration of provided liposomes and/or compositions.

In some embodiments, a therapeutically effective dose of the provided composition, when administered regularly, results in a reduced glutamine level in a subject as compared to a baseline glutamine level before treatment.

In some embodiments, administering the provided composition results in an increased level of OTC protein in a liver cell (e.g., a hepatocyte) of a subject as compared to a baseline level before treatment. Typically, the baseline level is measured immediately before treatment. In some embodiments, administering the provided composition results in an increased OTC protein level in the liver cell by at least about 10%, 20%, 30%, 40%, 50%, 60%, 70%, 80%, 90%, or 95% as compared to a baseline level before treatment. In some embodiments, administering the provided composition results in an increased OTC protein level in a liver cell as compared to the OTC protein level a liver cell of subjects who are not treated.

In some embodiments, administering the provided composition results in an increased OTC protein level in plasma or serum of subject as compared to a baseline level before treatment. Typically, the baseline level is measured immediately before treatment. In some embodiments, administering the provided composition results in an increased OTC protein level in plasma or serum by at least about 10%, 20%, 30%, 40%, 50%, 60%, 70%, 80%, 90%, or 95% as compared to a baseline level before treatment. In some embodiments, administering the provided composition results in an increased OTC protein level in plasma or serum as compared to an OTC protein level in plasma or serum of subjects who are not treated.

In some embodiments, administering the provided composition results in increased OTC enzyme activity in a biological sample from a subject as compared to the baseline level before treatment. Typically, the baseline level is measured immediately before treatment. Biological samples include, for example, whole blood, serum, plasma, urine and tissue samples (e.g., liver). In some embodiments, administering the provided composition results in an increased OTC enzyme activity by at least about 10%, 20%, 30%, 40%, 50%, 60%, 70%, 80%, 90%, or 95% as compared to a baseline level immediately before treatment. In some embodiments, administering the provided composition results in an increased OTC enzyme activity as compared to OTC enzyme activity in subjects who are not treated.

In some embodiments the subject is a mammal. In some embodiments, the mammal is an adult. In some embodiments the mammal is an adolescent. In some embodiments the mammal is an infant or a young mammal. In some embodiments, the mammal is a primate. In some embodiments the mammal is a human. In some embodiments the subject is 6 years to 80 years old.

Liposome Formulations for OTC mRNA Delivery and Expression

This example provides exemplary liposome formulations for effective delivery and expression of OTC mRNA in vivo.

Lipid Materials

The formulations described herein include a multi-component lipid mixture of varying ratios employing one or more cationic lipids, helper lipids (e.g., non-cationic lipids and/or cholesterol-based lipids) and PEGylated lipids designed to encapsulate mRNA encoding OTC protein. Cationic lipids can include (but not exclusively) DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869), cKK-E12 (3,6-bis(4-(bis(2-hydroxydodecyl)amino)butyl)piperazine-2,5-dione), HGT5000, HGT5001, HGT4003, ICE, OF-02, dialkylamino-based, imidazole-based, guanidinium-based, etc. Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (2-dioleoyl-sn-glycero-3-phospho-(1'-rac-glycerol)), cholesterol, etc. The PEGylated lipids can include (but not exclusively) a poly(ethylene) glycol chain of up to 5 kDa in length covalently attached to a lipid with alkyl chain(s) of $C_6$-$C_{20}$ length.

Exemplary Formulation Protocols

A. cKK-E12

Aliquots of 50 mg/mL ethanolic solutions of cKK-E12, DOPE, cholesterol and DMG-PEG2K were mixed and diluted with ethanol to 3 mL final volume. Separately, an aqueous buffered solution (10 mM citrate/150 mM NaCl, pH 4.5) of OTC mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. The final concentration, $Z_{ave}$, $Dv_{(50)}$ and $Dv_{(90)}$ of the OTC encapsulated mRNA were determined.

B. C12-200

Aliquots of 50 mg/mL ethanolic solutions of C12-200, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the OTC encapsulated mRNA are determined.

C. HGT4003

Aliquots of 50 mg/mL ethanolic solutions of HGT4003, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the OTC encapsulated mRNA are determined.

D. ICE

Aliquots of 50 mg/mL ethanolic solutions of ICE, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the OTC encapsulated mRNA are determined.

E. HGT5001

Aliquots of 50 mg/mL ethanolic solutions of HGT5001, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the OTC encapsulated mRNA are determined.

F. HGT5000

Aliquots of 50 mg/mL ethanolic solutions of HGT5000, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the OTC encapsulated mRNA are determined.

G. DLinKC2DMA

Aliquots of 50 mg/mL ethanolic solutions of DLinKC2DMA, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the OTC encapsulated mRNA are determined.

H. DODAP

Aliquots of 50 mg/mL ethanolic solutions of DODAP, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the OTC encapsulated mRNA are determined.

I. DODMA

Aliquots of 50 mg/mL ethanolic solutions of DODMA, DOPE, cholesterol and DMG-PEG2K are mixed and diluted with ethanol to 3 mL final volume. Separately, an aqueous buffered solution (10 mM citrate/150 mM NaCl, pH 4.5) of OTC mRNA is prepared from a 1 mg/mL stock. The lipid solution is injected rapidly into the aqueous mRNA solution and shaken to yield a final suspension in 20% ethanol. The resulting nanoparticle suspension is filtered, diafiltrated with 1×PBS (pH 7.4), concentrated and stored at 2-8° C. The final concentration, $Z_{ave}$, $Dv_{(50)}$ and $Dv_{(90)}$ of the OTC encapsulated mRNA are determined.

Clinical or therapeutic candidate mRNA formulations are selected from the exemplary codon-optimized mRNA sequences having a 5'-cap and a 3'-poly A tail, which is formulated in a suitable lipid combination as described above. Clinical relevant mRNA candidates are characterized by efficient delivery and uptake by in vivo tissue, high level of expression and sustained protein production, without detectable adverse effects in the subject to whom the therapeutic is administered, either caused by the pharmacologically active ingredient or by the lipids in the nanoparticle, or by any excipients used in the formulation. In general, high efficiency with low dose administration is favorable for the selection process of a relevant candidate therapeutic.

EXAMPLES

While certain compounds, compositions and methods of the present invention have been described with specificity in accordance with certain embodiments, the following examples serve only to illustrate the compounds of the invention and are not intended to limit the same.

Example 1. Low-Dose OTC mRNA Provides Two Weeks and Longer hOTC Protein Production, hOTC Protein Activity, and Maintained Reduction of Hyperammonemia The study described in this example shows that a single low-dose (e.g., 0.15 mg/kg) of hOTC mRNA delivered in a lipid nanoparticle formulation provides sustained presence of hOTC mRNA, sustained expression of hOTC protein, sustained activity of that hOTC protein, and a sustained reduction of a hyperammonemic state for up to and at least for two weeks (i.e., at least 15 days following administration), for up to and at least for three weeks (i.e., at least 22 days following administration), and for up to and at least for four weeks (i.e., at least 29 days following administration).

Study Design and Assessments

As outlined in the experimental design in Table 2 below, 30 female spf$^{ash}$ mice (KO) were randomized into five cohorts (Groups 2-6) and on Day 1 were administered hOTC mRNA in a lipid nanoparticle formulation at a dose of 0.15 mg/kg of mRNA (Groups 3-6) or buffer (Group 2, Untreated). At each timepoint of Day 8 (Week 1), Day 15 (Week 2), Day 22 (Week 3) and Day 29 (Week 4) following administration, a treated cohort (one of Groups 3-6) was removed for assessment of liver hOTC mRNA and protein levels, hOTC protein activity, and response to ammonia challenge. The control cohort (Group 2) was removed on Day 8 for the same assessments. As a reference control, a group of six wild-type mice (Group 1) was treated with buffer on Day 1 and then removed on Day 8 for the same assessments. All doses were administered at 5.0 mL/kg via tail vein injection.

TABLE 2

| Group No. | Animals (type) | Treatment | mRNA Dose | Dose Volume | Dose Regimen | Timepoint of Cohort Removal | Assessments Performed |
| --- | --- | --- | --- | --- | --- | --- | --- |
| 1 | 6 (WT) | Buffer | 0.0 | 5.0 mL/kg | Day 1 Only | On Day 8 | hOTC mRNA and protein level; citrulline and urinary orotic acid as hOTC protein activity |
| 2 | 6 (KO) | Buffer | 0.0 | | | On Day 8 | |
| 3 | 6 (KO) | hOTC | 0.15 | | | On Day 8 | |
| 4 | 6 (KO) | mRNA | mg/kg | | | On Day 15 | |
| 5 | 6 (KO) | LNP | | | | On Day 22 | |

TABLE 2-continued

| Group No. | Animals (type) | Treatment | mRNA Dose | Dose Volume | Dose Regimen | Timepoint of Cohort Removal | Assessments Performed |
|---|---|---|---|---|---|---|---|
| 6 | 6 (KO) | | | | | | On Day 29 measures; and NH$_4$Cl challenge and plasma NH$_3$ measure |

No. = number;
WT = wild type;
KO = knockout;
LNP = lipid nanoparticle formulation For each removed cohort at each timepoint, animals were subjected to an ammonia challenge after which blood, urine and tissue samples were collected. The assessments of liver hOTC mRNA and protein levels, hOTC protein activity and response to ammonia challenge were conducted as described below.

Liver hOTC mRNA and protein levels. Mouse liver samples were homogenized using a HEPES lysis buffer and freeze/thawed twice to ensure total cell lysis. Debris was pelleted, and supernatant was collected. The hOTC mRNA levels were determined using qPCR. Briefly, flanking forward and reverse primers, which bind to complementary sequence regions within the target sequence (hOTC), were added to the reaction mixture and annealed to the target sequence present in the sample and to standards. A TaqMan fluorogenic probe then was annealed sequence-specifically between primer sites. Successive cycles of template denaturation, primer-annealing and product extension amplified the target sequence to provide a fluorescence signal that was quantified by reference to the standards, with the mRNA being measured in copies of OTC per microgram of total mRNA. The hOTC protein levels were determined by ELISA, using an anti-OTC antibody coated onto a Nunc MaxiSorb plate at 1 g/mL for 1 hour in 50 mM sodium bicarbonate solution, pH 9.6. The plate was washed using DPBS and Tween-20 wash buffer, then blocked 1 hour with Surmodics casein blocking buffer. The plates were again washed, and then samples and standard were added in duplicate and incubated for an additional hour. The plate was washed and then HRP-conjugated detection Ab (21C02) was added to the plate at a 1:5500 dilution and incubated for 1 hour. After a final wash, the plate was developed using Surmodics TMB substrate, stopped with 1N HCl and read at 450 nm minus 650 nm on a spectrophotometer.

hOTC protein activity—citrulline measurement. The production of citrulline can be used to evaluate the activity of OTC protein. For the citrulline measurements conducted in this study, mouse liver homogenate was prepared and diluted in 1×DPBS then added into UltraPure water. Citrulline standard was added in predetermined amounts to serve as an internal reference. A reaction mix containing carbamoyl phosphate, ornithine and triethanolamine was added and the reaction was allowed to proceed at 37° C. for 30 minutes. The reaction was stopped with a mix of phosphoric and sulfuric acid, and diacetylmonoxime was added. The sample was incubated at 85 degrees Celsius for 30 minutes, cooled briefly, and read at 490 nm to quantify the citrulline against the citrulline standard. Citrulline was measured as μmol citrulline/hr/mg of total protein.

hOTC protein activity—urinary orotic acid assessment. For the urinary orotic acid measurements, orotic acid quantification from animal urine samples was performed via Ultra Performance Liquid Chromatography (UPLC) using an ion exchange column. Briefly, urine samples were diluted two-fold using RNase-free water and a portion was loaded onto a ThermoScientific 100× column. The mobile phase comprising acetonitrile and 25 mM ammonium acetate afforded separation and quantification of orotic acid with detection based on absorbance at 280 nm.

Response to ammonia challenge. With reference to FIG. 1, for the ammonia challenge and resulting plasma ammonia measurements, ammonium chloride was administered at 5 mmol/kg (at 25 mL/kg) via a single intraperitoneal injection. At 40 minutes post ammonium chloride challenge, all animals were euthanized with $CO_2$ asphyxiation followed by terminal blood collection via cardiac puncture. Approximately 80 μL of the blood sample collected at euthanasia were collected into lithium heparin tubes, processed to plasma and analyzed immediately (within two hours of collection) for ammonia ($NH_3$) levels by an IDEXX Catalyst Dx analyzer at the Testing Facility. Plasma ammonia in response to the ammonia challenge was measured in μmol/L.

Results

The results of this study surprisingly show that a single dose of 0.15 mg/kg of hOTC mRNA provides for the sustained presence of hOTC mRNA, the sustained expression of hOTC protein, and the sustained activity of that hOTC protein, for up to and at least two weeks (i.e., at least 15 days following administration), for up to and at least three weeks (i.e., at least 22 days following administration), and for up to and at least four weeks (i.e., at least 29 days following administration).

Figure 2:
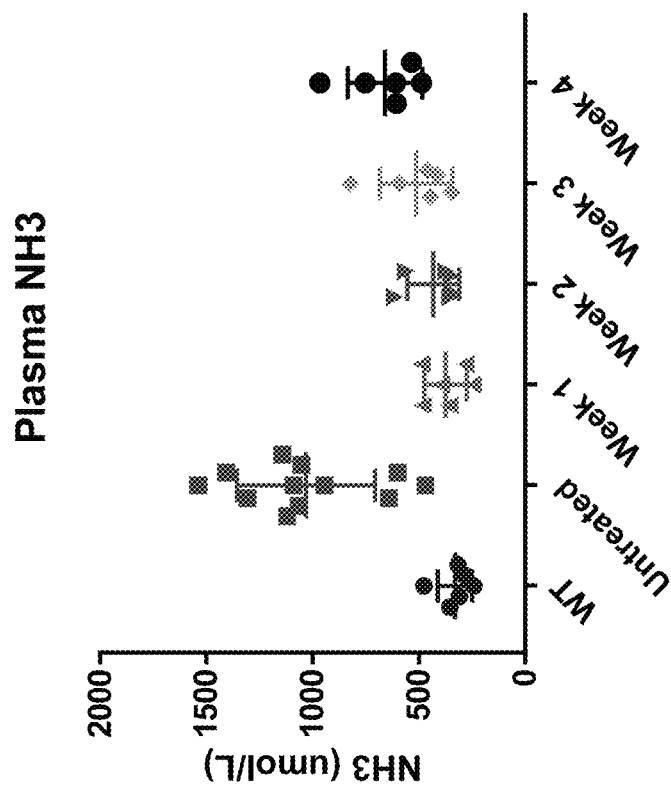
FIG. 2 is a graph that depicts reduction in and maintained reduction of ammonia levels (i.e., a hyperammonemic state) following hOTC mRNA administration in the assay outlined in FIG. 1 for the timepoints shown.

In particular, a low-dose of 0.15 mg/kg hOTC mRNA (e.g., 0.15 mg/kg) provided protection against ammonia in an animal deficient in OTC for up to and at least two weeks (i.e., at least 15 days following administration), for up to and at least three weeks (i.e., at least 22 days following administration), and for up to and at least four weeks (i.e., at least 29 days following administration). FIG. 2 depicts the results of animals treated at Day with 0.15 mg/kg mRNA in a lipid nanoparticle formulation and then challenged at 8 days (Week 1), 15 days (Week 2), 22 days (Week 3), or 29 days (Week 4) following treatment with ammonia to assess the duration of protection from the treatment. As shown in FIG. 2, as compared to untreated control animals, the treated animals maintained protection against ammonia challenge at all timepoints out to 20 days following administration. This surprisingly shows that in animals having compromised OTC function, low doses of hOTC mRNA in a lipid nanoparticle formulation, e.g., doses less than 0.5 mg/kg, including 0.15 mg/kg, provide adequate treatment against ammonia as compared to untreated animals having compromised OTC function.

Figure 3B:
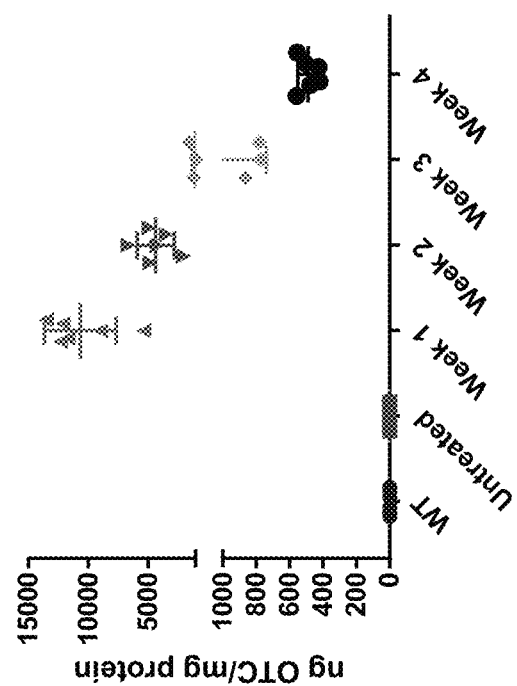
FIG. 3B is a graph that depicts translated hOTC protein production tested over the period the indicated.
Figure 3A:
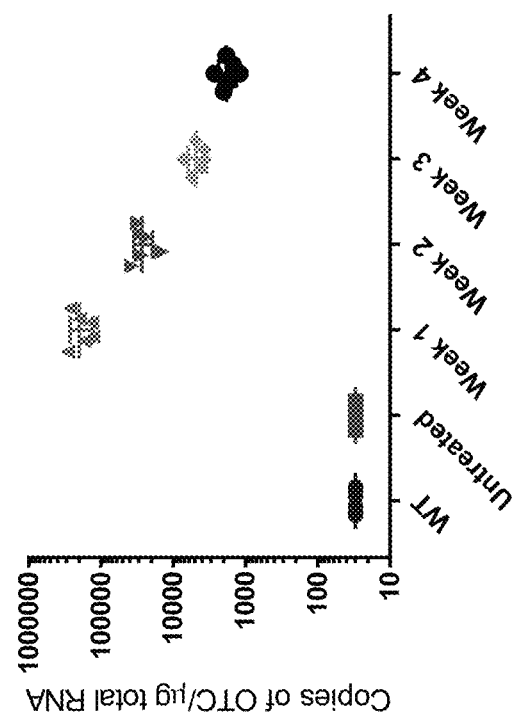
FIG. 3A is a graph that depicts copies of hOTC mRNA per microgram RNA tested over the period indicated.

Specifically, as shown in FIG. 3A and in FIG. 3B, the levels of hOTC mRNA and hOTC protein in the livers of animals administered 0.15 mg/kg on Day 1 significantly exceeded the baseline levels of mOTC mRNA and hOTC protein, respectively, in Wildtype (WT) and Untreated groups for up to and at least one week (i.e., at least 8 days following administration), for up to and at least two weeks (i.e., at least 15 days following administration), for up to and at least three weeks (i.e., at least 22 days following administration), and for up to and at least four weeks (i.e., at least 29 days following administration). In particular, as shown in FIG. 3A, high hOTC copy numbers exceeding 10^3 per microgram of total mRNA was detected in the treated animals at all timepoints out to 29 days after treatment, as compared to Wildtype and Untreated groups that showed less than 10^3 mOTC mRNA per microgram of total mRNA. As shown in FIG. 3B, hOTC protein expression levels in treated animals exceeded 200 nanograms hOTC protein per mg total protein at all timepoints out to 29 days after treatment, as compared to Wildtype and Untreated groups that showed no hOTC mRNA per mg total protein.

Figure 4B:
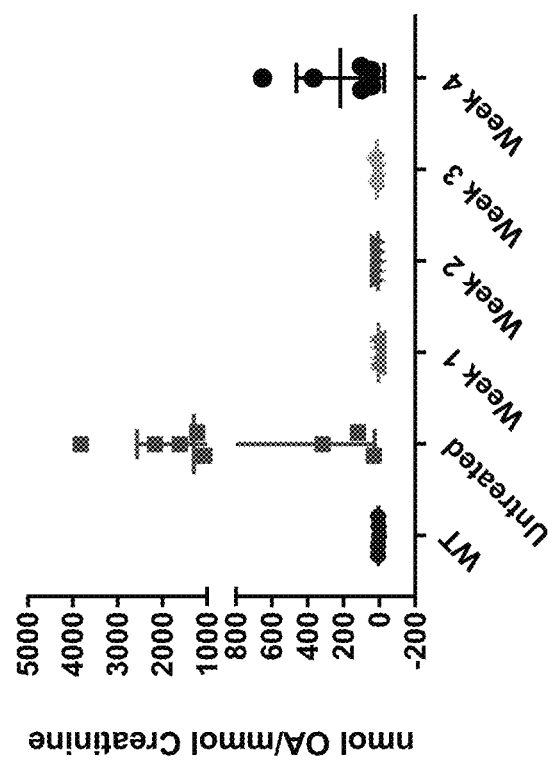
FIG. 4B is a graph that depicts urinary orotic acid levels at 24 hours after hOTC mRNA administration.
Figure 4A:
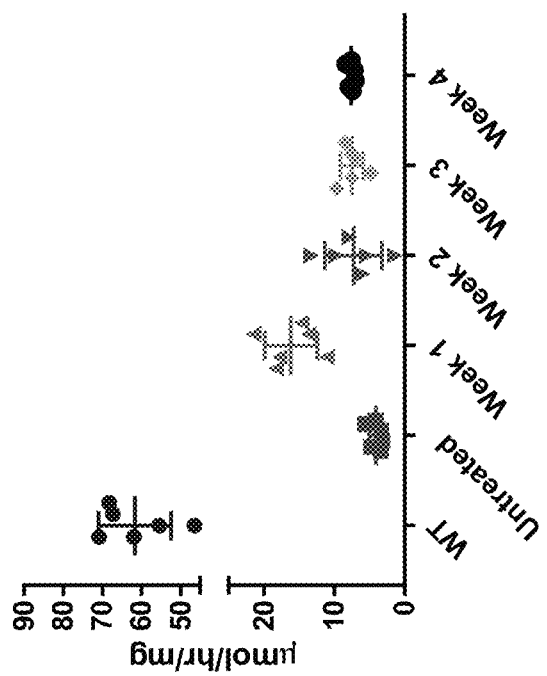
FIG. 4A is a graph that depicts citrulline levels at 24 hours after hOTC mRNA administration.

Moreover, as shown in FIG. 4A and in FIG. 4B, the protein provided from the single administration of 0.15 mg/kg mRNA in a lipid nanoparticle formulation was active for up to and at least one week (i.e., at least 8 days following administration), for up to and at least two weeks (i.e., at least 15 days following administration), for up to and at least three weeks (i.e., at least 22 days following administration), and for up to and at least four weeks (i.e., at least 29 days following administration). In particular, in FIG. 4A the citrulline levels at all timepoints were higher than for the untreated control group. In FIG. 4B, the urinary orotic acid levels remained much lower at all timepoints than the level for the untreated control group.

Example 2. Low-Dose OTC mRNA Across a Range of Doses Provides Significant Reduction in Hyperammonemia The study described in this example shows that a single low-dose (e.g., as low as 0.06 mg/kg) of hOTC mRNA delivered in a lipid nanoparticle formulation provides a potent reduction in hyperammonemia.

In this study, spf$^{ash}$ mice were randomized into six cohorts, with each cohort being administered hOTC in a lipid nanoparticle formulation at a dose of 0.06 mg/kg, 0.08 mg/kg, 0.10 mg/kg, 0.12 mg/kg, or 0.14 mg/kg mRNA, or the same volume of buffer (Untreated). After one day (24 hours) all animals were removed for assessment of response to ammonia challenge. As a reference control, a group of wild-type mice (WT) was treated with buffer at the same time as the treatment and Untreated groups and then also removed after one day (24 hours) for the same assessment. All doses were administered at 5.0 mL/kg via tail vein injection.

The assessment of response to ammonia challenge was conducted as described in Example 1, with reference to FIG. 1.

Figure 5:
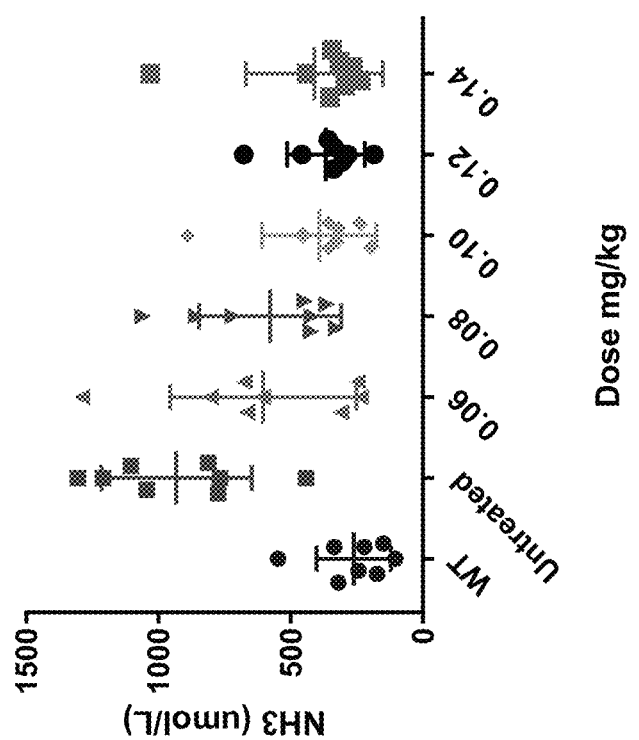
FIG. 5 is a graph that depicts reduction in and maintained reduction of ammonia levels (i.e., a hyperammonemic state) following hOTC mRNA administration at various dosages in the assay outlined in FIG. 1 at 24 hours following administration.

As shown in FIG. 5, a substantial reduction in the plasma ammonia levels was provided at each of the low doses of hOTC mRNA administered, as compared to the untreated control group. In particular, hOTC mRNA administered in a lipid nanoparticle formulation at low doses of 0.14 mg/kg, 0.12 mg/kg, and 0.10 mg/kg each showed reduction in hyperammonemia at one day following treatment that was comparable to the Wildtype (WT) control group, while hOTC mRNA administered in a lipid nanoparticle formulation at low doses of 0.08 mg/kg and 0.06 mg/kg each showed reduction in hyperammonemia that was well below the untreated control group.

Example 3. Successful Delivery of hOTC mRNA in a Lipid Nanoparticle Formulation to Hepatocytes in Primates The study in this example shows successful delivery of hOTC mRNA to and expression of hOTC protein in the liver, and particular in hepatocytes, of a primate following systemic administration to the primate of hOTC mRNA in a lipid nanoparticle formulation.

Specifically, male cynomolgus monkeys were treated with either hOTC mRNA in a lipid nanoparticle formulation or saline via slow infusion over 30 minutes. The hOTC mRNA in the lipid nanoparticle formulation was administered at a 0.30 mg/kg dose. Liver and spleen biopsies were harvested 24 hours post-administration and fixed in 10% neutral buffered formalin. In situ hybridization (ISH) was performed on fixed tissue samples for specific detection of hOTC mRNA. Immunohistochemical (IHC) analysis was performed on fixed tissue samples for detection of human OTC protein.

Figure 6B:
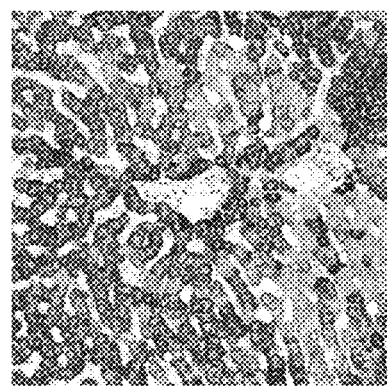
FIG. 6B is a graph that depicts detection of human OTC protein by immunohistochemistry in primate liver hepatocytes.
Figure 6B:
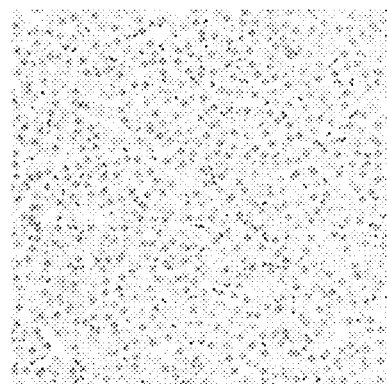
Figure 6A:
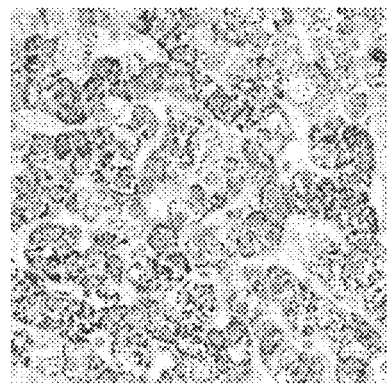
FIG. 6A is a graph that depicts detection of human OTC mRNA by in situ hybridization in primate liver hepatocytes.
Figure 6A:
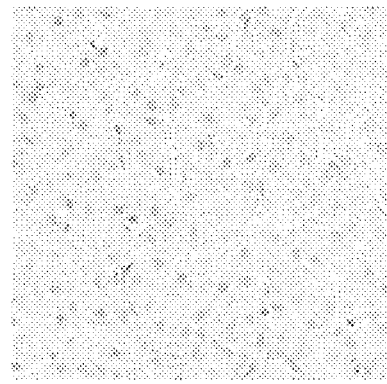

FIG. 6A depicts detection of human OTC mRNA by in situ hybridization in liver cells of primates 24 hours following systemic treatment with 0.30 mg/kg hOTC in a lipid nanoparticle formulation (right side), as compared to liver cells of primates treated with the saline control (left side). FIG. 6B depicts detection of human OTC protein by immunohistochemistry in liver cells of primates 24 hours following treatment with 0.30 mg/kg hOTC in a lipid nanoparticle formulation (right side), as compared to liver cells of primates treated with the saline control (left side). As shown in FIG. 6A and in FIG. 6B, hOTC mRNA and hOTC protein each are very clearly evident in the liver, and particularly in the hepatocytes of the primate livers, and not in the saline administered controls. In addition, hOTC mRNA and hOTC protein each were evident in the spleen as compared to the spleens of primates administered with a saline control. This extent of hOTC mRNA distribution to and hOTC protein expression in each of the liver, in hepatocytes and in the spleen of primates from a low-dose administration of 0.30 mg/kg hOTC mRNA in a lipid nanoparticle formulation was a surprising finding.

A projected minimal efficacious dose of the pharmaceutical composition comprising to a human or a primate can be determined from data obtained in mouse model.

It was found from Example 1 that the half-life of OTC activity was 22 days, which corresponded to an OTC protein half-life of 4.5 days and a hOTC mRNA half-life of 3 days (72 hours). In addition, data from male cynomolgus monkey experiment corresponding to FIGS. 6A and 6B, it was found that a dose to a primate of 0.3 mg/kg hOTC mRNA provides $3 \times 10^6$ copies of hOTC mRNA per milligram of liver at 72 hours, and based on the half-life of 72 hours, the hOTC mRNA exposure was calculated to be $5 \times 10^6$ copies of hOTC mRNA per milligram of liver at 24 hours.

The derived $EC_{10}$, the effective concentration to yield 10% of efficacious response, from the OTC-deficient mice study was determined to be $8 \times 10^4$ copies of hOTC mRNA per milligram of liver. Furthermore, it is known that the liver endogenous level of OTC in humans is approximately $1 \times 10^6$ copies OTC mRNA per milligram of liver and one-tenth of the endogenous level (i.e., $1 \times 10^5$ copies endogenous OTC mRNA per milligram of liver) or greater provides a therapeutically protective effect against hyperammonemia. The $EC_{10}$ was found to be in a comparable exposure range as one-tenth of human endogenous level, therefore, $EC_{10}$ was deemed pharmacologically relevant and selected to be the liver mRNA exposure target.

Accordingly, the data generated from Example 1 and Example 3, [two studies described above] was used to determine a minimally efficacious dose to a human or primate of 0.005 mg/kg. Specifically, the amount of hOTC mRNA in the liver at 24 hours required to achieve efficacy (i.e., $8 \times 10^4$ copies hOTC mRNA per milligram of liver) following dosing is projected to provide similar protection against hyperammonemia as one-tenth the typical level of endogenous mRNA OTC provides, for about 22 days or longer, based on the activity half-life determination described above. Using the primate dosing to copy number relationship determined above, i.e., 0.3 mg/kg dose=$5 \times 10^6$ copies of hOTC mRNA per milligram of liver at 24 hours, the minimally efficacious human or primate dose is 0.0048 mg/kg. Table 3 below provides a correspondence of hOTC mRNA copy number to human or primate dosages for a range of low yet efficacious dosages, using correlations from the results of the studies provided herein.

TABLE 3

| Human dose of hOTC mRNA (mg/kg) | hOTC mRNA copy number in liver at 24 hr (copies of hOTC mRNA per mg of liver at 24 hours) | % of human endogenous OTC mRNA (hOTC mRNA copies at 24 hours/endogenous human OTC mRNA x 100) |
|---|---|---|
| 0.30 | 5,000,000 | 625% |
| 0.29 | 4,833,333 | 604% |
| 0.28 | 4,666,667 | 583% |
| 0.27 | 4,500,000 | 563% |
| 0.26 | 4,333,333 | 542% |
| 0.25 | 4,166,667 | 521% |
| 0.24 | 4,000,000 | 500% |
| 0.23 | 3,833,333 | 479% |
| 0.22 | 3,666,667 | 458% |
| 0.21 | 3,500,000 | 438% |
| 0.20 | 3,333,333 | 417% |
| 0.19 | 3,166,667 | 396% |
| 0.18 | 3,000,000 | 375% |
| 0.17 | 2,833,333 | 354% |
| 0.16 | 2,666,667 | 333% |
| 0.15 | 2,500,000 | 313% |
| 0.14 | 2,333,333 | 292% |
| 0.13 | 2,166,667 | 271% |
| 0.12 | 2,000,000 | 250% |
| 0.11 | 1,833,333 | 229% |
| 0.10 | 1,666,667 | 208% |
| 0.09 | 1,500,000 | 188% |
| 0.08 | 1,333,333 | 167% |
| 0.07 | 1,166,667 | 146% |
| 0.06 | 1,000,000 | 125% |
| 0.05 | 833,333 | 104% |
| 0.04 | 666,667 | 83% |
| 0.03 | 500,000 | 63% |
| 0.02 | 333,333 | 42% |
| 0.01 | 166,667 | 21% |
| 0.009 | 150,000 | 19% |
| 0.008 | 133,333 | 17% |
| 0.007 | 116,667 | 15% |
| 0.006 | 100,000 | 13% |
| 0.005 | 83,333 | 10.4% |
| 0.0048 | 80,000 | 10.0% |

Example 4. Evaluation of hOTC mRNA Formulation in OTC-Deficient Human

The objective of this study is evaluating a single and multiple doses of a biosynthetic codon-optimized mRNA formulation in subjects with ornithine transcarbamylase deficiency (OTCD). The codon-optimized hOTC mRNA is manufactured by in vitro transcription, which upon cellular uptake undergoes normal translation producing a wild-type hOTC protein. The codon-optimized hOTC mRNA is formulated within a lipid nanoparticle (LNP). The LNP comprises an ionizable cationic lipid, MVL-2 ((3S,6R)-3,6-bis(4-(bis((R)-2-hydroxydodecyl)amino)butyl)piperazine-2,5-dione), 1,2-dioleoyl-SN-glycero-3-phosphoethanolamine (DOPE), cholesterol, and 1,2-dimyristoyl-rac-glycero-3-methylpolyoxyethylene (DMG-PEG-2K). The formulation is reconstituted and further diluted in 5% dextrose in water (D5W) and administered as an IV infusion over a minimum duration of 120 minutes with the hOTC mRNA a concentration of about 1.3 mg/ml.

Study Design

Some subjects receive a single dose of 0.01 mg/kg, 0.03 mg/kg, or 0.1 mg/kg of hOTC mRNA-LNP or placebo. Other subjects receive multiple doses of 0.01 mg/kg, 0.03 mg/kg, or 0.1 mg/kg of hOTC mRNA-LNP or placebo, at dosing intervals of two weeks. The placebo is 5% Dextrose in water (D5W).

The 3 doses for the study (i.e., 0.01 mg/kg, 0.03 mg/kg, 0.1 mg/kg) were selected based on the calculated liver concentration of OTC mRNA required to translate OTC protein sufficient to deliver OTC enzymatic activity as described in Example 3.

Subjects included for treatment exhibit one or more of the following:
  Confirmed pathogenic mutation of OTC deficiency.
  Abnormal liver OTC enzyme activity levels corresponding to a documented history of ≥1 symptomatic hyperammonemia event with ammonia ≥100 μmol/L in the 2 years prior.
  Ammonia level <175 μmol/L just prior to treatment.
  No clinical symptoms of hyperammonemia during just prior to treatment.
  Stable ureagenesis results, defined as no more than 25% difference between two 4-hr ureagenesis AUC values obtained just prior to treatment. The baseline ureagenesis results (defined as the average of two 4-hr ureagenesis AUC values just prior to treatment) should be ≤85% of normal.

Subjects are excluded from treatment if any of the following are observed (a) Platelet counts <$125 \times 10^9$/L; (b) prothrombin time (PT) international normalized ratio (INR) or activated partial thromboplastin time (aPTT)>1.25× upper limit of normal (ULN); (c) serum creatinine >2.0 mg/dL; or (d) abnormal liver function defined as meeting any 3 or more of the following:
  alanine aminotransferase (ALT)>3× upper limit of normal (ULN),
  aspartate aminotransferase (AST)>3×ULN,
  gamma-glutamyl transferase (GGT)>2.5×ULN,
  alkaline phosphatase>3×ULN, and/or
  total bilirubin>1.5×ULN (except for patients with isolated Gilbert Syndrome).

Subjects to be treated must be on a stable regimen if using nitrogen scavenger therapy for ≥28 days prior to treatment and must have maintained a stable protein restricted diet (which may or may not include medical foods) and/or amino acid supplementation with no changes in calorie or protein goals and no changes in medical food and/or amino acid supplementation for ≥28 days prior to treatment.

Subjects may continue on their standard of care therapy (i.e., nitrogen scavengers and restricted diet) while receiving mRNA therapy as described herein.

Study Objectives and Endpoints:
The objectives of this study include the following:
  To evaluate the effect of a single dose or multiple doses of hOTC mRNA-LNP on ureagenesis. Endpoint Analysis: Changes from baseline in 4-hour ureagenesis area under curve (AUC) at weeks 2, 3, 4 and 5 after a single dose of hOTC mRNA-LNP is measured. Changes from baseline in 4-hour ureagenesis AUC at Week 12 is measured as the endpoint for patients receiving multiple doses.

To evaluate the effect of single or multiple doses of hOTC mRNA-LNP on metabolic markers of OTCD, including levels of plasma ammonia and glutamine. Endpoint Analysis: Change from baseline in 8-hour ammonia AUC; change from baseline in fasting ammonia; and change from baseline in plasma glutamine are measured in the subject.

To determine an acceptable dosing interval of hOTC mRNA-LNP. Endpoint Analysis: The endpoint measurement for this objective is the measurement of duration of effect in change from baseline in 4-hr ureagenesis AUCs at specified visits.

To evaluate any immunogenicity of hOTC mRNA-LNP after single or multiple doses. Endpoint Analysis: This study will evaluate the percentage of subjects showing signs of immune responses to hOTC mRNA-LNP, such as development of anti-OTC antibodies, development or increasing titer of anti-PEG antibodies, or positive T-cell response of the subjects.

To evaluate the effect of single or multiple doses of hOTC mRNA-LNP on other amino acids. Endpoint Analysis: This study will evaluate change from baseline in plasma citrulline, alanine, arginine, glutamate, as well as the glutamine:citrulline ratio of the subjects.

To evaluate the effect of multiple doses of hOTC mRNA-LNP on measures of neurocognitive behavior (Behavior Rating Inventory of Executive Function [BRIEF]).

Pharmacokinetic Assessments

Whole blood for CO-hOTC mRNA levels and plasma samples for cationic lipid levels will be analyzed. For subjects receiving a single dose, a baseline sample will be obtained on Day 1 at predose and post-treatment samples will be collected on Day 1 at end of infusion (EOI), 2 hours post-EOI, 6 hours post-EOI, on Day 2 (24 hours post-EOI); on Day 3 (48 hours post-EOI); and on Day 8, 15, 22, and 29. For patients receiving multiple doses, a baseline sample will be obtained on Day 1 at pre-dose and post-treatment samples will be collected on Day 1 at EOI, 2 hours post-EOI, 6 hours post-EOI, at pre-dose only for Dose 2, 3, 4; and at pre-dose, EOI, and 2, 6, and 24 hours after Dose 5, as well as at Week 12, Week 16, and Week 22. The quantification of whole blood levels of CO-hOTC mRNA are performed by a quantitative PCR (qPCR) method. The quantification of plasma levels of cationic lipid are performed by an LC/MS (liquid chromatography/mass spectrometry) method.

The following pharmacokinetic parameters are calculated, when applicable:

Tmax—The time after dosing at which the maximum observed concentration is observed;
Cmax—The maximum observed concentration measured after dosing;
Cmax/D—The Cmax divided by the dose administered;
AUC(0-t)—The area under the concentration versus time curve from the start of dose administration to the time after dosing at which the last quantifiable concentration is observed, using the linear trapezoidal method;
AUC(0-t)/D—The AUC(0-t) divided by the dose administered;
t½—The apparent terminal elimination half-life;
V—Volume of distribution; and
CL—Clearance.

Pharmacological Assessments

Ureagenesis is measured following Yudkoff method (*Mol Genet Metab.* 2010; 100:S37-S41. doi:10.1016/j.ymgme.2010.02.017). Ureagenesis is measured by first allowing the subject to ingest $^{13}C$ acetate, which the liver rapidly converts to $^{13}CO_2$. The $^{13}CO_2$ is incorporated into several urea cycle intermediates before conversion to $^{13}C$-urea; the $^{13}C$-urea is measured in blood at sequential timepoints post-ingestion of $^{13}C$-acetate. The data are rendered as an area under the curve or as a point of maximal inflection of $^{13}C$-urea. If ureagenesis is compromised by a genetic deficiency in any of the enzymes controlling the urea cycle, these parameters may be demonstrably lower than control. Analysis of isotopic label in $^{13}C$-urea is performed through isotope ratio-mass spectrometry. The $^{13}CO_2$ is quantitated with isotope ratio-mass spectrometry. Data (isotopic enrichment) are rendered as atom % excess above a baseline ($T_0$) value.

In addition to isotopic enrichment in $^{13}C$-urea, total plasma urea (i.e., $^{13}C$-urea+$^{12}C$-urea) is measured independently with a standard chemical test (Berthelot reaction). The absolute concentration of $^{13}C$-urea then is the product of isotopic enrichment and total urea. Subjects will fast from midnight the night before until the ingestion of isotope. Blood will be collected for the ureagenesis assay at the following timepoints: pre-intake of $^{13}C$ sodium acetate, and at 30 (±5), 60 (±5), 90 (±5), 120 (±10), 180 (±10), and 240 (±15) minutes post-intake of $^{13}C$ sodium acetate.

Goal of the Study: The treatment goal for individuals affected with OTCD is the restoration of normal urea cycle function. The study described herein is a first-in-human trial on mRNA therapy.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

We claim:

1. A method of treating ornithine transcarbamylase (OTC) deficiency in a human, comprising administering to a human in need of treatment a pharmaceutical composition comprising an mRNA encoding an ornithine transcarbamylase protein formulated in a lipid nanoparticle,
   wherein the mRNA encoding the ornithine transcarbamylase protein is administered at a therapeutic low dose of 0.5 mg/kg or less of mRNA at a dosing interval of once every two weeks or a longer dosing internal for a period sufficient to treat at least one symptom or reduce the level of a biomarker associated with ornithine transcarbamylase deficiency in the human relative to a control.

2. The method of claim 1, wherein the therapeutic low dose is 0.4 mg/kg or less, or 0.3 mg/kg or less, or 0.2 mg/kg or less, or 0.15 mg/kg less, or 0.10 mg/kg or less, or 0.05 mg/kg or less, or 0.01 mg/kg or less, of mRNA encoding ornithine transcarbamylase protein.

3. The method of claim 1, wherein the longer dosing interval is once every three weeks or longer, or once every 4 weeks or longer.

4. The method of claim 1, wherein the mRNA is codon optimized.

5. The method of claim 1, wherein the symptom comprises hyperammonemia.

6. The method of claim 1, wherein the biomarker is selected from the group consisting of: high plasma ammonia level, high tissue ammonia level, urinary orotic acid, citrulline, serum glutamate, brain myoinositol, serum amino acids, and combination thereof.

7. The method of claim 1, wherein the mRNA is encapsulated in the lipid nanoparticle.

8. The method of claim 1, wherein the lipid nanoparticle comprises one or more cationic lipids.

9. The method of claim 1, wherein the lipid nanoparticle comprises one or more non-cationic lipids.

10. The method of claim 1, wherein the lipid nanoparticle comprises one or more PEGylated lipids.

11. The method of claim 1, wherein the pharmaceutical composition further comprises one or more excipients.

12. The method of claim 1, wherein the mRNA comprises one or more modified nucleotides.

13. The method of claim 1, wherein the administering of the pharmaceutical composition is performed intravenously.

14. The method of claim 1, wherein the mRNA is administered concurrently with an additional therapy.

15. The method of claim 1, wherein the administration results in distribution of the mRNA to the liver.

16. The method of claim 1, wherein the mRNA comprises a polynucleotide sequence at least 80% identical to SEQ ID NO: 4, SEQ ID NO: 5, SEQ ID NO: 6 SEQ ID NO: 7, SEQ ID NO: 8, SEQ ID NO: 9, or SEQ ID NO: 10.

17. The method of claim 1, wherein the mRNA comprises a polynucleotide sequence at least 90% identical to SEQ ID NO: 4, SEQ ID NO: 5, SEQ ID NO: 6 SEQ ID NO: 7, SEQ ID NO: 8, SEQ ID NO: 9, or SEQ ID NO: 10.

18. The method of claim 1, wherein the mRNA encodes an ornithine transcarbamylase protein comprising at least 90% identity to the amino acid of SEQ ID NO: 3.

* * * * *

SEQUENCE LISTING

<160> NUMBER OF SEQ ID NOS: 13

<210> SEQ ID NO 1
<211> LENGTH: 1065
<212> TYPE: RNA
<213> ORGANISM: Homo sapiens

<400> SEQUENCE: 1

```
augcuguuua aucugaggau ccuguuaaac aaugcagcuu uuagaaaugg ucacaacuuc      60
augguucgaa auuuucggug uggacaacca cuacaaaaua aagugcagcu gaagggccgu     120
```

| | |
|---|---|
| gaccuucuca cucuaaaaaa cuuuaccgga gaagaaauua aauauaugcu auggcuauca | 180 |
| gcagaucuga aauuuaggau aaaacagaaa ggagaguauu ugccuuuauu gcaagggaag | 240 |
| uccuuaggca ugauuuuuga gaaagaagu acucgaacaa gauugucuac agaaacaggc | 300 |
| uuugcacuuc ugggaggaca uccuuguuuu cuuaccacac aagauauuca uuugggugug | 360 |
| aaugaaaguc ucacggacac ggcccgugua uugucuagca uggcagaugc aguauuggcu | 420 |
| cgaguguaua aacaaucaga uuuggacacc cuggcuaaag aagcauccau cccaauuauc | 480 |
| aaugggcugu cagauuugua ccauccuauc cagauccugg cugauuaccu cacgcuccag | 540 |
| gaacacuaua gcucucugaa aggucuuacc cucagcugga ucggggaugg gaacaauauc | 600 |
| cugcacucca ucaugaugag cgcagcgaaa uucggaaugc accuucaggc agcuacucca | 660 |
| aagguuaug agccggaugc uaguguaacc aaguuggcag agcaguaugc aaagagaau | 720 |
| gguaccaagc uguugcugac aaaugaucca uuggaagcag cgcauggagg caauguauua | 780 |
| auuacagaca cuuggauaag cauggacaa gaagaggaga gaaaaagcg gcuccaggcu | 840 |
| uuccaagguu accagguuac aaugaagacu gcuaaaguug cugccucuga cuggacauuu | 900 |
| uuacacugcu ugcccagaaa gccagaagaa guggaugaug aagucuuuua uucuccucga | 960 |
| ucacuagugu ucccagaggc agaaaacaga aaguggacaa ucauggcugu cauggugucc | 1020 |
| cugcugacag auuacucacc ucagcuccag aagccuaaau uuuga | 1065 |

<210> SEQ ID NO 2
<211> LENGTH: 1065
<212> TYPE: DNA
<213> ORGANISM: Homo sapiens

<400> SEQUENCE: 2

| | |
|---|---|
| atgctgttta atctgaggat cctgttaaac aatgcagctt ttagaaatgg tcacaacttc | 60 |
| atggttcgaa attttcggtg tggacaacca ctacaaaata aagtgcagct gaagggccgt | 120 |
| gaccttctca ctctaaaaaa ctttaccgga gaagaaatta aatatatgct atggctatca | 180 |
| gcagatctga aatttaggat aaaacagaaa ggagagtatt tgcctttatt gcaagggaag | 240 |
| tccttaggca tgattttga gaaagaagt actcgaacaa gattgtctac agaaacaggc | 300 |
| tttgcacttc tgggaggaca tccttgtttt cttaccacac aagatattca tttgggtgtg | 360 |
| aatgaaagtc tcacggacac ggcccgtgta ttgtctagca tggcagatgc agtattggct | 420 |
| cgagtgtata acaatcaga tttggacacc ctggctaaag aagcatccat cccaattatc | 480 |
| aatgggctgt cagatttgta ccatcctatc cagatcctgg ctgattacct cacgctccag | 540 |
| gaacactata gctctctgaa aggtcttacc ctcagctgga tcgggatgg gaacaatatc | 600 |
| ctgcactcca tcatgatgag cgcagcgaaa ttcggaatgc accttcaggc agctactcca | 660 |
| aagggttatg agccggatgc tagtgtaacc aagttggcag agcagtatgc aaagagaat | 720 |
| ggtaccaagc tgttgctgac aaatgatcca ttggaagcag cgcatggagg caatgtatta | 780 |
| attacagaca cttggataag catgggacaa gaagaggaga gaaaaagcg gctccaggct | 840 |
| ttccaaggtt accaggttac aatgaagact gctaaagttg ctgcctctga ctggacattt | 900 |
| ttacactgct gcccagaaa gccagaagaa gtggatgatg aagtctttta ttctcctcga | 960 |
| tcactagtgt tcccagaggc agaaaacaga agtggacaa tcatggctgt catggtgtcc | 1020 |
| ctgctgacag attactcacc tcagctccag aagcctaaat tttga | 1065 |

<210> SEQ ID NO 3
<211> LENGTH: 354

<212> TYPE: PRT
<213> ORGANISM: Homo sapiens

<400> SEQUENCE: 3

```
Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35                  40                  45

Thr Gly Glu Glu Ile Lys Tyr Met Leu Trp Leu Ser Ala Asp Leu Lys
50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Ala Asp Ala Val Leu Ala Arg Val Tyr Lys
130                 135                 140

Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
            180                 185                 190

Trp Ile Gly Asp Gly Asn Asn Ile Leu His Ser Ile Met Met Ser Ala
        195                 200                 205

Ala Lys Phe Gly Met His Leu Gln Ala Ala Thr Pro Lys Gly Tyr Glu
210                 215                 220

Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
                245                 250                 255

Gly Asn Val Leu Ile Thr Asp Thr Trp Ile Ser Met Gly Gln Glu Glu
            260                 265                 270

Glu Lys Lys Lys Arg Leu Gln Ala Phe Gln Gly Tyr Gln Val Thr Met
        275                 280                 285

Lys Thr Ala Lys Val Ala Ala Ser Asp Trp Thr Phe Leu His Cys Leu
290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
            340                 345                 350

Lys Phe
```

<210> SEQ ID NO 4
<211> LENGTH: 1065
<212> TYPE: RNA
<213> ORGANISM: Artificial Sequence
<220> FEATURE:

<223> OTHER INFORMATION: Synthetic mRNA

<400> SEQUENCE: 4

| | |
|---|---|
| augcuguuca accugagaau ccugcugaac aacgccgccu ucagaaacgg ccacaacuuc | 60 |
| auggugagaa acuucagaug cggccagccc cugcagaaca aggugcagcu gaagggcaga | 120 |
| gaccugcuga cccugaagaa cuucaccggc gaggagauca aguacaugcu guggcugagc | 180 |
| gccgaccuga aguucagaau caagcagaag ggcgaguacc ugccccugcu gcagggcaag | 240 |
| agccugggca ugaucuucga agagaagc accagaacca gacugagcac cgagaccggc | 300 |
| uucgcccugc ugggcggcca ccccugcuuc cugaccaccc aggacaucca ccugggcgug | 360 |
| aacgagagcc ugaccgacac cgccagagug cugagcagca uggccgacgc cgugcuggcc | 420 |
| agaguguaca agcagagcga ccuggacacc cuggccaagg aggccagcau ccccaucauc | 480 |
| aacggccuga gcgaccugua ccaccccauc cagauccugg ccgacuaccu gacccugcag | 540 |
| gagcacuaca gcagccugaa gggcugacc cugagcugga ucggcgacgg caacaacauc | 600 |
| cugcacagca ucaugaugag cgccgccaag uucggcaugc accugcaggc cgccacccc | 660 |
| aagggcuacg agcccgacgc cagcgugacc aagcuggccg agcaguacgc caaggagaac | 720 |
| ggcaccaagc ugcugcugac caacgacccc cuggaggccg cccacggcgg caacgugcug | 780 |
| aucaccgaca ccuggaucag caugggccag gaggaggaga agaagaagag acugcaggcc | 840 |
| uuccagggcu accaggugac cauggaacc gccaaggugg ccgccagcga cuggaccuuc | 900 |
| cugcacugcc ugcccagaaa gcccgaggag guggacgacg agguguucua cagccccaga | 960 |
| agccuggugu ccccgaggc cgagaacaga aaguggacca ucauggccgu gauggugagc | 1020 |
| cugcugaccg acuacagccc ccagcugcag aagcccaagu ucuga | 1065 |

<210> SEQ ID NO 5
<211> LENGTH: 1065
<212> TYPE: RNA
<213> ORGANISM: Artificial Sequence
<220> FEATURE:
<223> OTHER INFORMATION: Synthetic mRNA

<400> SEQUENCE: 5

| | |
|---|---|
| augcuguuca accuucggau cuugcugaac aacgcugcgu uccggaaugg ucacaacuuc | 60 |
| augguccgga acuucagaug cggccagccg cuccagaaca aggugcagcu caaggggagg | 120 |
| gaccuccuca cccugaaaaa cuucaccgga gaagagauca aguacaugcu guggcuguca | 180 |
| gccgaccuca aauuccggau caagcagaag ggcgaauacc uuccuuugcu gcagggaaag | 240 |
| ucccugggga ugaucuucga agcgcagc acucgcacua gacugucaac ugaaaccggc | 300 |
| uucgcgcugc uggaggaca cccccugcuuc cugaccaccc aagauaucca ucugggugug | 360 |
| aacgaauccc ucaccgacac agcgcgggug cugucgucca uggcagacgc gguccucgcc | 420 |
| cgcguguaca agcagucuga ucuggacacu cuggccaagg aagccuccau uccuaucauu | 480 |
| aauggauugu ccgaccucua ccaucccauc cagauucugg ccgauuaucu gacucugcaa | 540 |
| gaacauuaca gcucccugaa gggcuuacc cuucgcugga ucggcgacgg caacaacauu | 600 |
| cugcacagca uuaugaugag cgcugccaag uuuggaaugc accuccaagc agcgaccccg | 660 |
| aagggauacg agccagacgc cuccgugacg aagcuggcug agcaguacgc caaggagaac | 720 |
| ggcacuaagc ugcugcucac caacgacccu cucgaagccg cccacggugg caacgugcug | 780 |
| aucaccgaua ccuggaucuc cauggacag gaggaggaaa agaagaagcg ccugcaagca | 840 |
| uuucaggggu accaggugac uaugaaaacc gccaaggucg ccgccucgga cuggaccuuc | 900 |

| | |
|---|---|
| uugcacuguc ugcccagaaa gcccgaagag guggacgacg agguguucua cagcccgcgg | 960 |
| ucgcuggucu uuccggaggc cgaaaacagg aaguggacua ucauggccgu gaugguaucc | 1020 |
| cugcugaccg auuacucccc gcagcugcag aaaccaaagu ucuga | 1065 |

<210> SEQ ID NO 6
<211> LENGTH: 1065
<212> TYPE: RNA
<213> ORGANISM: Artificial Sequence
<220> FEATURE:
<223> OTHER INFORMATION: Synthetic mRNA

<400> SEQUENCE: 6

| | |
|---|---|
| augcuuuuca accugagaau ucugcugaac aacgcagccu uccgcaacgg acacaacuuc | 60 |
| augguccgga acuucagaug cggacaaccg cugcagaaca agguccagcu caagggucgg | 120 |
| gaccuguuga cucuuaagaa uuucaccgga gaagaaauca aguacaugcu guggcuguuc | 180 |
| gccgaccuga aguuucgcau caagcagaag ggggaguacc uccccugcu gcaaggaaag | 240 |
| ucccugggaa ugauuuucga gaagcgcucc acccgcacua gacuuuccac cgaaaccggc | 300 |
| uucgcucugc ugggcggaca uccuugcuuu cugacgacuc aggacaucca ccucggagug | 360 |
| aacgaaucec ucaccgauac cgccagggug cugagcagca uggccgacgc ugugcuggcu | 420 |
| cgggugauaca agcagucga ccucgacacc cuggccaagg aagccucgau cccuaucauc | 480 |
| aauggccugu cagaccugua ccacccaauc cagauucugg ccgacuaccu gacucuccaa | 540 |
| gagcacuaca gcagccucaa ggggcucaca uuguccugga ucggcgacgg caacaacauc | 600 |
| cuucacucca uuaugaaguc ggccgccaaa ucgggaugc aucugcaggc agccaccccu | 660 |
| aagggauacg agcccgaugc cuccgugacc aagcuccgc aacaguaugc gaaggagaac | 720 |
| ggcaccaagc uccugcucac uaacgauccg uuggaagcug cccacggcgg aaacgugcug | 780 |
| auuaccgaca ccuggaucag caugggggcag gaagaagaga gaagaagcg gcugcaggcg | 840 |
| uuucagggu uaccaagucac caugaaaacu gccaaagucg cggcauccga cuggacuuuc | 900 |
| cugcacuguc ugccgaggaa ccagaggaa guggaugacg aagucuuca ucacccegg | 960 |
| ucgcuggugu ucceggaagc ggagaaccgg aaguggacca ucauggccgu gauggucucg | 1020 |
| cugcucaccg auuacucucc gcaacugcag aagcccaagu ucuga | 1065 |

<210> SEQ ID NO 7
<211> LENGTH: 1065
<212> TYPE: RNA
<213> ORGANISM: Artificial Sequence
<220> FEATURE:
<223> OTHER INFORMATION: Synthetic mRNA

<400> SEQUENCE: 7

| | |
|---|---|
| augcuguuua accugagaau ucugcugaac aacgccgcgu ucaggaacgg ccacaauuuc | 60 |
| augguccgca acuuuagaug cggacagccu cuccaaaaca agguccagcu caaggggcgg | 120 |
| gacuugcuga cccuuaagaa cuuuaccggc gaagagauca aguacaugcu gguguguca | 180 |
| gcggaccuga aguccgcau caagcagaaa ggggaguauc ugccgcugcu ccaaggaaag | 240 |
| ucgcucggca ugaucuucga gaagcgcucg accagaaccc gcuguccac ugaaacuggu | 300 |
| uucgcccuuc uggguggaca cccuuguuuc cugacaaccc aggacaucca ucugggcgug | 360 |
| aacgaaagcc ucacugacac cgccagggug cugagcucca uggccgacgc uguccuugcc | 420 |
| cgggugauaca agcagucga ucuggacacu cuggccaagg aagcgoccau ccgaucauu | 480 |

| | | |
|---|---|---|
| aacggacugu ccgaccugua ccacccgauc cagauucugg ccgacuaccu gaccuugcaa | 540 | |
| gagcacuaca gcucacugaa gggcuugacc cugagcugga ucggcgacgg aaacaacauu | 600 | |
| cugcauucga ucaugauguc cgcggccaag uucggaaugc aucugcaggc cgcaacuccc | 660 | |
| aagggauacg aaccugaugc guccgugacu aagcuggccg agcaguacgc aaaggaaaac | 720 | |
| ggcaccaagc ugcugcugac caacgacccg cucgaagcug cccacggagg gaacgugcuc | 780 | |
| auuaccgaca cuuggaucuc cauggggcag gaagaagaga agaagaagcg gcuccaggca | 840 | |
| uccaggguu accaggucac caugaaaacg gccaaagugg ccgcuucgga uggacuuuc | 900 | |
| cuccacugcc uucccgcaa accugaggaa guggaugaug aaguguucua ucccccacgc | 960 | |
| ucccucgugu uccccgaggc cgagaaucgg aaguggacca uuauggccgu gauggguca | 1020 | |
| cugcugaccg acuacagccc ccaacugcaa aagccgaagu ucuga | 1065 | |

<210> SEQ ID NO 8
<211> LENGTH: 1065
<212> TYPE: RNA
<213> ORGANISM: Artificial Sequence
<220> FEATURE:
<223> OTHER INFORMATION: Synthetic mRNA

<400> SEQUENCE: 8

| | | |
|---|---|---|
| augcuguuca accuccggau ccuccucaac aacgccgcgu uccgcaacgg ccacaacuuc | 60 | |
| augguccgga auuccgaug cggacagcca cugcagaaca agguccagcu gaagggccgg | 120 | |
| gacuugcuga cucucaagaa cuuuaccggg gaagaaauca aguacaugcu guggcuuucc | 180 | |
| gccgaccuga aguucagaau caagcagaag ggcgaauauc ucccccugcu gcaaggaaag | 240 | |
| agccugggca ugauuuucga gaagagaucg acacgcaccc ggcuguccac cgagacuggg | 300 | |
| uuugcccugc ugggaggaca cccguguuuc cugaccaccc aagauaucca ucucggagug | 360 | |
| aacgaauccc uuacugacac ugcccgcgug uuguccucca uggcugaugc agugcucgcu | 420 | |
| cggguguaca agcagagcga ccuggacacu cuggcgaagg aagccucaau uccuaucauu | 480 | |
| aacgggcugu cggaccugua ccacccgauc cagauucugg ccgacuaccu gacccugcaa | 540 | |
| gaacacuacu caagccugaa gggucuuacc cuguccugga ucggcgacgg caacaacauc | 600 | |
| cugcacucca ucaugauguc ggcgcgaag uucggaaugc accucaagc agcgacuccg | 660 | |
| aagggguacg agccagaugc cuccgugacc aagcuggcgg agcaguacgc uaaggaaaac | 720 | |
| ggaaccaagc ugcugcucac uaacgacccg uuggaagccg cccauggugg aaaugugcug | 780 | |
| aucacggaua ccuggaucag cauggggccag gaggaagaga agaagaaaag gcuccaggcc | 840 | |
| uccaagggu accaggucac caugaaaacc gccaaagucg ccgcauccga uuggaccuuc | 900 | |
| cuccacugcc ugcccggaa gccugaagag gucgacgacg aaguguucua ucucccgc | 960 | |
| ucccuugugu uccccgaggc cgagaacagg aaguggacca uuauggccgu gauggugucg | 1020 | |
| cuccugaccg acuacagccc gcagcugcag aagcccaagu ucuga | 1065 | |

<210> SEQ ID NO 9
<211> LENGTH: 1065
<212> TYPE: RNA
<213> ORGANISM: Artificial Sequence
<220> FEATURE:
<223> OTHER INFORMATION: Synthetic mRNA

<400> SEQUENCE: 9

| | | |
|---|---|---|
| augcuguuca aucuucggau ccugcugaac aacgccgccu uucggaacgg gcacaacuuc | 60 | |
| augguccgca acuuccgcug uggacagccg cugcagaaca agguccagcu uaagggccgg | 120 | |

| | |
|---|---|
| gaucuccuga cccugaagaa cuuuaccgga gaagaaauca aguacaugcu cuggcugagc | 180 |
| gccgaccuca aguccggau uaagcagaag ggggaguacc ucccgcugcu ucaaggaaag | 240 |
| ucccuggga ugaucuucga gaagcggagc acuaggacca ggcugucgac cgaaacgggc | 300 |
| uuugcacugc ugguggaca cccaugcuuc cugaccaccc aagauauuca ucucggcgug | 360 |
| aacgaauccu ugacugacac ugcgcgcguc cucucaucga uggcugaugc cguguuggcu | 420 |
| agaguguaca agcagucaga ccuggacacu cuggcuaagg aagccuccau uccgaucauc | 480 |
| aacggccugu ccgaccugua ccacccgauu cagauucugg ccgacuaccu gacccugcaa | 540 |
| gagcacuauu cgagccuuaa agggullgacc cuguccugga ucggcgacgg aaacaauauc | 600 |
| uugcacucca uuaugaugue cgccgccaag uucggcaugc aucccaagc cgcgacuccu | 660 |
| aagggullacg agcccgacgc auccgugaca aaacuggccg agcaguacgc gaaggaaaac | 720 |
| gguaccaagc uccugcugac caaugauccu cucgaggcug cgcacggagg aaacgugcuc | 780 |
| aucaccgaca ccuggaucag caugggacag gaagaggaaa agaaaaagcg ccugcaggca | 840 |
| uccagggcu accaagucac uaugaaaacc gccaaagugg ccgccucgga uuggaccuuc | 900 |
| cuucacugcc ugccaagaaa gccugaggaa guggacgacg aaguguucua ucccccccgc | 960 |
| ucucucgugu uccccgaggc cgagaaccgg aaguggacca ucauggccgu gauggucuca | 1020 |
| cugcucacug acuacagccc gcagcugcag aagcccaagu ucuaa | 1065 |

<210> SEQ ID NO 10
<211> LENGTH: 1065
<212> TYPE: RNA
<213> ORGANISM: Artificial Sequence
<220> FEATURE:
<223> OTHER INFORMATION: Synthetic mRNA

<400> SEQUENCE: 10

| | |
|---|---|
| augcuguuca accuccggau ucugcugaac aacgccgcuu ccgcaacgg ccacaauuuc | 60 |
| augguccgga acuucagaug cggccagccg uugcagaaca agguccagcu uaagggacgc | 120 |
| gaucugcuga cccugaagaa cuucaccgga gaggaaauca aguauaugcu guggcucucg | 180 |
| gccgaccuga aguucaggau caagcagaag ggggaguacc ucccgcuguu gcaaggaaag | 240 |
| ucccuggca ugauuuucga gaagcgcuca acucgcacca ggcucuccac cgaaacuggu | 300 |
| uuugccuuc ugggcgguca ccuugcuuu cugacgaccc aggacauuca ccucggagug | 360 |
| aaugagagcc ugaccgacac ugccagagug cuguccucca uggcggaugc aguguuggcg | 420 |
| cggguguaca agcagucaga ccuggacacc cuggcgaagg aagcgucaau ccccaucauu | 480 |
| aacggacuga gcgaccugua ccacccgauc cagauccucg ccgacuaccu gacucuccaa | 540 |
| gaacacuacu cguccugaa agggcugacc uugagcugga ucggcgacgg caacaacauc | 600 |
| cugcauucca ucaugaugag cgccgccaag uucggaaugc accuucaagc cgcaacaccg | 660 |
| aagggcuacg agcggaugc ucgcgugacc aagcuggccg agcaguacgc caaggaaaac | 720 |
| gggaccaagc ugcugcucac uaacgacccu cuggaagcug cucacgggg aaacgugcug | 780 |
| aucaccgaca ccuggauuuc caugggacag gaagaagaga aaagaagcg gcuucaggcg | 840 |
| uccaggguu accaagucac caugaaaacc gccaaagugg cagccagcga cuggacuuc | 900 |
| cugcauugue ccucggaa gccugaggaa guggaugacg aaguguuuua cucccccgc | 960 |
| ucccuggugu uccccgaggc cgagaaccgg aaguggacua ucauggccgu gauggucucc | 1020 |
| cuccugaccg auuacucccc acaacugcag aagcccaagu ucuga | 1065 |

```
<210> SEQ ID NO 11
<211> LENGTH: 140
<212> TYPE: RNA
<213> ORGANISM: Artificial Sequence
<220> FEATURE:
<223> OTHER INFORMATION: Synthetic oligonucleotide

<400> SEQUENCE: 11
ggacagaucg ccuggagacg ccauccacgc uguuuugacc uccauagaag acaccgggac      60
cgauccagcc uccgcggccg ggaacggugc auuggaacgc ggauucccccg ugccaagagu    120 gacucaccgu ccuugacacg                                                 140

<210> SEQ ID NO 12
<211> LENGTH: 105
<212> TYPE: RNA
<213> ORGANISM: Artificial Sequence
<220> FEATURE:
<223> OTHER INFORMATION: Synthetic oligonucleotide

<400> SEQUENCE: 12
cggguggcau cccugugacc ccucccagu gccucuccug gcccuggaag uugccacucc       60
agugcccacc agccuugucc uaauaaaauu aaguugcauc aagcu                    105

<210> SEQ ID NO 13
<211> LENGTH: 105
<212> TYPE: RNA
<213> ORGANISM: Artificial Sequence
<220> FEATURE:
<223> OTHER INFORMATION: Synthetic oligonucleotide

<400> SEQUENCE: 13
ggguggcauc ccugugaccc cuccccagug ccucuccugg cccuggaagu ugccacucca      60
gugcccacca gccuuguccu aauaaaauua aguugcauca aagcu                    105
```